(12) United States Patent
Merchant

(10) Patent No.: US 12,274,735 B2
(45) Date of Patent: Apr. 15, 2025

(54) IL-4-FUSION FORMULATIONS FOR TREATMENT OF CENTRAL NERVOUS SYSTEM (CNS) TUMORS

(71) Applicant: Medicenna Therapeutics, Inc., Vancouver (CA)

(72) Inventor: Fahar Merchant, Vancouver (CA)

(73) Assignee: Medicenna Therapeutics Inc., Toronto (CA)

( * ) Notice: Subject to any disclaimer, the term of this patent is extended or adjusted under 35 U.S.C. 154(b) by 635 days.

(21) Appl. No.: 16/753,978

(22) PCT Filed: Oct. 10, 2018

(86) PCT No.: PCT/IB2018/001284
§ 371 (c)(1),
(2) Date: Apr. 6, 2020

(87) PCT Pub. No.: WO2019/073299
PCT Pub. Date: Apr. 18, 2019

(65) Prior Publication Data
US 2020/0390861 A1 Dec. 17, 2020

Related U.S. Application Data

(60) Provisional application No. 62/570,578, filed on Oct. 10, 2017.

(51) Int. Cl.
| | | |
|---|---|---|
| A61K 38/00 | (2006.01) | |
| A61K 9/00 | (2006.01) | |
| A61K 38/16 | (2006.01) | |
| A61K 38/20 | (2006.01) | |
| A61K 47/42 | (2017.01) | |
| A61K 47/46 | (2006.01) | |
| A61P 35/00 | (2006.01) | |
| C07K 14/21 | (2006.01) | |
| C07K 14/54 | (2006.01) | |

(52) U.S. Cl.
CPC ........ *A61K 38/2026* (2013.01); *A61K 9/0085* (2013.01); *A61K 38/164* (2013.01); *A61K 47/42* (2013.01); *A61K 47/46* (2013.01); *A61P 35/00* (2018.01); *C07K 14/21* (2013.01); *C07K 14/5406* (2013.01); *C07K 2319/55* (2013.01)

(58) Field of Classification Search
CPC ...... A61K 38/225; A61K 38/64; A61K 47/42; A61K 47/46; A61K 9/0085; A61P 35/00; C07K 14/21; C07K 14/5406; C07K 2319/55
See application file for complete search history.

(56) References Cited

U.S. PATENT DOCUMENTS

| | | |
|---|---|---|
| 6,011,002 A | 1/2000 | Pastan et al. |
| 6,028,176 A | 2/2000 | Greve et al. |
| 6,130,318 A | 10/2000 | Wild et al. |
| 6,335,426 B1 | 1/2002 | Shanafelt et al. |
| 6,673,602 B1 | 1/2004 | Spear et al. |
| 6,737,511 B1 | 5/2004 | Youle et al. |
| 9,512,194 B2 | 12/2016 | Garcia et al. |
| 9,629,899 B2 | 4/2017 | Puri |
| 10,093,708 B2 | 10/2018 | Merchant |
| 10,106,592 B2 | 10/2018 | Merchant |
| 2003/0013851 A1 | 1/2003 | Powers et al. |
| 2004/0248260 A1 | 12/2004 | Heavner et al. |
| 2005/0106148 A1 | 5/2005 | Kay et al. |
| 2006/0035856 A1 | 2/2006 | Caput et al. |
| 2007/0160658 A1 | 7/2007 | Connor et al. |
| 2010/0183545 A1 | 7/2010 | Puri |
| 2010/0317577 A1 | 12/2010 | Youle et al. |
| 2011/0023680 A1 | 2/2011 | Wang |
| 2011/0319336 A1 | 12/2011 | Kawakami et al. |
| 2012/0294931 A1 | 11/2012 | Kim et al. |
| 2014/0050709 A1 | 2/2014 | Leen et al. |
| 2016/0151490 A1 | 6/2016 | Sampath et al. |
| 2016/0271231 A1 | 9/2016 | Merchant |
| 2016/0340649 A1 | 11/2016 | Brown et al. |
| 2019/0016797 A1 | 1/2019 | Arenas-Ramirez et al. |

FOREIGN PATENT DOCUMENTS

| | | |
|---|---|---|
| CN | 102792358 A | 11/2012 |
| CN | 102792358 | 3/2015 |
| JP | 6936934 B2 | 9/2021 |
| WO | WO1994004680 A1 | 3/1994 |
| WO | WO2001018051 A2 | 9/2000 |
| WO | WO2001025282 A1 | 4/2001 |
| WO | WO2001034645 A2 | 5/2001 |
| WO | WO2001062933 A3 | 8/2001 |
| WO | WO2002018422 A1 | 3/2002 |

(Continued)

OTHER PUBLICATIONS

Kazunari et al. Neurosurgery 38(4):p. 733-736, Apr. 1996.*
Ding et al. Neurol Res. Oct. 2010; 32(8), pp. 810-815.*
Weber et al. Journal of Neuro-Oncology. 2003; 64, pp. 125-137.*
Agholme et al. "An in vitro model for neuroscience: differentiation of SH-SY5Y cells into cells with morphological and biochemical characteristics of mature neurons." J Alzheimer's Disease 20: 1069-1082, 2010.
Allen et al. "Interleukin-13 Displaying Retargeted Oncolytic Measles Virus Strains Have Significant Activity Against Gliomas With Improved Specificity". Molecular Therapy, Sep. 2008 (Sep. 2008), vol. 16, No. 9, pp. 1556-1564, ISSN 1525-0016 See whole document.

(Continued)

*Primary Examiner* — Jeanette M Lieb
(74) *Attorney, Agent, or Firm* — Sara E. Sims; Christina A. MacDougall; Morgan, Lewis & Bockius LLP

(57) ABSTRACT

The present invention provides methods for the treatment of a central nervous system (CNS) tumor in a subject comprising administering and IL-4 targeted cargo protein formulated in an artificial cerebral spinal fluid formulation. The present invention also provides formulations and methods for administration along with a surrogate tracer for monitoring.

20 Claims, 15 Drawing Sheets

Specification includes a Sequence Listing.

(56) References Cited

FOREIGN PATENT DOCUMENTS

| WO | WO2006074451 A2 | 7/2006 |
|---|---|---|
| WO | WO2007146046 A2 | 12/2007 |
| WO | WO 2008101671 A2 | 8/2008 |
| WO | WO2009029601 A2 | 3/2009 |
| WO | WO2009140598 A1 | 5/2009 |
| WO | WO2010031185 A1 | 3/2010 |
| WO | WO2011106779 A1 | 9/2011 |
| WO | WO2012054929 A2 | 4/2012 |
| WO | WO2012088446 A1 | 6/2012 |
| WO | WO2012139112 A1 | 10/2012 |
| WO | WO2013112871 A1 | 8/2013 |
| WO | WO2015042705 A1 | 9/2014 |
| WO | WO2015042707 A1 | 4/2015 |
| WO | WO2015070210 A1 | 5/2015 |
| WO | WO2015117229 A1 | 8/2015 |
| WO | WO2016040441 A1 | 3/2016 |
| WO | WO2018112266 A1 | 6/2018 |
| WO | WO2019051204 A1 | 3/2019 |
| WO | WO2019073299 A1 | 4/2019 |
| WO | WO2020160639 A1 | 8/2020 |
| WO | WO2021258213 A1 | 12/2021 |

OTHER PUBLICATIONS

"Alzheimer's Disease", ninds.nih.gov/disorders/alzheimersdisease/alzheimersdisease.htm; Jan. 4, 2012; 3 total pages.
Bachran et al. "Anthrax Toxin-Mediated Delivery of the Pseudomonas Exotoxin A Enzymatic Domain to the Cytosol of Tumor Cells via Cleavable Ubiquitin Fusions" mBio vol. 4, pp. 201-213 (2013).
Bates, D.L., et al., "3QB7: Interleukin-4 mutant RGA bound to cytokine receptor common gamma," <<RCSB PDB>> Protein Data Bank, pp. 1-2 (Apr. 25, 2012).
Baeurle Patrick A. et al. "Bispecific T-cell engaging antibodies for cancer therapy", Cancer Research, Aacr, US Philadephia, PA, vol. 69, No. 12, Jun. 15, 2009 (Jun. 15, 2009), pp. 4941-4944, XP002665118, ISSN: 1538-7445, CAN-09-0547 [retrieved on Jun. 9, 2009] the whole document.
Bhatia et al., Innovative approaches for enhancing cancer gene therapy. Discovery Medicine 15(84): 309-317, 2013.
Boise et al. "bcl-x, a bcl-2-Related Gene That Functions as a Dominant Regulator of Apoptotic Cell Death" Cell, vol. 74, pp. 597-608 (1993).
Burt, B.M. et al. "Expression of Interleukin-4 Receptor Alpha in Human Pleural Mesothelioma is Associated with Poor Survival and Promotion of Tumor Inflammation". Clinical Cancer Research, Mar. 15, 2012 (Mar. 15, 2012), vol. 18, No. 6, pp. 1568-1577 See entire document.
Cao et al., In vivo delivery of a Bcl-xl fusion protein containing the TAT protein transduction domain protects against ischemic brain injury and neuronal apoptosis. J Neurosci 22(13): 5423-5431, 2002.
Candolfini et al. "Gene therapy-mediated delivery of targeted cytotoxin for glioma therapeutics". Proceedings of the National Academy of Sciences of the United States of America, Nov. 16, 2010 (Nov. 16, 2010), vol. 107, No. 46, pp. 20021-20026, ISSN 1091-6490.
Castro et al. "Therapy and Targeted Toxins for Glioma". Current Gene Therapy, Jun. 1, 2011 (Jan. 6, 2011), vol. 11, No. 3, pp. 155-180, ISSN 1875-5631.
C.E. Brown et al.: "Bioactivity and Safety of IL13R?2-Redirected Chimeric Antigen Receptor CD8+ T Cells in Patients with Recurrent Glioblastoma", Clinical Cancer Research, vol. 21, No. 18, Jun. 9, 2015 (Jun. 9, 2015), pp. 4062-4072, XP055362974, US ISSN: 1078-0432, DOI: 10.1158/1072-0432.CCR-15-0428 The whole document.
Cleary et al "Cloning and structural analysis of cDNAs for bcl-2 and a hybrid bcl-2/immunoglobulin transcript resulting from the t(14;18) translocation" Cell Press, vol. 47, No. 1, pp. 19-28 (1986).
Corren et al. "Lebrikizumab treatment in adults with asthma.", N Eng I J Med., Sep. 22, 2011, pp. 1088-1098, 365(1), Massachusetts Medical Society, Waltham, MA.

Creusot, et al., "Engineering cell-type selective immune responses using mechanism-based designer IL-4 cytokines," The Journal of Immunology, 186:57.8 (2011).
Cuny, G.D. Neurodegenerative diseases: challenges and opportunities. Future Med Chem 4(13): 1647-1649, 2012.
Diehn et al. "Cancer Stem Cells and Radiotherapy: New Insights Into Tumor Radioresistance" Journal of National Cancer Institute, vol. 98, pp. 1755-1757 (2006).
Eisenmesser et al., "Solution structure of interleukin-13 and insights into receptor engagement." J Mol. Biol., Jun. 2001, pp. 231-241, 310(1), Elsevier, Amsterdam, Netherlands.
Elgert, K. Immunology, understanding the immune system. New York: Wiley-Liss, Inc., 1996; pp. 323-326.
Feigin et al. Recent advances in Huntington's disease: implications for experimental therapeutics. Curr Opin Neurol 15: 483-489, 2002.
Fernandez et al. "Genetically Engineered Vesicular Stomatitis Virus in Gene Therapy; Application for Treatment of Malignant Disease". Journal of Virology, Jan. 2002 (2002), vol. 76, No. 2, pp. 895-904, ISSN 0022-538X See whole document.
Fernando, R. et al. "Breast cancer cell proliferation is inhibited by bAD: regulation of cyclin D1." The Journal of biological chemistry vol. 282,39 (2007): 28864-73.
Forster et al. Characterization of differentiated SH-SY5Y as neuronal screening model reveals increased oxidative vulnerability. J Biomlecul Screen 21(5): 496-509, 2016.
Fueller, J. et al. "C-RAF activation promotes BAD poly-ubiquitylation and turn-over by the proteasome." Biochemical and biophysical research communications vol. 370,4 (2008): 552-6.
Garland, L. et al. "Phase I trial of intravenous IL-4 Pseudomonas Exotoxin protein (NBI-3001) in patients with advanced solid tumors that express the IL-4 receptor". Journal of Immunotherapy, 2005, vol. 28; No. 4, pp. 376-381.
GenBank Accession No. Z23115, bcl XL gene [Homo sapiens] Oct. 7, 2008.
GenBank Accession No. 3QB7_A, chain A, Interleukin 4 [Homo sapiens] Apr. 25, 2012.
GenBank Accession No. Q07817, bcl gene apotosis [Homo sapiens] Feb. 28, 2018.
Halliday et al. Alzheimer's disease and inflammation: a review of cellular and therapeutic mechanisms. Clin Exp Pharmacol Physiol 27: 1-8, 2000.
Han, J. et al. "Analysis of the cancer genome atlas (TCGA) database identifies an inverse relationship between interleukin-13 receptor a1 and a2 gene expression and poor prognosis and drug resistance in subjects with glioblastoma multiforme". Journal of Neuro-Oncology, Nov. 22, 2017 (Nov. 22, 2017), vol. 136, No. 3, pp. 463-474 See entire document.
Harvey, A. "Overview of Cell Signaling Pathways in Cancer." Predictive Biomarkers in Oncology, edited by Sunil Badve and George Louis Kumar. 2019, pp. 167-182.
Hotchkiss et al., TAT-BH4 and TAT-Bcl-xl peptides protect against sepsis-induced lymphocyte apoptosis in vivo. J Immunol 176: 5471-5477, 2006.
Ichinose, M. et al. "Extracellular Bad fused to toxin transport domains induces apoptosis." Cancer research vol. 62,5 (2002): 1433-8.
Ito, et al., "Distinct structural requirements for interleukin-4 (IL-4) and IL-13 binding to the shared IL-13 receptor facilitate cellular tuning of cytokine responsiveness." J. Biol. Chem., Sep. 4, 2009, pp. 24289-24296, 284(36), ASBMB, Rockville, MD.
Joshi et al. "In Situ Expression of Interleukin-4 (IL-4) Receptors in Human Brain Tumors and Cytotoxicity of a Recombinant IL-4 Cytotoxin in Primary Glioblastoma Cell Cultures", Cancer Research, Nov. 15, 2001, pp. 8058-8061, vol. 61.
Juengst, E.T. What next for human gene therapy? BMJ 326: 1410-1411, 2003.
Junttila et al "Redirecting cell-type specific cytokine responses with engineered interleukin-4 superkines" Nat Chem Biol., vol. 8, No. 12, pp. 990-998 (2012).
Kahlon, et al., "Specific Recognition and Killing of Glioblastoma Multiforme by Interleukin 13-Zetakine Redirected Cytolytic T Cells", Cancer Research, 64:9160-9166 (2004).

(56) References Cited

OTHER PUBLICATIONS

Kreitman et al. "Recombinant Toxins Containing Human Granulocyte-Macrophage Colony-Stimulating Factor and Either Pseudomonas Exotoxin or Diphtheria Toxin Kill Gastrointestinal Cancer and Leukemia Cells" Blood vol. 90, pp. 252-259 (1997).
Laske et al. "Tumor regression with regional distribution of the targeted toxin TF-CRM107 in patients with malignant brain tumors" Nature, vol. 3, pp. 1362-1368 (1997).
Levin, et al., "Exploiting a natural conformational switch to engineer an interleukin-2 "superkine"," Nature 484:529-533 (A & B) (2012).
Lomonosova and Chinnadurai "BH3-only proteins in apoptosis and beyond: an overview" Oncogene, vol. 27, pp. S2-S19 (2009).
Madhankumar et al., "interleukin 13 mutants of enhanced avidity toward the glioma-associated receptor, IL 13Ralpha2." Neoplasia, Jan./Feb. 2004, pp. 15-22, 6(1), Neoplasia Press, Ann Arbor, MI.
Mardor, Y. et al. "Convection-Enhanced Drug Delivery of Interleukin-4 Pseudomonas Exotoxin (PRX321): Increased Distribution and Magnetic Resonance Marketing". J Pharmacol Exp Ther., Aug. 2009 (Aug. 2009). vol. 330(2), pp. 520-525, ISSN 0022-3565 (Print), 1521-0103 (Electronic), 0022-3565 (Linking) [online] [retrieved on Feb. 12, 2019 (Dec. 2, 2019)].
McCormick et al. Commentary: IL-4 and IL-13 receptors and signaling. Cytokine 75: 38-50, 2015.
Munitz et al. 2008. PNAS 105:7240-7245 (Year: 2008).
Murray, E.J. "Cloning Genes in Mammalian Cell-lines" in Molecular Biology and Biotechnology. Great Britain: The Royal Society of Chemistry, 2000, pp. 177-201.
Natoli, A. et al. "Targeting the IL-4/IL-13 signaling pathway sensitizes Hodgkin lymphoma cells to chemotherapeutic drugs." International journal of cancer vol. 133,8 (2013): 1945-54.
Oshima et al., "Conversion of interleukin-13 into a high affinity agonist by a single amino acid substitution." J. Biol. Chem., May 12, 2000, pp. 14375-14380, 275(19), ASBMB, Rockville, MD.
Oshima et al., "Characterization of a powerful high affinity antagonist that inhibits biological activities of human interleukin-13." J. Biol. Chem., May 4, 2001, pp. 15185-15191, 276(18), ASBMB, Rockville, MD.
Pahlman et al. Differentiation and survival influences of growth factors in human neuroblastoma. Eur J Cancer 31A(4): 453-458, 1995.
Partaledis et al., "In vitro selection and characterization of human immunodeficiency virus type 1 (HIV-1) isolates with reduced sensitivity to hydroxyethylamino sulfonamide inhibitors of HIV-1 aspartyl protease." J. Viral, Sep. 1995, pp. 5228-5235, 69(9), American Society for Microbiology, Washington DC.
Phillips, A.J. The challenge of gene therapy and DNA delivery. J Pharmacy and Pharmacol 53: 1169-1174, 2001.
Polzein, L. et al. "Identification of novel in vivo phosphorylation sites of the human proapoptotic protein BAD: pore-forming activity of BAD is regulated by phosphorylation." The Journal of biological chemistry vol. 284,41 (2009): 28004-20.
Post et al. "Targeted Cancer Gene Therapy Using a Hypoxia Inducible Factor-Dependent Oncolytic Andenovirus Armed with Interleukin-4". Cancer Research, Jul. 15, 2007 (Jul. 15, 2007), vol. 67, No. 14, pp. 6872-6881, ISSN 1538-7445 See whole document.
Puri et al. "Human Neurological Cancer Cells Express Interleukin-4 (IL-4) Receptors Which are Targets for the Toxic Effects of IL4-Pseudomonas Exotoxin Chimeric Protein". The International Journal of Cancer, 1994, vol. 58, pp. 574-581, ISSN 1097-0215.
Reynolds et al., "Genetic Instability Induced by the Tumor Microenvironment", Cancer Research, vol. 56, pp. 5754-5757 (1996).
Rochman et al., 2009. 9(7) p. 1-23 (Year: 2009).
Rubanyi, G.M., The future of human gene therapy. Molecular Aspects Med 22: 113-142, 2001.
Rubin "Neuronal cell death: when, why and how" British Medical Bulletin, vol. 53, Issue 3, pp. 617-631 (1997).
Sakariassen et al. "Cancer Stem Cells as Mediators of Treatment Resistance in Brain Tumors: Status and Controversies" Neoplasia, vol. 9, No. 11, pp. 882-892 (2007).

Schnare et al., "Specific Antagonism of Type I IL-4 Receptor with a Mutated Form of Murine IL-4," The Journal of Immunology, 161:7, pp. 3484-3492 (1998).
Sharma et al. "Interleukin-4 Mediates Down Regulation of Antiviral Cytokine Expression and Cytotoxic T-Lymphocyte Responses and Exacerbates Vaccinia Virus Infection In Vivo". Journal of Virology, Oct. 1996, vol. 70, No. 10, pp. 7103-7107, ISSN 0022-538X See whole document.
Shimamura et al. "The IL-4 and IL-13 pseudomonas exotoxins: new hope for brain tumor therapy". Neurosurgical Focus, 2006, vol. 20, No. 3:E11, ISSN 1092-0684.
Shimamura et al. "Interleukin-4 Cytotoxin Therapy Synergizes with Gemcitabine in a Mouse Model of Pancreatic Ductal Adenocarcinoma" Cancer Research, vol. 67, pp. 9903-9912 (2007).
Steece-Collier et al. Etiology of Parkinson's disease: genetics and environment revisited. Proc Natl Acad Sci USA 99(22): 13972-13974, 2002.
Suga et al. "Transplant Immunosuppression Enhances Efficiency of Adenoviral-Mediated Gene Retransfection: Inhibition of Interferon-y and Immunoglobin G" The Society of Thoracic Surgeons, vol. 73, pp. 1092-1097 (2002).
Thompson, et al., "Mutants of interleukin 13 with altered reactivity toward interleukin 13 receptors." J. Biol. Chem., Oct. 15, 1999, pp. 29944-29950, 274(42), ASBMB, Rockville, MD.
Thorpe et al. "Toxicity of diphtheria toxin for lymphoblastoid cells is increased by conjugation to antilymphocytic globulin" Nature, vol. 271, pp. 752-755 (1978).
Tsujimoto and Croce "Analysis of the structure, transcripts, and protein products of bcl-2, the gene involved in human follicular lymphoma" Proc. Natl. Acad. Sci., vol. 83, pp. 5214-5218 (1986).
UniProtKB database P05112 (Aug. 13, 1987).
Vallera, D.A. et al. "Retroviral immunotoxin gene therapy of leukemia in mice using leukemia-specific T cells transduced with an interleukin-3/Bax fusion protein gene." Human gene therapy vol. 14, 18 (2003): 1787-98.
Van Den Broek, et al. "IL-4 and IL-10 Antagonize IL-12-Mediated Protection Against Acute Vaccinia Virus Infection with a Limited Role of IFN-γ and Nitric Oxide Synthetase 2". Journal of Immunology, Jan. 1, 2000 (Jan. 1, 2000), vol. 164, No. 1, pp. 371-378, ISSN 1550-6606.
White "Life, Death, and the Pursuit of Apoptosis" Genes and Development 10, pp. 1-15 (1996).
Yang et al. "Bad, a heterodimeric partner for Bcl-XL and Bcl-2, displaces Bax and promotes cell death" Cell, vol. 80, pp. 285-291 (1995).
Yang et al. Targeting cancer stern cell pathways for cancer therapy. Signal Transd Targeted Ther 5:8, 2020 (35 total pages).
Yeung et al. Signaling pathways in inflammation and anti-inflammatory therapies. Curr Pharm Design 24: 1449-1484, 2018.
Youle et al. "Receptor-mediated uptake of an extracellular Bcl-xL fusion protein inhibits apoptosis" Proceedings of Nat'l Academy of Sciences, vol. 96, pp. 9563-9567 (1999).
Youle et al. "The Cytokine, Granulocyte-Macrophage Colony-stimulating Factor (GM-CSF), Can Deliver Bcl-XL as an Extracellular Fusion Protein to Protect Cells from Apoptosis and Retain Differentiation Induction" The Journal of Biological Chemistry, vol. 282, No. 15, pp. 11246-11254 (2007).
Youle et al., "The BCL-2 protein family: opposing activities that mediate cell death", Nature Reviews, vol. 9, pp. 47-59 (2008).
ISR/WO issued in PCT/IB2018/001284 on Mar. 11, 2019.
Hallett, M.A. et al., Cancer Res., (Dec. 7, 2012), vol. 72, No. 24, pp. OF1-OF6.
Kawakami, M. et al., J. Neurooncol., (2003), vol. 65, pp. 15-25.
Ngo et al. "Computational complexity, protein structure prediction, and the Levinthal paradox" in The Protein Folding Problem and Tertiary Structure Prediction, pp. 492-495, 1994.
Skolnick et al. From genes to protein structure and function: novel applications of computational approaches in the genomic era. Trends Biotechnol 18(1) :34-39 2000.
Smith et al. The challenges of genome sequence annotation or "the devil is in the details". Nature Biotechnol 15: 1222-1223, 1997.
Tokuriki et al. Stability effects of mutations and protein evolvability. Curr Opin Structural Biol 19: 596-604, 2009.

(56) References Cited

OTHER PUBLICATIONS

Wang et al. Mono- or double-site phosphorylation distinctly regulates the proapoptotic function of Bax. PLoS One 5(10): e13393, 2010 (8 total pages).
Wells, J.A. Additivity of mutational effects in proteins. Biochemistry 29(37): 8509-8517, 1990.
Oka K, Yamamoto M, Nonaka T, Tomonaga M. The significance of artificial cerebrospinal fluid as perfusate and endoneurosurgery. Neurosurgery. Apr. 1996;38(4):733-6. PMID: 8692392.
CN 102792358 translation, 2012, pp. 1-40.
Post, Dawn E., et al. "Local delivery of the anti-tumorigenic interleukin-4 (IL-4) cytokine to tumors using an oncolytic adenovirus." Cancer Res May 1, 2005; 65 (9_Supplement): 317.
Sosman, J A et al. "A phase I trial of continuous infusion interleukin-4 (IL-4) alone and following interleukin-2 (IL-2) in cancer patients." Annals of oncology : official journal of the European Society for Medical Oncology vol. 5,5 (1994): 447-52. doi:10.1093/oxfordjournals.annonc.a058878.
Suzuki, Akiko et al. "Targeting of IL-4 and IL-13 receptors for cancer therapy." Cytokine vol. 75,1 (2015): 79-88. doi:10.1016/j.cyto.2015.05.026.
ISR and WO issued in PCT/US2013/054164 on May 7, 2014.
ISR issued in PCT/US2017/066529 on Apr. 9, 2018, and IPRP issued in PCT/US2017/066529 on Jun. 18, 2019.
ISR/WO issued in PCT/IB2019/000759 on Jan. 20, 2020.
ISR/WO issued in PCT/CA2020/000013 on May 15, 2020.
Ding et al., Convection-enhanced Delivery of Free Gadolinium with the Experimental Chemotherapeutic Agent PRX321., Neurol Res. Oct. 2010; 32(8): 810-815.
Weber et al., Safety, tolerability, and tumor response of IL4-Pseudomonas exotoxin (NBI-3001) in patients with recurrent malignant glioma., J Neurooncol. Aug.-Sep. 2003;64(1-2):125-37. doi: 10.1007/BF02700027.
Thaci et al., "Significance of interleukin-13 receptor alpha 2-targeted glioblastoma therapy," Neuro Oncol. Oct. 2014;16(10):1304-12.
ISR/WO issued in PCT/CA2021/051433 on Jan. 12, 2022.
Sampson et al., "MDNA55, a Locally Administered IL4 Guided Toxin for Targeted Treatment of Recurrent Glioblastoma Shows Long Term Survival Benefit," European Journal of Cancer (2020). 138. S6. 10.1016/S0959-8049(20)31084-4.
Medicenna, "Convection-Enhanced Delivery (CED) of MDNA55 in Adults With Recurrent or Progressive Glioblastoma," Clinical Trial NCT02858895, First posted Aug. 8, 2016. (https://clinicaltrials.gov/study/NCT02858895).
Bautz, "Medicenna Therapeutics Corp.," Zacks Small-Cap Research, May 14, 2019 (May 14, 2019), acquired from: http://s27.q4cdn.com/906368049/files/News/2019/Zacks_SCR_Research_05142019_T.MDNA_Bautz.pdf.
Yu et al., "Efficacy and safety of bevacizumab for the treatment of glioblastoma," Exp Ther Med. Feb. 2016;11(2):371-380.
Gramatzki et al., "Bevacizumab may improve quality of life, but not overall survival in glioblastoma: an epidemiological study," Ann Oncol. Jun. 1, 2018;29(6):1431-1436.
ISR/WO issued in PCT/IB2023/000132 on Oct. 13, 2023.
U.S. Appl. No. 14/419,873, filed Feb. 5, 2015, now U.S. Pat. No. 9,738,696.
U.S. Appl. No. 15/662,180, filed Jul. 27, 2017, now U.S. Pat. No. 10,738,096.
U.S. Appl. No. 16/988,460, filed Aug. 7, 2020.
U.S. Appl. No. 14/373,498, filed Jul. 21, 2014, now U.S. Pat. No. 9,512,194.
U.S. Appl. No. 15/353,273, filed Nov. 16, 2016, now U.S. Pat. No. 9,732,133.
U.S. Appl. No. 15/597,823, filed May 17, 2017, now U.S. Pat. No. 10,227,389.
U.S. Appl. No. 16/258,420, filed Jan. 25, 2019, now U.S. Pat. No. 11,084,858.
U.S. Appl. No. 17/388,895, filed Jul. 29, 2021.
U.S. Appl. No. 16/470,098, filed Jun. 14, 2019.
U.S. Appl. No. 15/024,785, filed Mar. 24, 2016, now U.S. Pat. No. 10,093,708.
U.S. Appl. No. 16/125,075, filed Sep. 7, 2018, now U.S. Pat. No. 11,084,856.
U.S. Appl. No. 17/397,287, filed Aug. 9, 2021.
U.S. Appl. No. 15/024,787, filed Mar. 24, 2016, now U.S. Pat. No. 10,106,592.
U.S. Appl. No. 16/125,566, filed Sep. 7, 2018, now U.S. Pat. No. 11,352,402.
U.S. Appl. No. 17/738,620, filed May 6, 2022.
U.S. Appl. No. 16/753,978, filed Apr. 6, 2020.
U.S. Appl. No. 15/733,815, filed Nov. 30, 2020.
U.S. Appl. No. 17/428,697, filed Aug. 5, 2021.
Bhattacharya et al. Impact of genetic variation on three dimensional structure and function of proteins. PLoS One 12(3): e0171355, 2017.
Bork, P. Powers and pitfalls in sequence analysis: the 70% hurdle. Genome Res 10: 398-400, 2000.
Brenner. S.E. Errors in genome annotation. Trends in Genetics 15:132-133, 1999.
Chen et al. Fusion protein linkers: property, design, and functionality. Adv Drug Rev 65: 1357-1369, 2013 (online Sep. 29, 2012).
Doerks et al. Protein annotation: detective work for function prediction. Trends in Genetics 14:248-250, 1998.
Fenton et al. Rheostat positions: a new classification of protein positions relevant to pharmacogenomics. Medicinal Chem Res 29:1133-1146, 2020.
Gardai et al. Phosphorylation of Bax Ser184 by Akt regulates its activity and apoptosis in neutrophils. J Biol Chem 279(20): 21085-21095, 2004.
Guo et al. Protein tolerance to random amino acid change. Proc Natl Acad Sci USA 101 (25): 9205-9210, 2004.

* cited by examiner

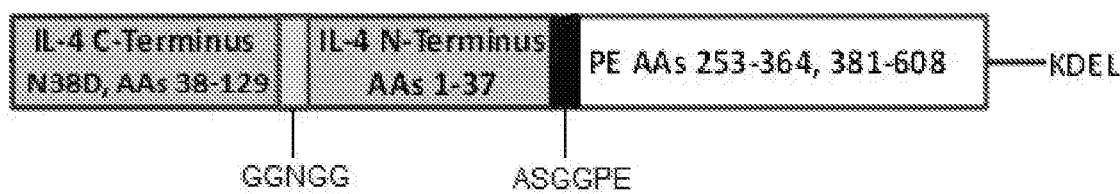

B)

PRX 321 (SEQ ID NO:1)

MDTTEKETFCRAATVLRQFYSHHEKDTRCLGATAQQFHRHKQLIRFLKLRDRNLWGLAGL
NSCPVKEANQSTLENFLERLKTIMREKYSKCSSGGNGGHKCDITLQEIIKTLNSLTEQKT
LCTELTVTDIFAASKASGGPEGGSLAALTAHQACHLPLETFTRHRQPRGWEQLEQCGYPV
QRLVALYLAARLSWNQVDQVIRNALASPGSGGDLGEAIREQPEQARLALTLAAAESERFV
RQGTGNDEAGAANGPADSGDALLERNYPTGAEFLGDGGDVSFSTRGTQNWTVERLLQAHR
QLEERGYVFVGYHGTFLEAAQSIVFGGVRARSQDLDAIWRGFYIAGDPALAYGYAQDQEP
DARGRIRNGALLRVYVPRSSLPGFYRTSLTLAAPEAAGEVERLIGHPLPLRLDAITGPEE
EGGRLETILGWPLAERTVVIPSAIPTDPRNVGGDLDPSSIPDKEQAISALPDYASQPGKP
PKDEL

*Figure 3*

Experimental Catheters and No Planning Software
Use FDA Approved or CE Marked Catheters & Planning Software in Future Trials

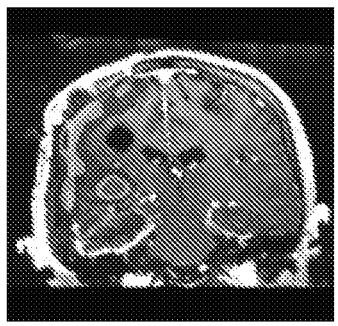 

- Poor Catheter Design
- Bad Catheter Placement
- Drug Leaks (Backflow)
- Risk of Side Effects

- Designed and Approved for CED
- No Backflow or Leakage
- Accurate Catheter Placement
- Real-time Monitoring
- Improve Efficacy
- Reduced Risk of Side Effects

*Figure 6*

| Drug related TEAEs | Worst CTCAE Grade (n) | | | | Comments |
|---|---|---|---|---|---|
| | Grade 4 | Grade 3 | Grade 2 | Grade 1 | |
| Fatigue | | | 1 | | |
| Lower limb muscle weakness | | | 1 | | |
| Seizure | | | 2 | | |
| Speech hesitancy | | | | 1 | During infusion |
| Headache | | | | 1 | |
| Paresthesia | | | | 1 | During infusion |
| Confusion | | | | 1 | During infusion |
| Dizziness | | | | 1 | |

| SAEs | Worst CTCAE Grade (n) | | | | Comments |
|---|---|---|---|---|---|
| | Grade 4 | Grade 3 | Grade 2 | Grade 1 | |
| Stroke | | 1 | | | Unrelated |
| Dehydration | | 1 | | | Unrelated |
| Seizure | | | 1 | | Related |

*Figure 7*

| AEs ≥ Gd 3 | Worst CTCAE Grade (n) | | Comments |
|---|---|---|---|
| | Grade 4 | Grade 3 | |
| STROKE | | 1 | Possibly related |
| LOW LYMPHOCYTES | | 1 | Unrelated |
| HIGH GLUCOSE | | 1 | Unrelated |
| DEHYDRATION | | 1 | Unrelated |
| LOW PLATELETS | | 1 | Unrelated |
| LOW LYMPHOCYTES | | 3 | Unrelated, low baselines |

- Labs: no other ≥ Gd2 abnormalities. ACS low lymphocytes in 5 subjects.
- Vital signs: largely unremarkable. Some bradycardia during catheter placement / infusion.
- No clear dose / volume effects
- No evidence of CSF toxicity following local administration of Gadolinium

Figure 8

Disease and Diagnosis:
- Initial diagnosis: Gd IV Primary GBM
- Date of diagnosis: 26 FEB 2014
- Max diameter at initial diagnosis: 1.65cm
- Treatments: Total resection, radiotherapy, temozolomide
- Date of most recent PD: 11 MAR 2017
- KPS at study entry: 70

Date of CED: 14-APR-2017

Status within study (as of June 14th 2017)

| Max tumor diameter (cm) | Delivered infusion volume (ml) | Number of catheters (functioning) | Adverse Events Reported (≥ Grade 2 and suspected to be related to MDNA55) | Relevant Abnormal Labs (≥ Grade 2) | SAE(s) reported |
|---|---|---|---|---|---|
| 2.1 | 15.02 | 2(1) | Fatigue (Gd 2) Lower limb muscle weakness (Gd 2) | 0 | 2 |

Figure 9
A)
B)
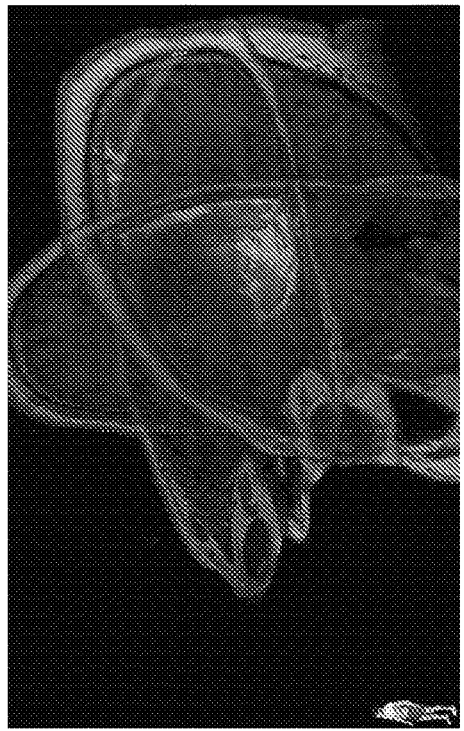
C)
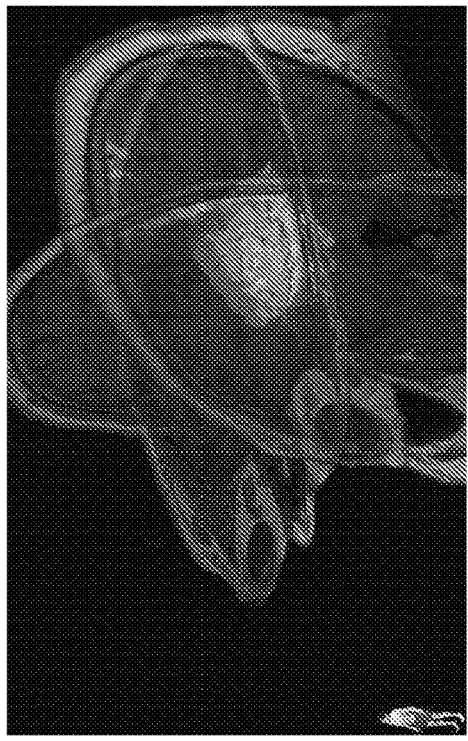
D)

*Figure 10*

Disease and Diagnosis:
- Initial diagnosis: Gd IV Primary GBM
- Date of diagnosis: 04 AUG 2016
- Max diameter at initial diagnosis: 4.7 cm
- Treatments: total resection, radiotherapy (proton beam), temozolomide
- Date of most recent PD: 08 MAR 2017
- KPS at study entry: 100

Date of CED: 11-APR-2017

| Status within study (as of June 14th 2017) | | | | | |
|---|---|---|---|---|---|
| Max tumor diameter (cm) | Delivered infusion volume (ml) | Number of catheters (functioning) | Adverse Events Reported (≥ Grade 2 and suspected to be related to MDNA55) | Relevant Abnormal Labs (≥ Grade 2) | SAE(s) reported |
| 3.6 | 17 | 2(2) | Seizure (Gd 2) | 0 | 0 |

*Figure 14*
A)
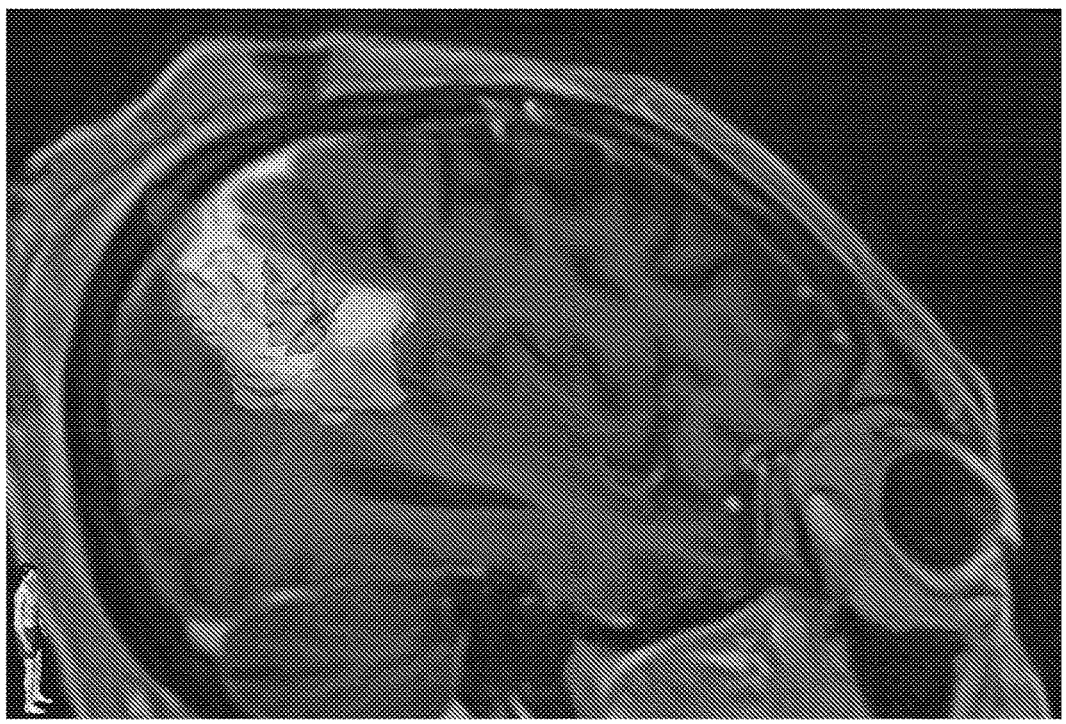
B)
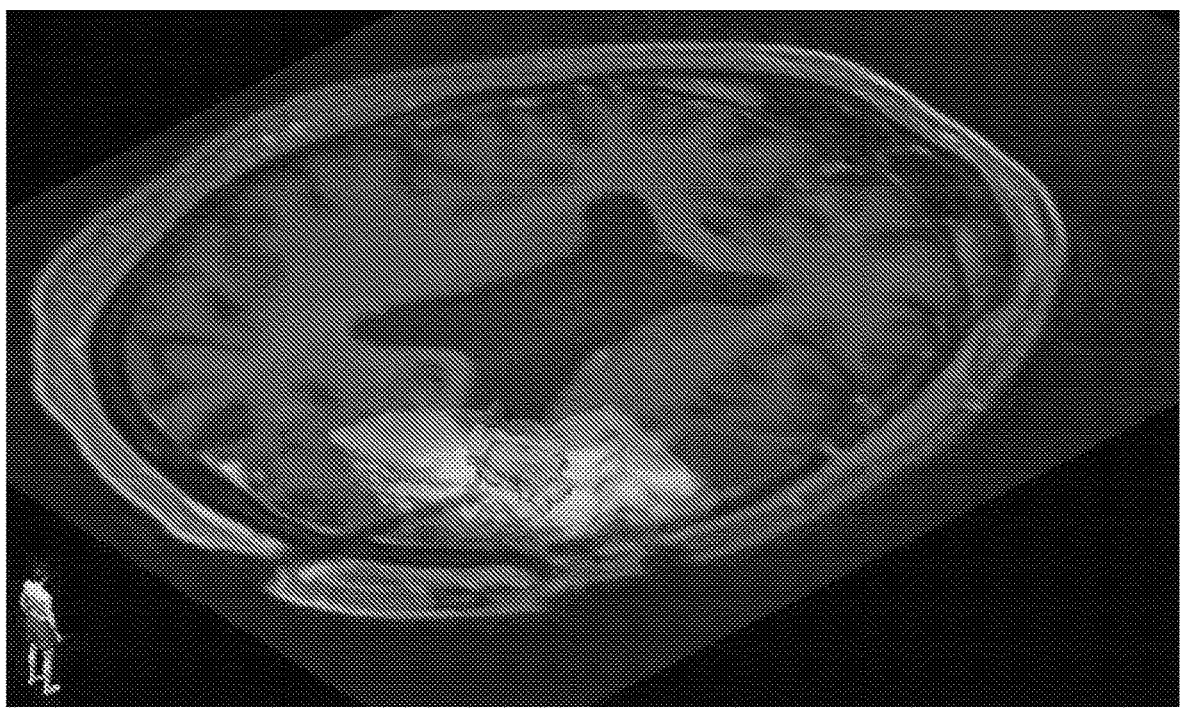

SEQUENCE LISTING

<160> NUMBER OF SEQ ID NOS: 1

<210> SEQ ID NO 1
<211> LENGTH: 485
<212> TYPE: PRT
<213> ORGANISM: Artificial Sequence
<220> FEATURE:
<223> OTHER INFORMATION: Synthetic

<400> SEQUENCE: 1

```
Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Leu Arg Asp Arg Asn Leu Trp Gly Leu Ala Gly Leu Asn Ser Cys Pro
50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Lys Ala Ser Gly Gly Pro Glu Gly Gly Ser
    130                 135                 140

Leu Ala Ala Leu Thr Ala His Gln Ala Cys His Leu Pro Leu Glu Thr
145                 150                 155                 160

Phe Thr Arg His Arg Gln Pro Arg Gly Trp Glu Gln Leu Glu Gln Cys
                165                 170                 175

Gly Tyr Pro Val Gln Arg Leu Val Ala Leu Tyr Leu Ala Ala Arg Leu
            180                 185                 190

Ser Trp Asn Gln Val Asp Gln Val Ile Arg Asn Ala Leu Ala Ser Pro
        195                 200                 205

Gly Ser Gly Gly Asp Leu Gly Glu Ala Ile Arg Glu Gln Pro Glu Gln
    210                 215                 220

Ala Arg Leu Ala Leu Thr Leu Ala Ala Ala Glu Ser Glu Arg Phe Val
225                 230                 235                 240

Arg Gln Gly Thr Gly Asn Asp Glu Ala Gly Ala Ala Asn Gly Pro Ala
                245                 250                 255

Asp Ser Gly Asp Ala Leu Leu Glu Arg Asn Tyr Pro Thr Gly Ala Glu
            260                 265                 270

Phe Leu Gly Asp Gly Gly Asp Val Ser Phe Ser Thr Arg Gly Thr Gln
        275                 280                 285

Asn Trp Thr Val Glu Arg Leu Leu Gln Ala His Arg Gln Leu Glu Glu
    290                 295                 300

Arg Gly Tyr Val Phe Val Gly Tyr His Gly Thr Phe Leu Glu Ala Ala
305                 310                 315                 320

Gln Ser Ile Val Phe Gly Gly Val Arg Ala Arg Ser Gln Asp Leu Asp
                325                 330                 335

Ala Ile Trp Arg Gly Phe Tyr Ile Ala Gly Asp Pro Ala Leu Ala Tyr
            340                 345                 350

Gly Tyr Ala Gln Asp Gln Glu Pro Asp Ala Arg Gly Arg Ile Arg Asn
```

-continued

```
              355                 360                 365
Gly Ala Leu Leu Arg Val Tyr Val Pro Arg Ser Ser Leu Pro Gly Phe
              370                 375                 380

Tyr Arg Thr Ser Leu Thr Leu Ala Ala Pro Glu Ala Ala Gly Glu Val
385                     390                 395                 400

Glu Arg Leu Ile Gly His Pro Leu Pro Leu Arg Leu Asp Ala Ile Thr
                405                 410                 415

Gly Pro Glu Glu Glu Gly Gly Arg Leu Glu Thr Ile Leu Gly Trp Pro
                420                 425                 430

Leu Ala Glu Arg Thr Val Val Ile Pro Ser Ala Ile Pro Thr Asp Pro
            435                 440                 445

Arg Asn Val Gly Gly Asp Leu Asp Pro Ser Ser Ile Pro Asp Lys Glu
        450                 455                 460

Gln Ala Ile Ser Ala Leu Pro Asp Tyr Ala Ser Gln Pro Gly Lys Pro
465                 470                 475                 480

Pro Lys Asp Glu Leu
                485
```

IL-4-FUSION FORMULATIONS FOR TREATMENT OF CENTRAL NERVOUS SYSTEM (CNS) TUMORS

CROSS REFERENCE TO RELATED APPLICATIONS

This application claims priority to U.S. Provisional Application No. 62/570,578, entitled "IL-4-FUSION FORMULATIONS FOR TREATMENT OF CENTRAL NERVOUS SYSTEM (CNS) TUMORS," filed Oct. 10, 2017, which is hereby incorporated by reference in its entirety.

SEQUENCE LISTING

The instant application contains a Sequence Listing which has been submitted electronically in text format and is hereby incorporated by reference in its entirety. Said text file, created on Nov. 4, 2024, is named 117802_5007_WO Sequence Listing_ST25.txt and is 4,568 bytes in size.

BACKGROUND OF THE INVENTION

First-line treatment for primary GB includes surgical resection of the bulk tumor to the maximal extent possible consistent with neurological preservation, followed by the Stupp protocol, which is established as the standard of care for newly diagnosed GB (Stupp et al., 2005). In the Stupp regimen, patients receive Temozolomide (Temodar®) concurrently with radiotherapy and then again following completion of radiotherapy. Temozolomide is approved for newly diagnosed GB concomitantly with radiotherapy and then as maintenance treatment (New Drug Application No. 021029; approval date: Aug. 11, 1999).

Newly diagnosed GB patients may also be treated with alternative chemotherapies, such as a nitrosourea regimen or insertion of a carmustine wafer (Gliadel®). Gliadel® is a biodegradable polymer wafer saturated with carmustine. Systemic toxicity usually associated with cytotoxic treatment may be reduced by implantation locally within the cranium (Westphal et al., 2006). Gliadel® is indicated for newly-diagnosed, high-grade malignant glioma as an adjunct to surgery and radiation as well as for recurrent GB as an adjunct to surgery (New Drug Application No. 020637; approval date: Feb. 25, 2003). It is implanted into the post-surgical cavity following complete tumor resection. Gliadel provides marginal increased survival of approximately 4-8 weeks (Westphal et al., 2003).

Using current treatment paradigms, most GB patients experience tumor recurrence/progression after standard first line treatment. Treatment options for patients with recurrent GB are very limited and the outcome is generally unsatisfactory. Specifically, chemotherapy regimens for recurrent or progressive GB have been unsuccessful, producing toxicity without benefit (Weller et al., 2013). This is mainly due to the lack of tissue specificity with resultant toxicity to normal tissues and consequently, a narrow therapeutic index. As overall survival remains dismal, novel anti-cancer modalities, with greater tumor specificity, more robust cytotoxic mechanisms and novel delivery techniques are needed for the treatment of recurrent GB.

Treatment options for patients with recurrent or progressive GB are very limited and positive long-term outcomes are rare. Drugs currently approved in the US for treatment of recurrent GB are Gliadel®, as mentioned above for first line treatment, and bevacizumab (Avastin®). In a Phase 3 study, placing a Gliadel implant directly into the tumor cavity after surgical resection of the tumor, 56% of recurrent GB treated subjects survived 6-month and the median survival was 26-weeks (Brem et al., 1995). However, the majority of patients with recurrent GB are not candidates for additional surgery, resulting in a large unmet need for this patient population (Weller et al., 2013).

Avastin® is an anti-angiogenic antibody that targets the vascular endothelial growth factor receptors (VEGF). It is indicated as a single agent for adult patients with recurrent GB (New Drug Application No. 125085; approval date: Feb. 26, 2004) but has not been shown to improve disease-related symptoms or survival. Avastin® was approved on the basis of objective response rate (ORR of 26%) endpoint (Genentech 2016; Cohen et al., 2009; Freidman et al., 2009). In 2013, Avastin® completed its confirmatory trial in newly diagnosed GB patients and did not meet its primary endpoint of overall survival. Based on the results of this trial, Genentech did not receive approval in the European Union (EU) for newly diagnosed GB; however, Avastin® remains indicated in the US and Japan for recurrent GB. Several studies have since compared efficacy with Avastin® or assessed combination approaches.

PRX 321 is a targeted immunotoxin consisting of a bioengineered circularly permuted version of interleukin-4 (cpIL-4), the binding domain, fused to a truncated version of a potent bacterial toxin-*Pseudomonas aeruginosa* exotoxin (PE) A, the catalytic domain (Kreitman et al., 1994). PRX 321 binds to interleukin-4 receptors (IL-4R) expressed on the surface of cells whereupon the entire complex is endocytosed. Following cleavage and activation by furin-like proteases found in high concentrations in the endosome of cancer cells, the catalytic domain of the truncated PE is released into the cytosol where it induces cell death via ADP-ribosylation of the Elongation Factor-2 and induction of apoptosis through caspase activation (Wedekind et al., 2001). Cells that do not express the IL-4R target do not bind to PRX 321 and are therefore, not subject to PE-mediated cell death. The PE portion was engineered to retain the catalytic domain but not the cell-binding domain.

Glioblastoma is a rapidly progressing and near-universally fatal cancer that is devastating to patients. This aggressive type of brain cancer is associated with substantial morbidity, often in the form of rapid deterioration of cognitive and psychomotor function, and a 1-year survival rate of approximately 25% following failure of front-line treatment (Lamborn et al., 2008). There is no currently effective treatment. PRX 321 represents a potential therapeutic advance. PRX 321 is a rationally designed targeted therapy with the potential to extend the survival of patients with GB. Adverse events associated with the administration and infusion of PRX 321, while serious, are similar to the effects of disease progression itself.

PRX 321 is a novel therapeutic that provides a targeted treatment approach whereby tumor cells are more sensitive to the toxic effects of the drug than normal cells. The target, IL-4R, is an ideal but under-exploited target for the development of cancer therapeutics, as it is frequently and intensely expressed on a wide variety of human carcinomas. Expression levels of IL-4R are low on the surface of healthy and normal cells, but increase several-fold on cancer cells. A majority of cancer biopsy and autopsy samples from adult and pediatric central nervous system (CNS) tumors, including recurrent GB biopsies, have been shown to over-express the IL-4R. There is little or no IL-4R expression in normal adult and pediatric brain tissue (Joshi, et al., 2001; see Table 2 of the reference). This differential expression of the IL-4R provides PRX 321 a wide therapeutic window (see Table 4 of the reference for $IC_{50}$ data). This feature alone makes PRX 321 an ideal candidate for the treatment of recurrent GB and other CNS tumors that over-express the IL-4R. Cells that do not express the IL-4R target do not bind to PRX 321 and are, therefore, not subject to PE-mediated effects.

As there remains a need in the art for the treatment of recurrent and/or progressive glioblastoma (GB), the PRX 321 formulations of the present invention meet this need.

BRIEF SUMMARY OF THE INVENTION

The present invention provides a method of treating a central nervous system (CNS) tumor in a subject, comprising administering to the subject a formulation comprising:
  i. an IL-4 targeted cargo protein in an artificial cerebral spinal fluid (CSF) solution, and
  ii. albumin,
wherein the formulation is co-administered with a surrogate tracer to a subject in need thereof.

In some embodiments of the method, the IL-4 targeted cargo protein comprises one or more cargo moieties.

In some embodiments of the method, the IL-4 targeted cargo protein comprises a toxin.

In some embodiments of the method, the toxin comprises a bacterial toxin, animal toxin, or plant toxin. In some embodiments of the method, the toxin comprises a pore-forming toxin. In some embodiments of the method, the pore-forming toxin comprises aerolysin or proaerolysin.

In some embodiments of the method, the plant toxin comprises bouganin or ricin.

In some embodiments of the method, the bacterial toxin comprises a toxin selected from the group consisting of *Pseudomonas* exotoxin, cholera toxin, or diphtheria toxin.

In some embodiments of the method, the IL-4 targeted cargo protein comprises pro-apoptosis member of the BCL-2 family selected from the group consisting of BAX, BAD, BAT, BAK, BIK, BOK, BID BIM, BMF, and BOK.

In some embodiments of the method, the IL-4 targeted cargo protein comprises PRX 321 (SEQ ID NO:1) or a derivative or variant thereof.

In some embodiments of the method, the surrogate tracer is magnetic resonance imaging (MRI) contrast agent. In some embodiments of the method, the surrogate tracer is a gadolinium-bound tracer. In some embodiments of the method, the surrogate tracer is selected from the group consisting of gadolinium-diethylenetriamine pentaacetic acid (Gd-DTPA) and gadolinium-bound albumin (Gd-albumin).

In some embodiments of the method, the albumin is human serum albumin.

In some embodiments of the method, the artificial CSF solution is Elliotts B® solution.

In some embodiments of the method, the IL-4 targeted cargo protein comprises in IL-4R antibody as the targeting moiety. In some embodiments of the method, the IL-4R antibody is a humanized antibody.

In some embodiments of the method, the IL-4 targeted cargo protein comprises a human cargo moiety selected from the group consisting of RNase A and perforin.

In some embodiments of the method, the IL-4 targeted cargo protein comprises a fusion protein In some embodiments of the method, the subject has a recurrent CNS tumor or a newly diagnosed CNS tumor. In some embodiments of the method, the subject has a recurrent or refractory CNS tumor. In some embodiments of the method, the subject is refractory.

In some embodiments of the method, the subject has an IL-4R positive CNS tumor.

In some embodiments of the method, the subject has an 06-methylguanine-methyltransferase (MGMT) positive CNS tumor.

In some embodiments of the method, the subject has furin positive CNS tumor.

In some embodiments of the method, the method further comprises determining whether the subject is refractory to radiation or chemotherapy; wherein if the subject is refractory it indicates that they will benefit from administration of the IL-4 targeted cargo protein.

In some embodiments of the method, the method further comprises administering chemotherapy or radiation therapy to the subject after administering the IL-4 targeted cargo protein, and/or surgically removing at least part of a tumor after administering the IL-4 targeted cargo protein.

In some embodiments of the method, the method further comprises administering chemotherapy or radiation therapy to the subject before administering the IL-4 targeted cargo protein, and/or surgically removing at least part of a tumor before administering the IL-4 targeted cargo protein.

In some embodiments of the method, the method further comprises administering chemotherapy or radiation therapy to the subject during treatment with the IL-4 targeted cargo protein, and/or administering the IL-4 targeted cargo protein during surgical removal of least part of a tumor in the subject, optionally wherein surgical resection is performed at 1 week, 2 weeks, 3 weeks, or 4 weeks post administration of the administering the IL-4 targeted cargo protein.

In some embodiments of the method, the further comprises administering to the subject an agonist that sensitizes the cancer stem cells prior to administering the IL-4 targeted cargo protein.

In some embodiments of the method, the IL-4 targeted cargo protein is administered intratumorally.

In some embodiments of the method, the intratumoral administration comprises intracranial administration.

In some embodiments of the method, the IL-4 targeted cargo protein is administered via an intracranial catheter.

In some embodiments of the method, the IL-4 targeted cargo protein is administered by convection-enhanced delivery (CED).

In some embodiments of the method, the IL-4 targeted cargo protein is administered as a single dose via convection-enhanced delivery (CED).

In some embodiments of the method, the IL-4 targeted cargo protein is administered as a single dose. In some embodiments of the method, the IL-4 targeted cargo protein is administered as a single dose of about 90 μg (1.5 μg/mL in 60 mL), about 240 μg (6 μg/mL in 40 mL), or about 300 μg (3 μg/mL in 100 mL). In some embodiments of the method, the IL-4 targeted cargo protein is administered at a dosage of 1.5 μg/mL in 60 mL. In some embodiments of the method, the IL-4 targeted cargo protein is administered at a dosage of 6 μg/mL in 40 mL. In some embodiments of the method, the IL-4 targeted cargo protein is administered at a dosage of 3 μg/mL in 100 mL. In some embodiments of the method, the IL-4 targeted cargo protein is administered as a single dose of about 1.5 μg/mL to about 3 μg/mL.

In some embodiments of the method, the IL-4 targeted cargo protein is administered as a single dose over 1 day, 2 days, 3 days, 4 days, 5 days, 6 days, 7 days, or 8 days.

In some embodiments of the method, the IL-4 targeted cargo protein is administered as 1, 2, 3, 4, or 5 infusions.

In some embodiments of the method, the IL-4 targeted cargo protein is administered according to any of the preceding claims, then discontinuing the administration for from about 1 day to about 8 days, optionally discontinuing the administration for 1 day, 2 days, 3 days, 4 days, 5 days, 6 days, 7 days, or 8 days, followed by administration according to any of the preceding claims, and repeating this pattern of administration and discontinuance of administration for as long as necessary for treatment of the CNS tumor.

In some embodiments of the method, the CNS tumor is selected from the group consisting of glioma, glioblastoma, astrocytoma, medulloblastoma, craniopharyogioma, ependymoma, pinealoma, hemangioblastoma, acoustic neuroma, oligodendroglia, menangioma, meningioma, neuroblastoma, and retinoblastoma. In some embodiments of the method, the CNS tumor is a glioblastoma. In some embodiments of the method, the CNS tumor is a recurrent or refractory glioblastoma.

In some embodiments of the method, the IL-4 targeted cargo protein is administered via one or more intracranial catheters. In some embodiments of the method, the IL-4 targeted cargo protein is administered through the catheter with a flow rate of about 5 µL/min/catheter to about 20 µL/min/catheter. In some embodiments of the method, the IL-4 targeted cargo protein is administered through the catheter with a flow rate of about 15 µL/min/catheter. In some embodiments of the method, the IL-4 targeted cargo protein is administered through the catheter at a concentration of 1.5 µg/mL and with a flow rate of about 15 µL/min/catheter. In some embodiments of the method, 1 to 3 catheters are used for administration.

In some embodiments of the method, the IL-4 targeted cargo protein is PRX 321.

The present invention also provides a unit dosage formulation for the treatment of a CNS tumor comprising:
 i. an IL-4 targeted cargo protein formulated in an artificial cerebral spinal fluid (CSF) solution;
 ii. albumin; and
 iii. a surrogate tracer,
wherein the unit dosage formulation is formulated for intracranial administration to the CNS tumor through one or more intracranial catheters.

In some embodiments of the unit dosage formulation, the IL-4 targeted cargo protein is administered as a single dose of about 90 µg (1.5 µg/mL in 60 mL), about 240 µg (6 µg/mL in 40 mL), or about 300 µg (3 µg/mL in 100 mL). In some embodiments of the unit dosage formulation, the IL-4 targeted cargo protein is administered at a dosage of 1.5 µg/mL in 60 mL. In some embodiments of the unit dosage formulation, the IL-4 targeted cargo protein is administered at a dosage of 6 µg/mL in 40 mL. In some embodiments of the unit dosage formulation, the IL-4 targeted cargo protein is administered at a dosage of 3 µg/mL in 100 mL. In some embodiments of the unit dosage formulation, the IL-4 targeted cargo protein is administered as a single dose of about 1.5 µg/mL to about 3 µg/mL. In some embodiments of the unit dosage formulation, the IL-4 targeted cargo protein is administered through the catheter via a flow rate of about 5 µL/min/catheter to about 20 µL/min/catheter. In some embodiments of the unit dosage formulation, IL-4 targeted cargo protein is administered through the catheter with a flow rate of about 15 µL/min/catheter. In some embodiments of the unit dosage formulation, the IL-4 targeted cargo protein is administered through the catheter at a concentration of 1.5 µg/mL and with a flow rate of about 15 µL/min/catheter. In some embodiments of the unit dosage formulation, 1 to 3 catheters are used for administration.

In some embodiments of the unit dosage formulation, the unit dosage formulation of IL-4 targeted cargo protein is formulated for administered according to any of the preceding claims, then discontinuing the administration for from about 1 day to about 8 days, optionally discontinuing the administration for 1 day, 2 days, 3 days, 4 days, 5 days, 6 days, 7 days, or 8 days, followed by administration according to any of the preceding claims, and repeating this pattern of administration and discontinuance of administration for as long as necessary for treatment of the CNS tumor.

In some embodiments of the unit dosage formulation, the unit dosage formulation of IL-4 targeted cargo protein is formulated for administered according to any of the preceding claims, then discontinuing the administration for from about 1 day to about 8 days, optionally discontinuing the administration for 1 day, 2 days, 3 days, 4 days, 5 days, 6 days, 7 days, or 8 days, followed by administration according to any of the preceding claims, and repeating this pattern of administration and discontinuance of administration for as long as necessary for treatment of the CNS tumor.

In some embodiments the invention provides a formulation comprising an IL-4 targeted cargo protein in an artificial cerebral spinal fluid (CSF) solution, albumin, and a surrogate tracer, for use in the treatment of a central nervous system (CNS) tumor.

In some embodiments the invention provides a formulation comprising PRX 321 in an artificial cerebral spinal fluid (CSF) solution, albumin, and a surrogate tracer, for use in the treatment of a glioma.

In some embodiments the invention provides a formulation comprising PRX 321 in human serum albumin and a surrogate tracer, for use in the treatment of a central nervous system (CNS) tumor.

In some embodiments the invention provides a formulation comprising an IL-4 targeted cargo protein in an artificial cerebral spinal fluid (CSF) solution, albumin, and a gadolinium bound tracer, for use in the treatment of a central nervous system (CNS) tumor, for example a glioma.

In some embodiments the invention provides a formulation comprising PRX 321 in human serum albumin, and a gadolinium bound tracer, for use in the treatment of a central nervous system (CNS) tumor, for example a glioma.

In some embodiments of the formulation, the use is according to the method recited herein.

BRIEF DESCRIPTION OF THE DRAWINGS

FIG. 2: PRX 321 sequence, SEQ ID NO: 1 as well as a schematic representation of the structure (A) and amino acid sequence (B) of an exemplary IL-4 targeted cargo protein, a circularly permuted IL-4-*Pseudomonas* toxin, PRX 321 (SEQ ID NO: 1). Disulfide bonds are indicated on the drawing.

FIG. 3: Optimized CED Technology Improves Drug Distribution.

FIG. 6: Results for PRX 321 related TEAEs and SAEs-CNS effects.

FIG. 7: Safety for PRX 321-05—AEs≥Gd 3.

FIG. 8: Overview of case study 1 for a 74-year old male.

FIG. 9: Case study 1. A) tumor mapping MRI picture. B) Tumor vs. final distribution of drug MRI picture. C) Calculation of drug distribution at end of infusion (by Gad) MRI picture. D) Estimate of coverage MRI picture. Tumor Volume—1.5 cm³; Tumor Diameter—1.8 cm; Vi—15 cm³; Vd of Gad—30 cm³; VD/Vi ratio—2; Vd/tumor volume—20; and Tumor coverage*—70% (*initial estimate).

FIG. 10: Overview of case study 1 for a 58-year old male.

FIG. 14: Case study 2 A) Coverage at the end of infusion MRI picture. B) estimate of coverage MRI picture. Tumor Volume—1.9 cm³; Tumor Diameter—2.9 cm; Vi—17 cm³; Vd of Gad—30 cm³; VD/Vi ratio—1.8; Vd/tumor volume—20; and Tumor coverage*—90% (*initial estimate).

DETAILED DESCRIPTION OF THE INVENTION

I. Definitions

Abbreviations and Terms

Figure 1:
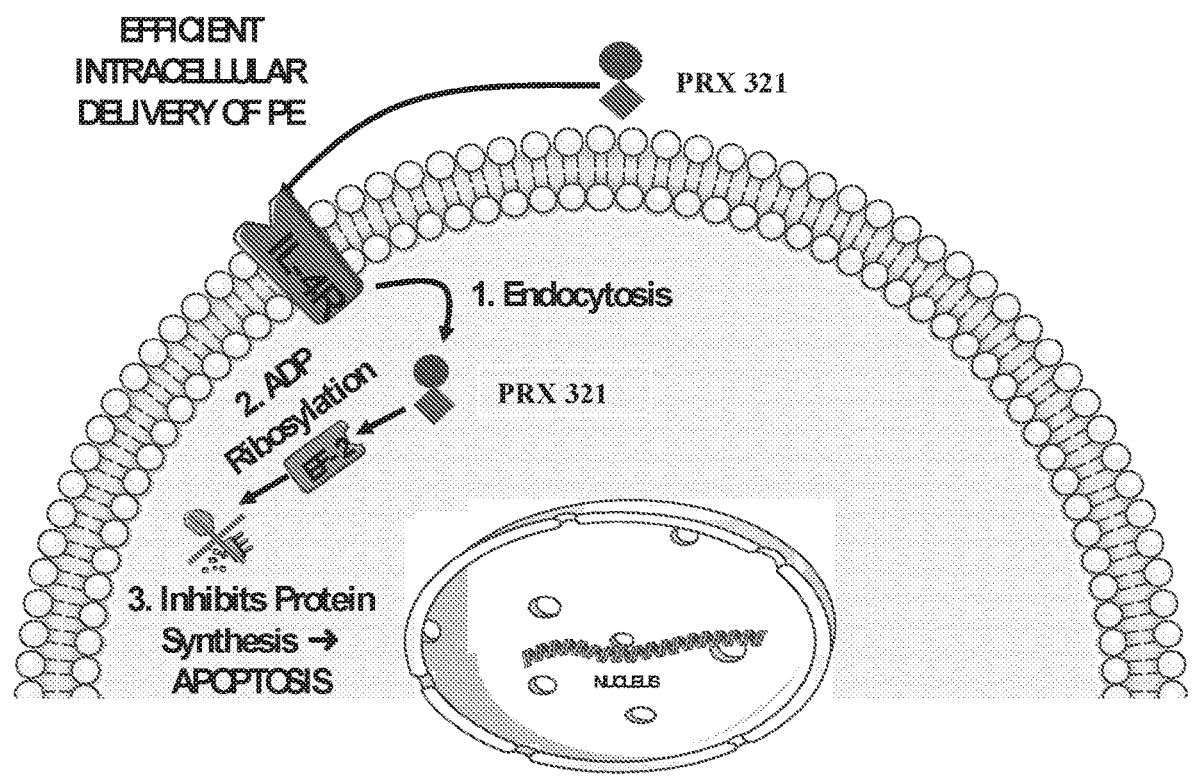
FIG. 1: Schematic of the PRX 321 mechanism of action.
Figure 4:
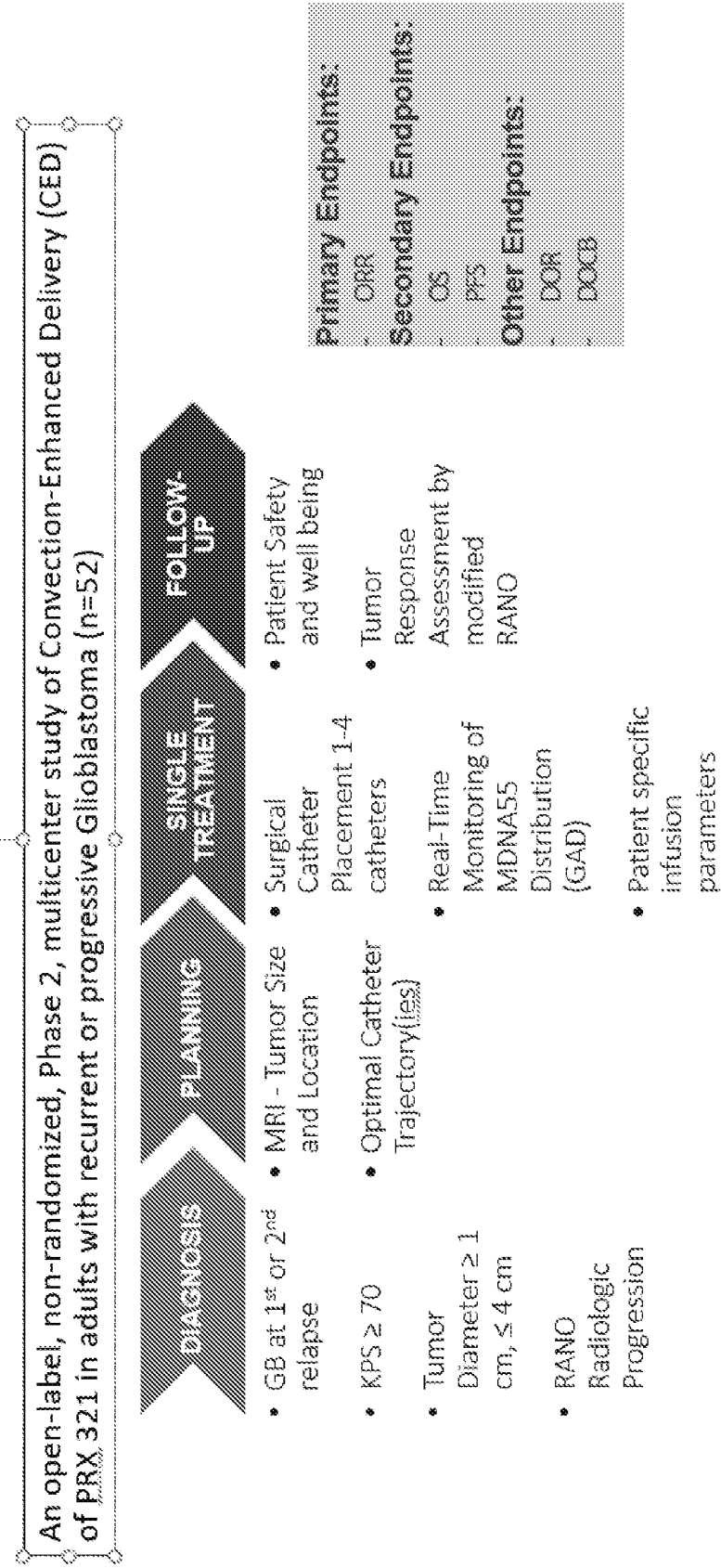
FIG. 4: Diagram of the Phase-2 Study of High Flow-rate CED in rGB procedure.
Figure 5:
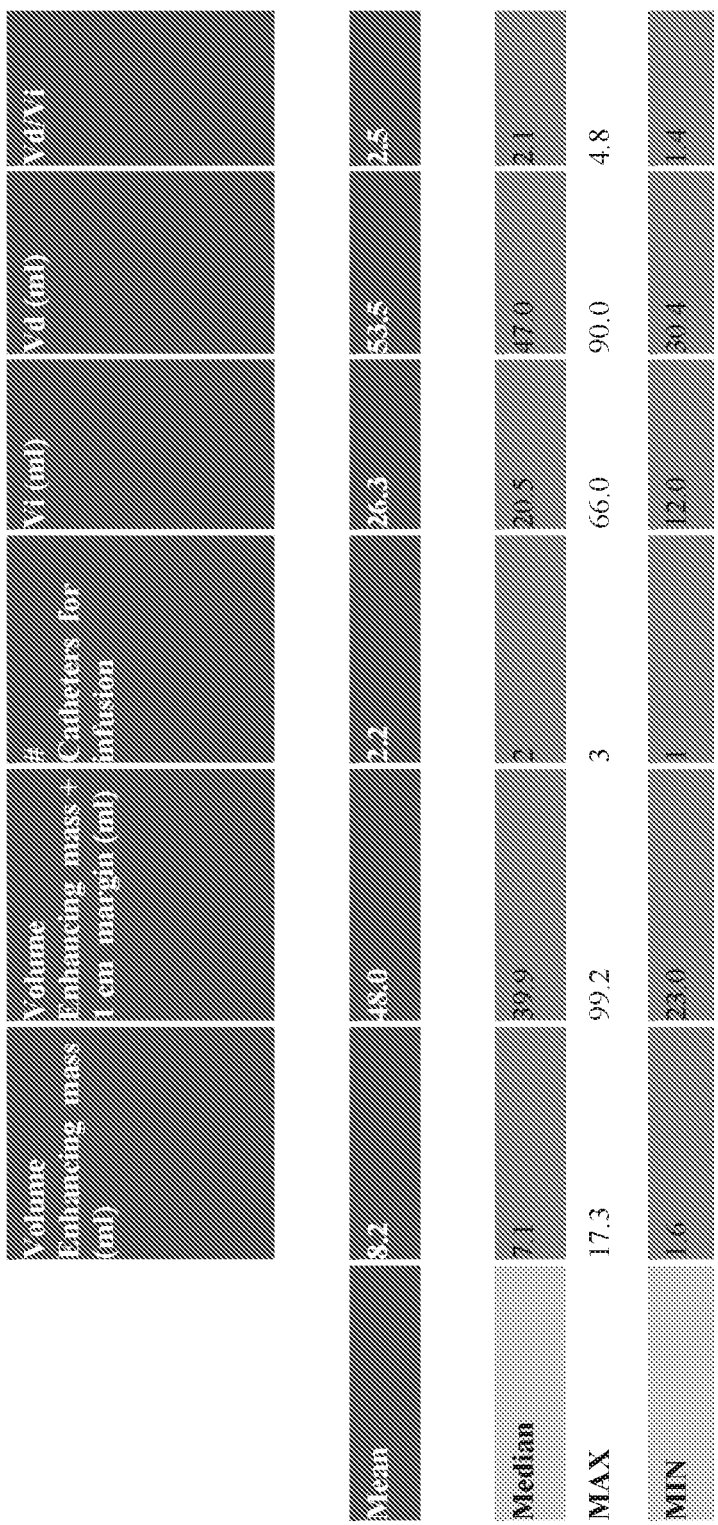
FIG. 5: Planned and Infused Volumes for PRX 321. Summary of interim results. The analysis was conducted for the first 6 patients.
Figure 11:
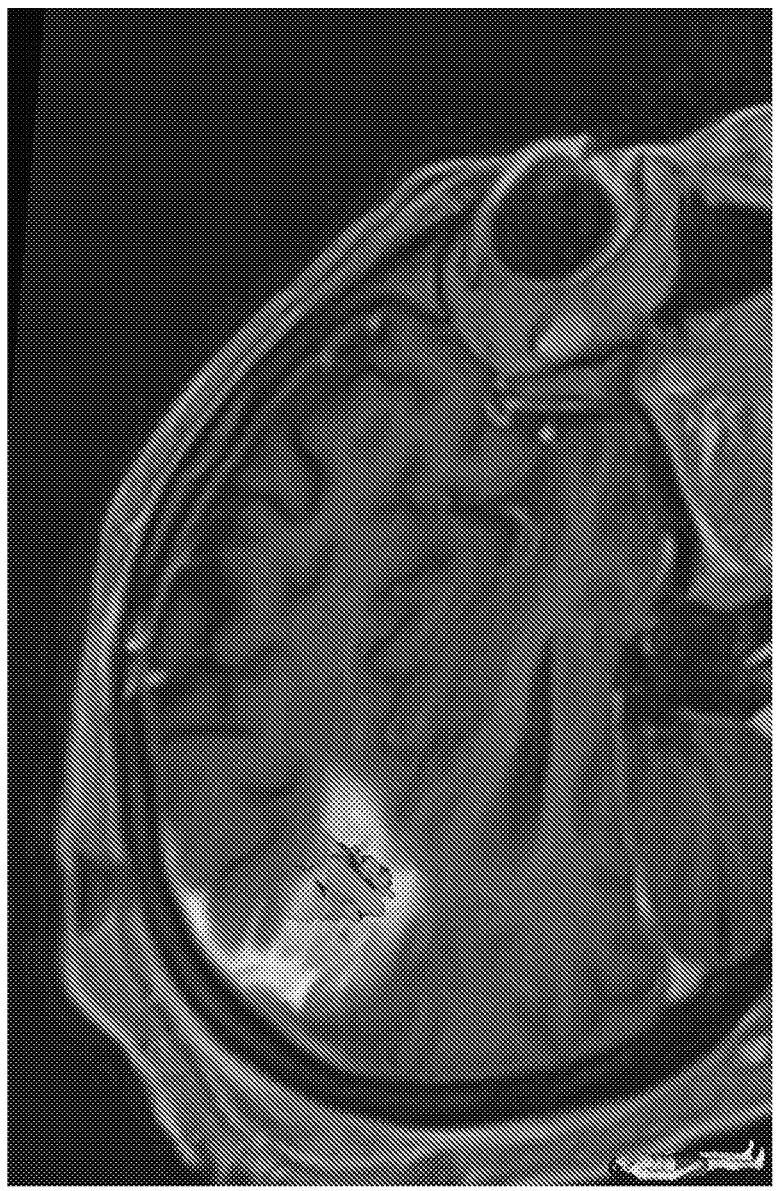
FIG. 11: Case study 2 tumor mapping MRI picture.
Figure 12:
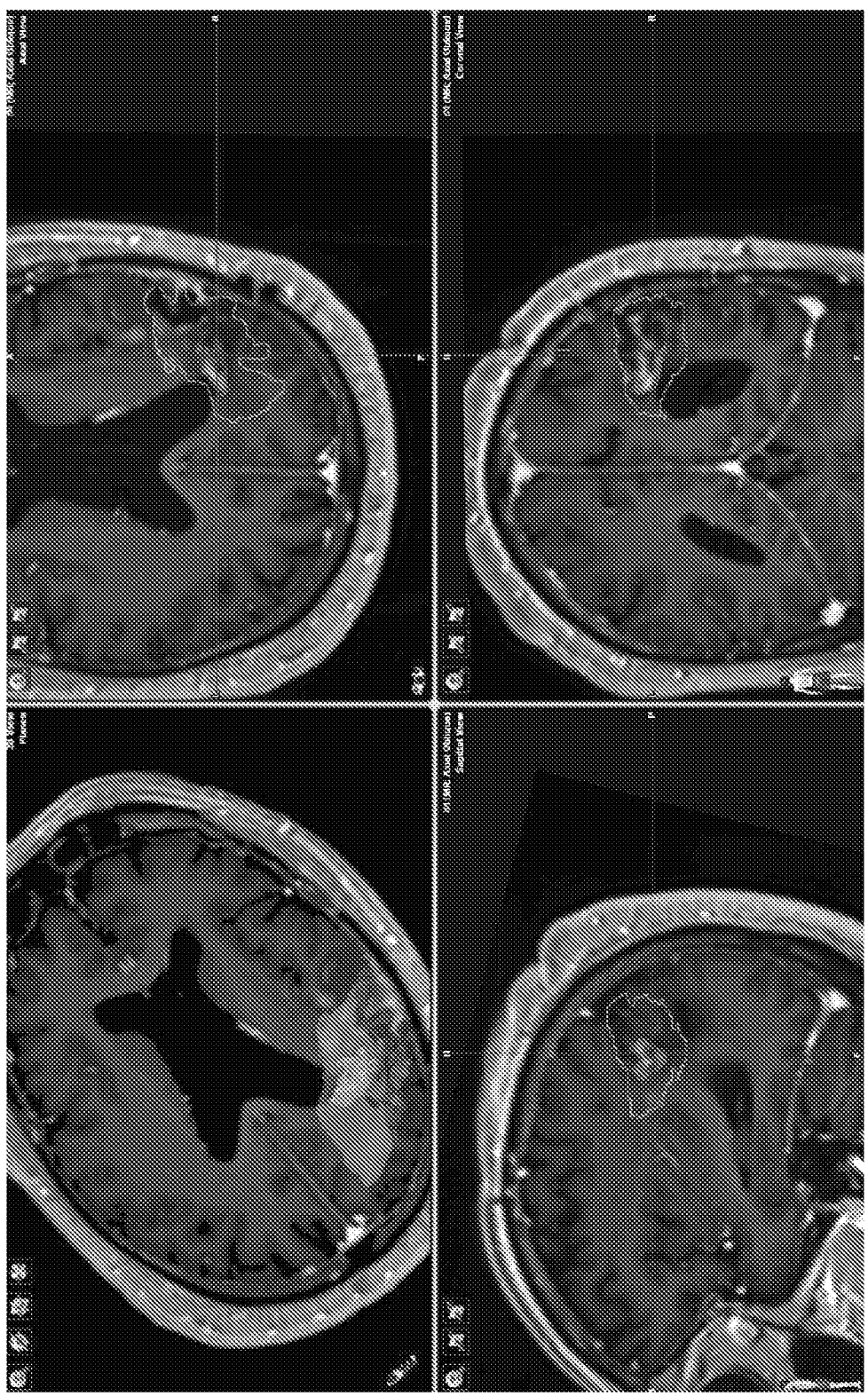
FIG. 12: Case study 2 evaluation of infusion MRI picture.
Figure 13:
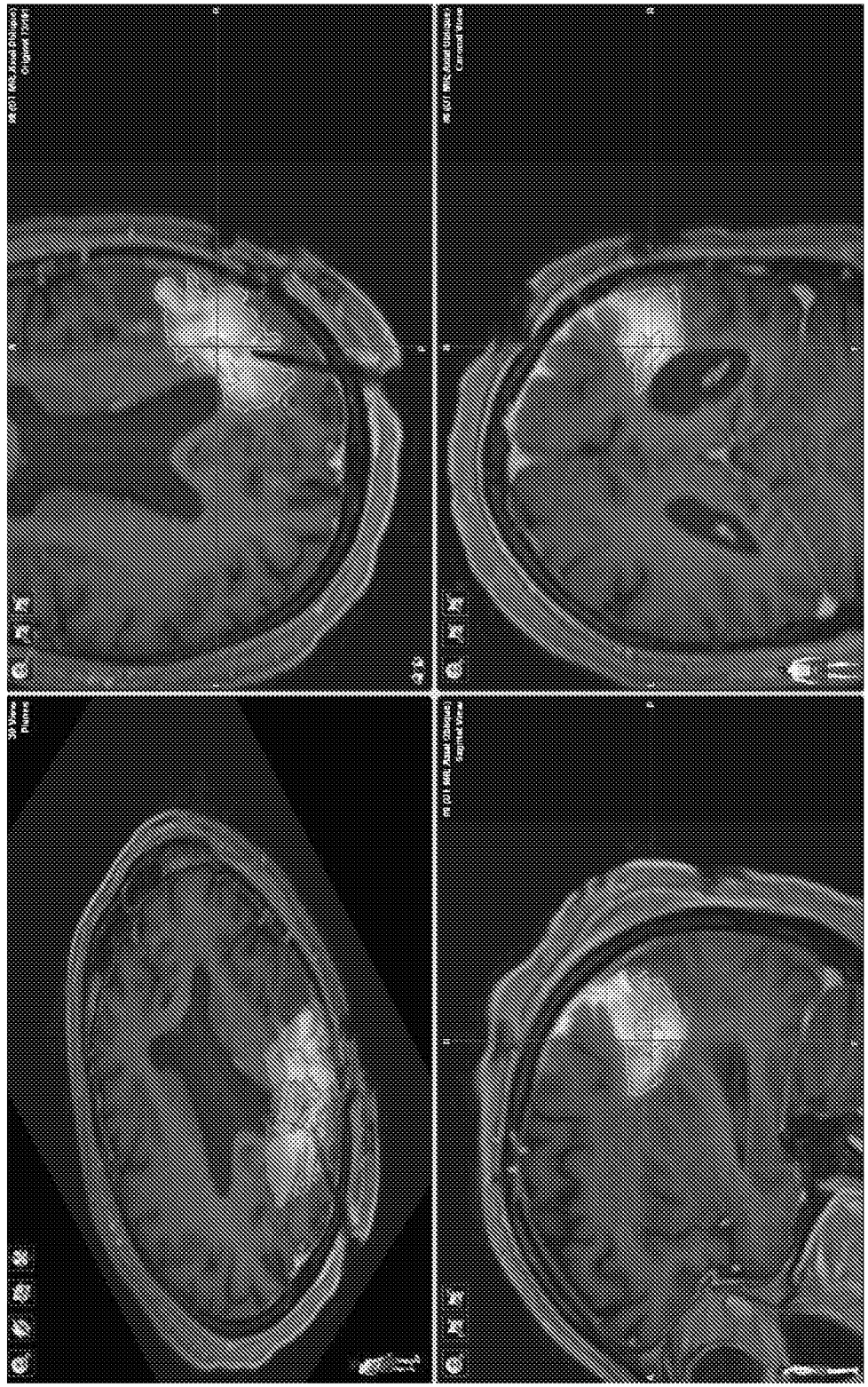
FIG. 13: Case study 2 evaluation of infusion MRI picture.
Figure 15:
FIG. 15: Coverage of Targeted Area. Summary of results: analysis was conducted for the first 6 patients.

| | |
|---|---|
| PA | Proaerolysin |
| BAD | BCL2-associated agonist of cell death |
| BAX | BCL2-associated X protein |
| EGF | Epidermal growth factor |
| EpCAM | Epithelial protein cell adhesion molecule |
| GMCSF | Granulocyte-macrophage colony-stimulating factor |
| IL-4 | Interleukin-4 |
| IL-13 | Interleukin-13 |
| PSMA | Prostate specific membrane antigen |

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a IL-4 targeted cargo protein" includes single or plural IL-4 targeted cargo proteins and is considered equivalent to the phrase "comprising at least about one IL-4 targeted cargo protein." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs.

Accession Numbers: Reference numbers assigned to various nucleic acid and amino acid sequences in the NCBI database (National Center for Biotechnology Information) that is maintained by the National Institute of Health, U.S.A. The accession numbers listed in this specification are herein incorporated by reference as provided in the database as of the date of filing this application.

Administration: Providing or giving a subject an agent, such as a composition that includes a IL-4 targeted cargo protein. Exemplary routes of administration include, but are not limited to, oral, injection (such as subcutaneous, intramuscular, intradermal, intraperitoneal, intratumoral and intravenous), sublingual, rectal or transrectal, transdermal, intranasal, vaginal, cervical, and inhalation routes. In specific examples, intratumoral includes local, regional, focal, or convection enhanced delivery. In other specific examples, administration includes transurethral or transperineal administration. In one example, surrogate magnetic resonance imaging tracers (e.g., gadolinium-bound albumin (Gd-albumin)) can be administered in combination with the IL-4 targeted cargo protein to determine if the IL-4 targeted cargo protein is delivered to a tumor, such as a brain tumor, safely at therapeutic doses while monitoring its distribution in real-time (see for example, Murad et al., Clin. Cancer Res. 12 (10): 3145-51 2006).

Antibody: Immunoglobulin molecules and immunologically active portions of immunoglobulin molecules, that is, molecules that contain an antigen binding site that specifically binds (immunoreacts with) an epitope, such as an epitope displayed by cancer cells and/or cancer stem cells. Antibodies include monoclonal antibodies, polyclonal antibodies, as well as humanized antibodies. Antibodies also include affibodies. Affibodies mimic monoclonal antibodies in function but are based on Protein A. Affibodies can be engineered as high-affinity ligands for binding to a targeting moiety.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the VL, VH, CL and CHI domains; (ii) an Fd fragment consisting of the VH and CHI domains; (iii) an Fv fragment consisting of the VL and VH domains of a single arm of an antibody (scFv) and scFv molecules linked to each other to form a bivalent dimer (diabody) or trivalent trimer (triabody); (iv) a dAb fragment (Ward et al., Nature 341:544-546, 1989) which consists of a VH domain; (v) an isolated complimentarity determining region (CDR); and (vi) a F(ab')₂ fragment, a bivalent fragment comprising two Fab fragments linked by a disulfide bridge at the hinge region.

Methods of producing polyclonal and monoclonal antibodies are known to those of ordinary skill in the art, and many antibodies are available. See, e.g., Coligan, Current Protocols in Immunology Wiley/Greene, N.Y., 1991; and Harlow and Lane, Antibodies: A Laboratory Manual Cold Spring Harbor Press, NY, 1989; Stites et al., (eds.) Basic and Clinical Immunology (4th ed.) Lange Medical Publications, Los Altos, Calif., and references cited therein; Goding, Monoclonal Antibodies: Principles and Practice (2d ed.) Academic Press, New York, N.Y., 1986; and Kohler and Milstein, Nature 256:495-497, 1975. Other suitable techniques for antibody preparation include selection of libraries of recombinant antibodies in phage or similar vectors. See, Huse et al., Science 246:1275-1281, 1989; and Ward et al., Nature 341:544-546, 1989.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Faoulkner et al., Nature 298:286, 1982; Morrison, J. Immunol. 123: 793, 1979; Morrison et al., Ann Rev. Immunol 2:239, 1984). Detailed methods for preparation of chimeric (humanized) antibodies can be found in U.S. Pat. No. 5,482,856. Additional details on humanization and other antibody production and engineering techniques can be found in Borrebaeck (ed), Antibody Engineering, 2nd Edition Freeman and Company, NY, 1995; McCafferty et al., Antibody Engineering, A Practical Approach, IRL at Oxford Press, Oxford, England, 1996, and Paul Antibody Engineering Protocols Humana Press, Towata, N.J., 1995.

In some examples, an antibody specifically binds to a target protein (e.g., a cell surface receptor such as an IL4 receptor) with a binding constant that is at least $10^3$ $M^{-1}$ greater, $10^4$ $M^{-1}$ greater or $10^5$ $M^{-1}$ greater than a binding constant for other molecules in a sample. In some examples, a specific binding reagent (such as an antibody (e.g., monoclonal antibody) or fragments thereof) has an equilibrium constant ($K_d$) of 1 nM or less. For example, a specific binding agent may bind to a target protein with a binding affinity of at least about $0.1 \times 10 \cdot \sup.^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M. $K_d$ values can, for example, be determined by competitive ELISA (enzyme-linked immunosorbent assay) or using a surface-plasmon resonance device such as the Biacore T100, which is available from Biacore, Inc., Piscataway, N.J.

Binds or binding: The association between two or more molecules, wherein the two or more molecules are in close physical proximity to each other, such as the formation of a complex. An exemplary complex is a receptor-ligand pair or an antibody-antigen pair. Generally, the stronger the binding of the molecules in a complex, the slower their rate of dissociation. Specific binding refers to a preferential binding between an agent and a specific target. For example, specific binding refers to when a IL-4 targeted cargo protein that includes a targeting moiety specific for a cancer stem cell antigen binds to the cancer stem cell, but does not significantly bind to other cells that do not display the target in close proximity to the cancer stem cell. Such binding can be a specific non-covalent molecular interaction between the ligand and the receptor. In a particular example, binding is assessed by detecting cancer stem cell growth inhibition using one of the methods described herein after the IL-4 targeted cargo protein has been contacted with the cancer stem cell.

Such interaction is mediated by one or, typically, more noncovalent bonds between the binding partners (or, often, between a specific region or portion of each binding partner). In contrast to non-specific binding sites, specific binding sites are saturable. Accordingly, one exemplary way to characterize specific binding is by a specific binding curve. A specific binding curve shows, for example, the amount of one binding partner (the first binding partner) bound to a fixed amount of the other binding partner as a function of the first binding partner concentration. As the first binding partner concentration increases under these conditions, the amount of the first binding partner bound will saturate. In another contrast to non-specific binding sites, specific binding partners involved in a direct association with each other (e.g., a protein-protein interaction) can be competitively removed (or displaced) from such association (e.g., protein complex) by excess amounts of either specific binding partner. Such competition assays (or displacement assays) are very well known in the art.

Cancer: Malignant neoplasm that has undergone characteristic anaplasia with loss of differentiation, increased rate of growth, invasion of surrounding tissue, and is capable of metastasis. Residual cancer is cancer that remains in a subject after any form of treatment given to the subject to reduce or eradicate a cancer and recurrent cancer is cancer that recurs after such treatment. Metastatic cancer is a cancer at one or more sites in the body other than the site of origin of the original (primary) cancer from which the metastatic cancer is derived. In the case of a metastatic cancer originating from a solid tumor, one or more (for example, many) additional tumor masses can be present at sites near or distant to the site of the original tumor. The phrase "disseminated metastatic nodules" or "disseminated metastatic tumors" refers to a plurality (typically many) metastatic tumors dispersed to one or more anatomical sites. For example, disseminated metastatic nodules within the peritoneum (that is a disseminated intraperitoneal cancer) can arise from a tumor of an organ residing within or outside the peritoneum, and can be localized to numerous sites within the peritoneum. Such metastatic tumors can themselves be discretely localized to the surface of an organ, or can invade the underlying tissue.

Cargo Moiety: A peptide (e.g., protein fragment or full length protein) or other molecule that can function to significantly reduce or inhibit the growth of a cancer stem cell. In some examples a cargo moiety can trigger cell death (e.g., apoptosis). Exemplary cargo moieties include toxins, such as toxins derived from plants, microorganisms, and animals. In other examples, cargo moieties are proteins that normally contribute to the control of cell life cycles, for example cargo moieties can be any protein that triggers cell death, such as via apoptotic or non-apoptotic pathways. In some examples, the cargo moiety is not a protein, but another molecule that can function to significantly reduce or inhibit the growth of a cancer stem cell, such as thapsigargin. In some examples, a cargo moiety is activated by a tumor-associated protease, such as PSA. Exemplary cargo moieties, and exemplary GenBank accession numbers, are provided in Table 1, below. In addition to native cargo sequences, variant sequences can also be used, such as mutant sequences with greater biological activity than that of the native sequence.

TABLE 1

Exemplary cargo moiety sequences

| Cargo Moiety | Accession Numbers* |
|---|---|
| Aerolysin | ABR14715.1; ABR14714.1 |
| Proaerolysin | AAA21938.1; P09167.2; U.S. Pat. No. 7,282,476 (proaerolysin sequences therein herein incorporated by reference) |
| Bouganin | AAL35962 and SEQ ID NO: 9 in U.S. Pat. No. 6,737,511, as well as variant sequences provided in U.S. Pat. No. 7,339,031 and WO 2005/090579 (bouganin sequences therein herein incorporated by reference) |
| Pseudomonas exotoxin | 1IKP A; AAB59097.1; AAF90003.1 (also see SEQ ID NO: 1 of U.S. Pat. No. 6,011,002) |
| Bcl-2 pro-apoptotic proteins such as BAD and BAX | BAD: CAG46757; AAH01901.1; CAG46733.1; and sequences provided in U.S. Pat. No. 6,737,511 BAX: CAE52909.1; AAO22992.1; EAW52418.1 |
| Cholera toxin | BAA06291.1; ACF35010.1; BAA06288.1; as well as variant sequences provided in U.S. patent application Ser. No. 61/058,872 (variant cholera toxin sequences therein herein incorporated by reference) |
| Ribonuclease A | BAA05124.1; NP_937877.1; NP_115961.2; Q5GAN4.1; and sequences provided in PCT Publication No. WO2007/041361 (rapLR1 sequences therein herein incorporated by reference) |

*GenBank Numbers are herein incorporated by reference, as well as their corresponding nucleic acid sequences.

Contact or contacting: Refers to the relatively close physical proximity of one object to another object. Generally, contacting involves placing two or more objects in close physical proximity to each other to give the objects and opportunity to interact. For example, contacting a IL-4 targeted cargo protein with a cancer stem cell can be accomplished by placing the IL-4 targeted cargo protein (which can be in a solution) in proximity to the cell, for example by injecting the IL-4 targeted cargo protein into a subject having the cancer. Similarly, a IL-4 targeted cargo protein can be contacted with a cell in vitro, for example by adding the IL-4 targeted cargo protein to culture media in which the cell is growing.

Decrease: To reduce the quality, amount, or strength of something. In one example, a therapy (such as treatment with a IL-4 targeted cargo protein) decreases a cancer stem cell population (such as by decreasing the size of a tumor, the volume of a tumor, the metastasis of a tumor, the number of cancer cells and/or cancer stem cells, or combinations thereof), or one or more symptoms associated with cancer, for example as compared to the response in the absence of the therapy. In a particular example, a therapy decreases the size of a tumor, volume of a tumor, number of cancer cells and/or cancer stem cells, or the metastasis of a cancer, or combinations thereof, subsequent to the therapy, such as a decrease of at least about 10%, at least about 20%, at least about 50%, or even at least about 90%. Such decreases can be measured using the methods disclosed herein.

Diagnose: The process of identifying a medical condition or disease, for example from the results of one or more diagnostic procedures. In particular examples, includes determining the prognosis of a subject (e.g., likelihood of survival over a period of time, such as likelihood of survival in 6-months, 1-year, or 5-years). In a specific example, cancer is diagnosed by detecting the presence of a cancer stem cell in a sample using one or more of the targets on the cancer stem cell surface. For example, diagnoses can include determining the particular stage of cancer or the presence of a site of metastasis.

Linker: A molecule used to connect one or more agents to one or more other agents. For example, a linker can be used to connect one or more cargo moieties to one or more targeting moieties. Particular non-limiting examples of linkers include dendrimers, such as synthetic polymers, peptides, proteins and carbohydrates. Linkers additionally can contain one or more protease cleavage sites or be sensitive to cleavage via oxidation and/or reduction.

Pharmaceutically acceptable carriers: The term "pharmaceutically acceptable carriers" refers to pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic or diagnostic agents, such as one or more of the IL-4 targeted cargo protein molecules provided herein.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Pharmaceutical agent or drug: A chemical compound or composition capable of inducing a desired therapeutic effect when administered to a subject, alone or in combination with another therapeutic agent(s) or pharmaceutically acceptable carriers. In a particular example, a pharmaceutical agent (such as one that includes a IL-4 targeted cargo protein) treats a cancer, for example by reducing the size of the tumor (such as the volume or reducing the number of cancer cells and/or cancer stem cells), reducing metastasis of the cancer, or combinations thereof.

Recombinant: A recombinant molecule (such as a recombinant nucleic acid molecule or protein) has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. A recombinant protein is one that results from expressing a recombinant nucleic acid encoding the protein. IL-4 targeted cargo proteins of the present disclosure are generally recombinant.

Sample: Biological specimens such as samples containing biomolecules, such as nucleic acid molecules, proteins, or both. Exemplary samples are those containing cells or cell lysates from a subject, such as those present in peripheral blood (or a fraction thereof such as serum), urine, saliva, tissue biopsy, cheek swabs, surgical specimen, fine needle aspirates, cervical samples, and autopsy material. In a specific example, a sample is obtained from a tumor (for example a section of tissue from a biopsy), which can include tumor cells that are both non-cancer cells and/or cancer stem cells and cancer cells and/or cancer stem cells. In some embodiments, the tumor sample is from a central nervous system (CNS) tumor.

Sequence identity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN can be used to compare nucleic acid sequences, while BLASTP can be used to compare amino acid sequences. To compare two nucleic acid sequences, the options can be set as follows: -i is set to a file containing the first nucleic acid sequence to be compared (such as C: \seq1.txt); —j is set to a file containing the second nucleic acid sequence to be compared (such as C: \seq2.txt); —p is set to blastn; —o is set to any desired file name (such as C: \output.txt); —q is set to—1; —r is set to 2; and all other options are left at their default setting. For example, the following command can be used to generate an output file containing a comparison between two sequences: C: \B12seq—i c: \seq1.txt—j c: \seq2.txt—p blastn—o c: \output.txt—q—1—r 2.

To compare two amino acid sequences, the options of B12seq can be set as follows: —i is set to a file containing the first amino acid sequence to be compared (such as C: \seq1.txt); —j is set to a file containing the second amino acid sequence to be compared (such as C: \seq2.txt); —p is set to blastp; —o is set to any desired file name (such as C: \output.txt); and all other options are left at their default setting. For example, the following command can be used to generate an output file containing a comparison between two amino acid sequences: C: \B12seq—i c: \seq1.txt —j c: \seq2.txt—p blastp—o c: \output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166/1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a cargo protein or targeting moiety provided herein.

When aligning short peptides (fewer than around 30 amino acids), the alignment is be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, 99% sequence identity to a cargo moiety or targeting moiety provided herein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

Subject: Living multi-cellular vertebrate organisms, a category that includes human and non-human mammals (such as laboratory or veterinary subjects).

IL-4 targeted cargo protein: Any protein that binds specifically to a cancer stem cell and reduces or inhibits cancer stem cell growth, or kills cancer cells and/or cancer stem cells. In some examples, IL-4 targeted cargo proteins can target both cancer cells and/or cancer stem cells and tumor (e.g., cancer) cells that are not cancer cells and/or cancer stem cells. IL-4 targeted cargo proteins include a targeting moiety and a cargo moiety, the targeting moiety specifically binds with the cancer stem cell and the cargo moiety significantly reduces or inhibits the growth of the cancer stem cell or kills cancer stem cells. In some examples the cargo moiety causes the death of the cancer stem cell that it is associated with. Because in some examples the cargo moiety is not a protein, such as a chemotherapeutic agent, and in some examples the targeting moiety is not a protein, the IL-4 targeted cargo protein in some examples is not actually a protein.

Targeting moiety: Any compound that binds to a molecule (herein referred to as a target) displayed by a cancer stem cell, for example a targeting moiety can be an antibody that binds to a target (e.g., receptor), a ligand (e.g., a cytokine or growth factor) that binds to a receptor, a permuted ligand that binds to a receptor, or a peptide sequence sensitive to cleavage by a tumor-associated protease. In some examples, a targeting moiety is activated by a tumor-associated protease, such as PSA. Typically, targeting moieties selectively bind to one type of cell displaying a target more effectively than they bind to other types of cells that do not display the target. Targeting moieties can be chosen to selectively bind to subsets of tumor cells, such as cancer cells and/or cancer stem cells. Targeting moieties include specific binding agents such as antibodies, natural ligands of the target on the stem cell, such as IL-4, derivatives of such natural ligands, and immunoglobulin A. In some examples, the targeting moiety is not biologically active (e.g., cannot activate a receptor), but retains the ability to bind to the target and thus direct the IL-4 targeted cargo protein to the appropriate cells.

Table 2 provides information relating to the sequences of exemplary natural ligands as well as other antigens that can be used as targeting moieties. In some examples, circular permuted ligands, such as circular permuted IL-4, can be used to bind cancer cells and/or cancer stem cells. As additional research is performed, new cancer stem cell specific targets will be identified. These additional markers can be used as targets for binding to targeting moieties and IL-4 targeted cargo proteins can be made to inhibit the growth of (or kill) cancer cells and/or cancer stem cells displaying such ligands. One of ordinary skill in the art will appreciate that once a marker is known, standard methods of making antibodies to the identified marker can be used to make targeting moieties specific for the cancer stem cell marker, thus, allowing for the development of a specific IL-4 targeted cargo protein.

TABLE 2

Exemplary targeting moiety sequences

| Receptor or Antigen to be Targeted | Accession Numbers* |
|---|---|
| IL-4 | AAH70123; CAA57444.1; AAH67515.1 (also see SEQ ID NO: 2 and various circularly permuted ligands described in U.S. Pat. No. 6,011,002) |
| PRX 321 | SEQ ID NO: 1 (PRX 321 is a fusion toxin comprising a genetically engineered circularly permuted interleukin-4 (cpIL-4) fused to a modified version of the *Pseudomonas aeruginosa* exotoxin A (PE)) |
| IL-13 | AAH96141.2; AAH96138.1; AAH96139.1 |

*GenBank Numbers are herein incorporated by reference, as well as their corresponding nucleic acid sequences.

Targets on cancer cells and/or cancer cells and/or cancer stem cells include small molecules displayed on the surface of cancer cells and/or cancer stem cells. Antibodies directed to such targets can be used as targeting moieties as well as the natural ligands of the targets and derivatives thereof.

Therapeutically effective amount: An amount of an agent that alone, or together with a pharmaceutically acceptable carrier or one or more additional therapeutic agents, induces the desired response. A therapeutic agent, such as a IL-4 targeted cargo protein, is administered in therapeutically effective amounts that stimulate the desired response, for example reduction of symptoms of cancer in subjects known to have a cancer that includes cancer cells and/or cancer stem cells.

Effective amounts of a therapeutic agent can be determined in many different ways, such as assaying for improvement of a physiological condition of a subject having cancer. Effective amounts also can be determined through various in vitro, in vivo or in situ assays.

Therapeutic agents can be administered in a single dose, or in several doses, for example weekly, monthly, or bi-monthly, during a course of treatment. However, the effective amount of can be dependent on the source applied, the subject being treated, the severity and type of the condition being treated, and the manner of administration.

In one example, it is an amount sufficient to partially or completely alleviate symptoms of cancer in a subject. Treatment can involve only slowing the progression of the cancer temporarily, but can also include halting or reversing the progression of the cancer permanently. For example, a pharmaceutical preparation can decrease one or more symptoms of the cancer (such as the size of a tumor or the number of tumors or number of cancer cells and/or cancer stem cells), for example decrease a symptom by at least about 20%, at least about 50%, at least about 70%, at least about 90%, at least about 98%, or even at least about 100%, as compared to an amount in the absence of the therapeutic preparation.

Treating a disease: A therapeutic intervention that ameliorates a sign or symptom of a disease or pathological condition, such a sign or symptom of cancer. Treatment can also induce remission or cure of a condition, such as cancer and in particular a central nervous system (CNS) cancer or tumor. In particular examples, treatment includes preventing a disease, for example by inhibiting the full development of a disease, such as preventing development of tumor metastasis. Prevention of a disease does not require a total absence of a dysplasia or cancer. For example, a decrease of at least about 50% can be sufficient.

Tumor: Is a neoplasm or an abnormal mass of tissue that is not inflammatory, which arises from cells of preexistent tissue. A tumor can be either benign (noncancerous) or malignant (cancerous). Examples of hematological tumors include, but are not limited to: central nervous system (CNS) cancers or tumors. Examples of solid tumors, such as sarcomas and carcinomas, include, but are not limited to brain tumors, and CNS tumors (such as a glioma, glioblastoma, astrocytoma, medulloblastoma, craniopharyogioma, ependymoma, pinealoma, hemangioblastoma, acoustic neuroma, oligodendroglioma, menangioma, meningioma, neuroblastoma and retinoblastoma). Tumors include recurrent and/or refractory CNS tumors.

Refractory: A disease or condition which does not respond to attempted forms of treatment, for example a tumor that does not respond to the standard treatment methods.

Under conditions sufficient for: A phrase that is used to describe any environment that permits the desired activity. In one example, includes incubating a IL-4 targeted cargo protein with tumor stem cell under conditions that allow the IL-4 targeted cargo protein to specifically bind to a cancer stem cell in the sample. In another example, includes contacting one or more IL-4 targeted cargo proteins with one or more cancer cells and/or cancer stem cells in a subject sufficient to allow the desired activity. In particular examples, the desired activity is decreasing growth or multiplication of such cancer cells and/or cancer stem cells or killing cancer cells and/or cancer stem cells.

Unit dose: A physically discrete unit containing a predetermined quantity of an active material (such a IL-4 targeted cargo protein) calculated to individually or collectively produce a desired effect such as a therapeutic effect. A single unit dose or a plurality of unit doses can be used to provide the desired effect, such as a therapeutic effect.

II. Introduction

According to the present invention, PRX 321 has been developed as an intratumoral infusion product for the treatment of recurrent and/or progressive glioblastoma (GB). The formulations provided by the present invention allow for effective treatment of the recurrent and/or progressive glioblastoma (GB).

The present invention provides a method for treatment of a central nervous system (CNS) tumor in a subject, wherein the method comprises administering to the subject a formulation comprising: i) an IL-4 targeted cargo protein in an artificial cerebral spinal fluid formulation, and ii) albumin, wherein the formulation is co-administered with a surrogate tracer to a subject in need thereof.

III. Background

PRX 321 has been co-administered with a tracer (an MRI contrast agent) using convection enhanced delivery (CED) allowing real-time monitoring of drug distribution in and around the tumor. PRX 321 is a targeted immunotoxin consisting of a bioengineered circularly permuted version of interleukin-4 (cpIL-4), the binding domain, fused to a truncated version of a potent bacterial toxin-*Pseudomonas aeruginosa* exotoxin (PE) A, the catalytic domain (Kreitman et al., 1994). PRX 321 binds to interleukin-4 receptors (IL-4R) expressed on the surface of cells whereupon the entire complex is endocytosed. Following cleavage and activation by furin-like proteases found in high concentrations in the endosome of cancer cells, the catalytic domain of the truncated PE is released into the cytosol where it induces cell death via ADP-ribosylation of the Elongation Factor-2 and induction of apoptosis through caspase activation (Wedekind et al., 2001). Cells that do not express the IL-4R target do not bind to PRX 321 and are therefore, not subject to PE-mediated cell death. The mechanism of action is depicted in FIG. 1. Of note is that the PE portion was engineered to retain the catalytic domain but not the cell-binding domain; the rationale behind this approach was to have a built in safety mechanism whereby in the event PE inadvertently cleaved off from the IL-4, it could not be toxic as the binding domain of the PE was removed and consequently it would be unable to internalize into cells and arrest protein synthesis.

IV. Il-4 Fusions

Described herein are IL-4 and/or IL-13 fusion proteins that target cancer cells and/or cancer stem cells and inhibit growth of and/or kill cancer cells and/or cancer stem cells, including for example PRX 321. These molecules, herein after collectively referred to as IL-4 targeted cargo proteins, include a targeting moiety that binds to a target (e.g., in some embodiments IL-4R) displayed by the cancer stem cell as well as a cargo moiety that provides the cell growth inhibiting (or cell killing) activity. The targeting moiety can be bound to the cargo moiety directly or through one or more of a variety of linkers that are further described herein. Cancer cells and/or cancer stem cells generally have the ability to self-renew and thus generate progeny with similar properties as themselves. In some examples, the disclosed IL-4 targeted cargo proteins can target both cancer cells and/or cancer stem cells and tumor (e.g., cancer) cells that are not cancer cells and/or cancer stem cells. Therefore, in some examples IL-4 targeted cargo proteins can kill or inhibit the growth of cancer cells and/or cancer stem cells and tumor (e.g., cancer) cells that are not cancer cells and/or cancer stem cells. In other examples, such as with a targeting moiety directed to CD 133, the IL-4 targeted cargo proteins kill or inhibit the growth of cancer cells and/or cancer stem cells in the tumor, but not tumor cells that are not cancer cells and/or cancer stem cells.

Targeting moieties include proteins and other agents that function to specifically bind to a target on a cancer stem cell (but in some examples the target may also be present on other cancer cells). Targeting moieties include specific binding agents, such as antibodies, affibodies, or receptor ligands. In some examples, the targeting moiety is derived from the natural ligand to the target (e.g., cell surface receptor) displayed by the cancer stem cell. The targeting moiety that is derived from a natural ligand can include the complete amino acid sequence of the ligand (e.g. the same sequence that the ligand would have if it was isolated from nature), or the amino acid sequence of the targeting moiety can share at least about 95%, at least about 90%, at least about 80%, at least about 70%, at least about 60%, at least about 50%, or at least about 40% sequence identity with the natural ligand (e.g., at least about this amount of sequence identity to the GenBank Accession Nos. listed in Table 2), as long as the variant retains or has enhanced biological activity of the native ligand. In some examples, such variants have an increased binding affinity for their target relative to the native ligand. A targeting moiety that is derived from a natural ligand can also be a fragment of the native sequence that is capable of binding to the target displayed by the cancer stem cell. In some examples, the ligand is a circularly permuted version of a natural ligand (e.g., see U.S. Pat. No. 6,011,002). Circularly permuted molecules include those in which the termini of a linear molecule (e.g., ligand) have been joined together, either directly or via a linker, to produce a circular molecule, and then the circular molecule is opened at another location to produce a new linear molecule with termini different from the termini in the original molecule. In some examples, the targeting moiety has one or more amino acid mutations (relative to the native sequence), which alters binding to the target, such as mutations that increase binding of a ligand to its target.

Cargo moieties can reduce, inhibit the growth of, and/or kill cancer cells and/or cancer stem cells, and in some examples also inhibit the growth of, and/or kill bulk cancer cells (e.g., non stem cancer cells). These molecules can be native proteins, or proteins that have been engineered, as well as other molecules that inhibit the growth of, and/or kill cancer cells and/or cancer stem cells, and in some examples also inhibit the growth of, and/or kill bulk cancer cells (e.g., non stem cancer cells). One example of such a molecule is a chemotherapeutic agent, such as thapsigargin. Cargo moieties can be linked to targeting moieties (a linked cargo moiety and targeting moiety is referred to herein as a IL-4 targeted cargo protein) that bind to cancer cells and/or cancer stem cells. Thus, the cargo moiety linked to the targeting moiety will bind to the cancer stem cell and inhibit the growth of (or kill) the cancer stem cell. In some examples, the cargo moiety can cause cancer stem cell death and in some examples the cancer stem cell death is caused by apoptosis. In some examples cargo moieties are toxins (including plant or microorganism derived toxins), active fragments of toxins, or derivatives of toxins that share at least about 95%, at least about 90%, at least about 80%, at least about 70%, at least about 60%, at least about 50%, or at least about 40% sequence identity with the natural toxin and retains or has enhanced biological activity of the native toxin, for example with the cargo moieties provided in Table 1. In other examples the cargo moieties are derived from proteins that modulate cell life cycles or are part of natural immune responses in animals. For example, some cargo moieties are derived from proteins that are known to induce apoptosis. In some examples cargo moieties are derived from pro-apoptotic proteins, active fragments of such proteins, or derivatives of such proteins that share at least about 95%, at least about 90%, at least about 80%, at least about 70%, at least about 60%, at least about 50%, or at least about 40% sequence identity with the natural moiety (see Table 1 for sequence accession numbers), as long as the variant retains or has enhanced biological activity of the native moiety. In additional examples a cargo moiety can be inactive when administered as part of a IL-4 targeted cargo protein, and then upon contacting another molecule in the subject become active. A more detailed description of cargo moieties is provided herein.

The description also includes methods of treating subjects having (or had) cancer with the IL-4 targeted cargo protein. For example, the method can include administering one or more disclosed IL-4 targeted cargo proteins to the subject, thereby treating cancer cells and/or cancer stem cells in the subject (e.g., reducing the number or volume of stem cells). For example, the IL-4 targeted cargo proteins can be used to treat subjects with recurrent cancer or cancer that is refractory. In such examples the subject is treated with a traditional anti-cancer therapy, for example radiation, surgery, or chemotherapy and then tested to determine the effectiveness of the treatment. If the traditional therapy did not alter the cancer in a desired way, the subject can then be treated with a IL-4 targeted cargo protein.

In some examples treatment regimes that include IL-4 targeted cargo proteins and additional anticancer therapeutics can be administered to a subject. The IL-4 targeted cargo protein and the additional anticancer therapeutic will vary depending upon the type of cancer stem cell being targeted.

In specific examples, a subject is administered one or more of the following specific IL-4 targeted cargo proteins to treat cancer cells and/or cancer stem cells: circularly permuted IL-4-*Pseudomonas* exotoxin (see U.S. Pat. No. 6,011,002), IL-4-BAD, as well as PRX 321.

A. IL-4 Targeted Cargo Proteins

IL-4 targeted cargo proteins are proteins that include a targeting moiety linked to a cargo moiety. IL-4 targeted cargo proteins function to specifically bind to cancer cells and/or cancer stem cells and reduce or inhibit cancer stem cell growth, as well as targeting the immunosuppressive cells in the tumor microenvironment (TME). In some embodiments, IL-4 targeted cargo proteins comprise an IL-4R targeting moiety. In some embodiments, IL-4 targeted cargo proteins comprise an IL-4R targeting moiety comprising IL-4 or a variant thereof as described herein. In some embodiments, IL-4 targeted cargo proteins comprise an IL-4R targeting moiety comprising IL-13 or a variant thereof as described herein. In some embodiments, the IL-4 targeted cargo protein comprises PRX 321 (SEQ ID NO:1) or a variant thereof. In some embodiments, the IL-4 targeted cargo protein is PRX 321 (SEQ ID NO:1).

B. Cargo Moieties

Cargo moieties reduce or inhibit cancer stem cell growth, or kill cancer cells and/or cancer stem cells. In some examples cargo moieties are not proteins, but other molecules that reduce or inhibit cancer stem cell growth, or kill cancer cells and/or cancer stem cells, such as chemotherapeutic agents. In some examples, cargo moieties also reduce or inhibit bulk cancer cell growth, or kill cancer cells. Any protein or other agent that functions to reduce or inhibit cancer stem cell growth, or kill such cells, can be used as a cargo moiety. For example, toxins and proteins that function to control cell life cycles can be used as cargo moieties. Toxins that can be used as cargo moieties include toxins made by microorganisms, plants or animals, as well as toxins made by human cells. Similarly, any natural cell growth controlling protein can be used as a cargo moiety. For example, proteins that trigger cell death during the normal life cycle of an organism can be used as cargo moieties. In some examples, an oncolytic virus (e.g., see Allen et al., Mol. Ther. 16:1556-64, 2008) or liposomes carrying cytotoxic agents (e.g., see Madhankumar et al., Mol. Cancer. Ther. 5:3162-9, 2006) is used as the cargo protein.

In one example, the cargo moiety is a toxin. Exemplary toxins that can be used include pore-forming toxins, and toxins that upon internalization inhibit cell growth. In other examples, cargo moieties are proteins that are apoptotic triggering proteins, and cell growth inhibiting proteins. In some examples, the toxin is a modified bacterial toxin such that the resulting toxin is less immunogenic than the native toxin. Such modified toxins, such as a modified *Pseudomonas* exotoxin A, can reduce the patient's immunogenic response, thereby allowing repeated administration.

Pore forming toxins are toxins that form pores in the cell membrane thereby killing the cell via cell lyses. Exemplary pore forming toxins include but are not limited to human toxins such as perforin or bacterial toxins such as aerolysin as well as modified pore-forming protein toxins that are derived from naturally occurring pore-forming protein toxins (nPPTs) such as aerolysin or aerolysin-related polypeptides. Suitable aerolysin-related nPPTs have the following features: a pore-forming activity that is activated by removal of an inhibitory domain via protease cleavage, and the ability to bind to receptors that are present on cell membranes through one or more binding domains. In some examples the linker can be engineered to be sensitive to a protease or be chemically liable. Additional examples of pore forming toxins that can be used as cargo moieties include, but are not limited to, proaerolysin from *Aeromonas hydrophila, Aeromonas trota* and *Aeromonas salmonicida*, alpha toxin from *Clostridium septicum*, anthrax protective antigen, *Vibrio cholerae* VCC toxin, epsilon toxin from *Clostridium perfringens*, and *Bacillus thuringiensis* delta toxins. A detailed description of the engineering of proaerolysin can be found in U.S. Pat. No. 7,282,476, which is herein incorporated by reference.

Additional toxins that can be used as cargo moieties include toxins that act within a cell. For example, anthrax, diphtheria, cholera, and botulinum toxins include a portion that acts in the cytoplasm, as well as a portion that acts to bind to the cell surface. These toxins, or portions thereof, can be linked to a targeting moiety and used to inhibit cancer stem cell growth. Select members of the ribonuclease A (RNase A) superfamily are potent cytotoxins. These cytotoxic ribonucleases enter the cytosol, where they degrade cellular RNA and cause cell death.

In some examples ribosome inactivating proteins can be used as toxins. In these examples the cargo moiety is a polypeptide having ribosome-inactivating activity including, without limitation, gelonin, bouganin, saporin, ricin, ricin A chain, bryodin, restrictocin, and variants thereof. Diphtheria toxin and *Pseudomonas* exotoxin A inhibit protein synthesis via ADP-ribosylation of elongation factor 2. When the cargo moiety is a ribosome-inactivating protein or inhibits protein synthesis via ADP-ribosylation of elongation factor 2, the IL-4 targeted cargo protein can be internalized upon binding to the cancer stem cell. Cargo moieties that induce apoptosis can also be used to target cancer cells and/or cancer stem cells. Examples of cargo moieties that induce apoptosis include caspases, granzymes and BCL-2 pro-apoptotic related proteins such as BAX (e.g., Accession no: CAE52910), BAD (e.g., Accession no: CAG46757), BAT (e.g., Accession no: AA107425), BAK (e.g., Accession no: AAA74466), BIK (e.g., Accession no: CAG30276), BOK (e.g., Accession no: AAH06203), BID (e.g., Accession no: CAG28531), BIM (e.g., Accession no: NP_619527) and BMF (e.g., Accession no: AAH69328). These cargo moieties can be used alone of in combination to reduce or inhibit cancer stem cell growth.

Aerolysin is a channel-forming toxin produced as an inactive protoxin called proaerolysin (PA). Exemplary aerolysin and PA sequences that can be used in a IL-4 targeted cargo protein are provided in Table 1. The PA protein contains many discrete functionalities that include a binding domain, a toxin domain, and a C-terminal inhibitory peptide domain that contains a protease activation site. The binding domain recognizes and binds to glycophosphatidylinositol (GPI) membrane anchors, such as are found in Thy-1 on T lymphocytes, the PIGA gene product found in erythrocyte membranes and Prostate Stem Cell Antigen (PSCA). The activation or proteolysis site within proaerolysin is a six amino acid sequence that is recognized as a proteolytic substrate by the furin family of proteases. PA is activated upon hydrolysis of a C-terminal inhibitory segment by furin. Activated aerolysin binds to GPI-anchored proteins in the cell membrane and forms a heptamer that inserts into the membrane producing well-defined channels of about. 17 angstroms. Channel formation leads to rapid cell death. Wild-type aerolysin is toxic to mammalian cells, including erythrocytes, for example at 1 nanomolar or less.

In some examples, a target cargo protein is an PA molecule with the native furin site replaced with a different cleavage site, such as prostate-specific protease cleavage site (e.g., a PSA-specific cleavage site, which permits activation of the variant PA in the presence of a prostate-specific protease such as PSA, PMSA, or HK2). In one example, a prostate-specific protease cleavage site is inserted into the native furin cleavage site of PA, such that PA is activated in the presence of a prostate-specific protease, but not furin. In another example, a variant PA molecule further includes a functionally deleted binding domain (e.g., about amino acids 1-83 of a native PA protein sequence). Functional deletions can be made using any method known in the art, such as deletions, insertions, mutations, or substitutions. In some examples, IL-4 targeted cargo proteins include variant PA molecules in which the native binding domain is functionally deleted and replaced with a prostate-tissue or other tissue-specific binding domain. In other examples, variant PA molecules include a furin cleavage site and a functionally deleted binding domain which is replaced with a prostate-tissue specific binding domain. Such variant PA molecules are targeted to prostate cells via the prostate-tissue specific binding domain, and activated in the presence of furin.

Bouganin is a ribosome-binding protein originally isolated from *Bougainvillea* speotabilis (see U.S. Pat. No. 6,680,296). Exemplary modified bouganins are described in WO 2005/090579 and U.S. Pat. No. 7,339,031. Bouganin damages ribosomes and leads to a cessation of protein synthesis and cell death. Exemplary bouganin proteins that can be used in the IL-4 targeted cargo proteins of the present disclosure include those in GenBank Accession No. AAL35962, as well as those native and modified bouganin sequences provided in U.S. Pat. Nos. 6,680,296; 7,339,031 and PCT publication WO 2005/090579 (bouganin sequences herein incorporated by reference), as well as sequences having at least 60% sequence identity, at least 75%, at least 80%, at least 85%, at least 90%, at least 95%, at least 98% or even at least 99% sequence identity to such sequences.

BAD, BCL2-associated agonist of cell death, is a regulator of programmed cell death (apoptosis). BAD positively regulates cell apoptosis by forming heterodimers with BCL-xL and BCL-2, and reversing their death repressor activity. Proapoptotic activity of BAD is regulated through its phosphorylation. Exemplary BAD proteins that can be used in the IL-4 targeted cargo proteins of the present disclosure include those in GenBank Accession Nos. CAG46757; AAH01901.1; and CAG46733.1, as well as those sequences provided in U.S. Pat. No. 6,737,511 (sequences herein incorporated by reference), as well as sequences having at least 60% sequence identity, at least 75%, at least 80%, at least 85%, at least 90%, at least 95%, at least 98% or even at least 99% sequence identity to such sequences, as long as the variant retains or has enhanced biological activity of the native BAD protein.

BAX, BCL2-associated X protein, is a regulator of programmed cell death (apoptosis). This protein forms a heterodimer with BCL2, and functions as an apoptotic activator. BAX interacts with, and increases the opening of, the mitochondrial voltage-dependent anion channel (VDAC), which leads to the loss in membrane potential and the release of cytochrome c. Exemplary BAX proteins that can be used in the IL-4 targeted cargo proteins of the present disclosure include those provided by GenBank Accession Nos. CAE52909.1; AA022992.1; EAW52418.1, U.S. Pat. No. 6,645,490 (Bax in the IL2-Bax construct is a Bax-alpha variant that can be used in the present disclosure), as well as sequences having at least 60% sequence identity, at least 75%, at least 80%, at least 85%, at least 90%, at least 95%, at least 98% or even at least 99% sequence identity to such sequences, as long as the variant retains or has enhanced biological activity of the native BAX protein.

In some examples, the BAX protein of a IL-4 targeted cargo protein may be modified such that the C-terminal anchor domain has been deleted and replaced with a CaaX sequence. CaaX is a peptide with the sequence Cysteine-a-a-X where "X" is any amino acid and "a" is an aliphatic amino acid. Because membrane association of BAX is needed for optimal apoptosis activity, addition of membrane binding domains such as CaaX can enhance their pro-apoptotic activities. Proteins with CaaX sequence are farnesylated. Farnesylated proteins are targeted to membranes (e.g., see Wright and Philip, J. Lipid Res., 2006, 47 (5): 883-91). Potential BAX variants containing a CaaX sequence may or may not contain the C-terminal anchor domain.

*Pseudomonas* exotoxin (PE) is a toxin secreted by *Pseudomonas*. Native PE is cytotoxic for mammalian cells due to its ability to enter cells by receptor-mediated endocytosis and then, after a series of intracellular processing steps, translocate to the cell cytosol and ADP-ribosylate elongation factor 2. This results in the inhibition of protein synthesis and cell death. PE has three functional domains: an amino-terminal receptor-binding domain, a middle translocation domain, and a carboxyl-terminal ADP-ribosylation domain. Modified PE molecules can include elimination of domain Ia, as well as deletions in domains II and III. Exemplary PE proteins that can be used in the IL-4 targeted cargo proteins of the present disclosure include those provided in Table 1, as well as sequences having at least 60% sequence identity, at least 75%, at least 80%, at least 85%, at least 90%, at least 95%, at least 98% or even at least 99% sequence identity to such sequences, as long as the variant retains or has enhanced biological activity of the native PE protein.

Thapsigargin is an inhibitor of sarco/endoplasmic reticulum Ca2+ ATPases. Thapsigargin is classified as a sesquiterpene lactone, and raises cytosolic calcium concentration by blocking the ability of the cell to pump calcium into the sarcoplasmic and endoplasmic reticulum which causes these stores to become depleted. Store-depletion can secondarily activate plasma membrane calcium channels, allowing an influx of calcium into the cytosol.

Ribonuclease A (RNAseA) is an endonuclease that cleaves single-stranded RNA. RNAse A toxins can be obtained from mammals and reptiles. Exemplary RNAse A proteins that can be used in the IL-4 targeted cargo proteins of the present disclosure include those provided in Table 1, as well as sequences having at least 60% sequence identity, at least 75%, at least 80%, at least 85%, at least 90%, at least 95%, at least 98% or even at least 99% sequence identity to such sequences, as long as the variant retains or has enhanced biological activity of the native RNAseA toxin.

The cargo moiety used can include native sequences (such as the GenBank Accession Nos. and sequences present in the patents referenced in Table 1 and listed above), as well as variants thereof, such as a variant having at least 98%, at least 95%, at least 90%, at least 80%, at least 70%, or at least 60% sequence identity with the native cargo moiety, as long as the variant retains or has enhanced biological activity of the native cargo moiety (e.g., at least about this amount of sequence identity to the GenBank Accession Nos. listed in Table 1 and listed above). In some examples, variant sequences retain substantially the same amount (or even more) of the native biological function of the cargo moiety, such as the ability to kill or inhibit the growth of a cancer stem cell. A cargo moiety can also be a fragment of the native sequence that retains a substantial amount of the native biological function of the protein.

The cargo moieties are engineered to target cancer cells and/or cancer stem cells by linking them to targeting moieties. Targeting moieties include agents that can bind to cancer stem cell surface targets.

C. Cancer Stem Cell Targeting Moieties

Targeting moieties are the portion of the IL-4 targeted cargo proteins that target the IL-4 targeted cargo protein to cancer cells, and including cancer cells and/or cancer stem cells and bulk cancer cells. Targeting moieties function to specifically bind to a cancer stem cell. However, it is appreciated that the targeting moiety need not retain its native biological activity (e.g., the ability to activate a receptor or ability to prevent a ligand from binding to its receptor) as long as it permits the IL-4 targeted cargo protein to bind with high specificity to cancer cells and/or cancer stem cells (and in some examples also cancer cells). In certain examples, the targeting moiety is a natural ligand of a target displayed by the cancer stem cell or a derivative of a natural ligand. In other examples the targeting moiety is an antibody, such as a humanized antibody or antibody fragment, which specifically binds to a target displayed on the surface of the cancer stem cell (e.g., targets a receptor). Targeting moieties can be linked to cargo moieties using any method known in the art, for example via chemical or recombinant technology.

A non-limiting list of compounds that could be used to target cancer cells and/or cancer stem cells includes antibodies, natural ligands, engineered ligands and combinations thereof that bind to one or more cancer cells and/or cancer stem cells. Exemplary ligands include cytokines and growth factors. Exemplary targets on cancer cells and/or cancer stem cells include, for example IL-4R.

Of particular interest are targeting moieties that are molecules that are natural ligands or derivatives of the natural ligands to the target on the cancer cells and/or cancer stem cells. For example, if the cancer stem cell expresses IL-4 receptors (IL-4R), IL-4 ligand can be used as the targeting moiety. The IL-4 can be chemically or recombinantly linked to one or more of the cargo moieties described herein. Examples of derivatives of natural ligands include the circularized cytokine ligands described in U.S. Pat. No. 6,011,002 to Pastan et al., which is herein incorporated by reference. In addition to IL-4 ligands, IL-13 can also be used as a ligand targeting moiety since the IL-4 and IL-13 receptors share some sequence and biological functions. IL-4 targeted cargo proteins include those comprising IL-4 and IL-13 ligands and variants thereof.

In some examples, antibodies (including fragments, humanized antibodies and the like as described above) that target IL-4R. Antibodies are commercially available from various companies such as Millipore, Bedford, Mass. or custom made antibodies can be ordered from companies such as Cambridge Research Biochemicals, Billingham, Cleveland. Methods routine in the art can be used to generate such antibodies if desired. Such antibodies will specifically bind to cancer cells and/or cancer stem cells (and may also bind to bulk cancer cells) and function to place the cargo moiety in contact with a cancer stem cell.

IL-4 is a pleiotropic cytokine produced by activated T cells, and is the ligand for the IL-4 receptor. The IL-4 receptor also binds to IL-13. Thus, IL-13 can also be used as a targeting moiety to target the IL-4 receptor. IL-4, IL-3, IL-5, IL-13, and CSF2 form a cytokine gene cluster on human chromosome 5q, with this gene particularly close to IL-13. Exemplary IL-4 and IL-13 proteins that can be used in the IL-4 targeted cargo proteins of the present disclosure include those provided in Table 2, as well as sequences having at least 60% sequence identity, at least 75%, at least 80%, at least 85%, at least 90%, at least 95%, at least 98% or even at least 99% sequence identity to such sequences, as long as the variant retains the ability to bind the IL-4 receptor.

The targeting moiety used can include native sequences (such as the GenBank Accession Nos. and sequences present in the patents referenced in Table 2 and listed above), as well as variants thereof, such as a variant having at least 98%, at least 95%, at least 90%, at least 80%, at least 70%, or at least 60% sequence identity with the native targeting moiety protein (e.g., at least about this amount of sequence identity to the GenBank Accession Nos. listed in Table 2 and listed above). In some examples, variant sequences retain substantially the same amount (or even more) of the native biological function of the targeting moiety protein, such as the ability to activate an intracellular signal cascade. However, variant targeting moiety molecules may in some examples retain little or no native biological activity, but retain the ability to bind the appropriate target (e.g., bind to the appropriate cell surface receptor or protein) with high specificity.

D. Linkers

Linking of a cargo moiety to a targeting moiety may be direct meaning that one portion of the cargo moiety is directly attached to a portion of the targeting moiety. For example, one end of the amino acid sequence of a cargo protein can be directly attached to an end of the amino acid sequence of the targeting moiety. For example, the C-terminus of the cargo protein can be linked to the N-terminus of the targeting moiety, or the C-terminus of the targeting moiety can be linked to the N-terminus of the cargo protein. Methods of generating such fusion proteins are routine in the art, for example using recombinant molecular biology methods.

In another example, the cargo moiety is linked to the targeting moiety indirectly through a linker. The linker can serve, for example, simply as a convenient way to link the two entities, as a means to spatially separate the two entities, to provide an additional functionality to the IL-4 targeted cargo protein, or a combination thereof.

In general, the linker joining the targeting moiety and the cargo moiety can be designed to (1) allow the two molecules to fold and act independently of each other, (2) not have a propensity for developing an ordered secondary structure which could interfere with the functional domains of the two moieties, (3) have minimal hydrophobic or charged characteristic which could interact with the functional protein domains and/or (4) provide steric separation of the two regions. For example, in some instances it may be desirable to spatially separate the targeting moiety and the cargo moiety to prevent the targeting moiety from interfering with the inhibitory activity of the targeted cargo moiety and/or the cargo moiety interfering with the targeting activity of the targeting moiety. The linker can also be used to provide, for example, lability to the connection between the targeting moiety and the cargo moiety, an enzyme cleavage site (for example a cleavage site for a protease), a stability sequence, a molecular tag, a detectable label, or various combinations thereof.

The linker can be bifunctional or polyfunctional, e.g. contains at least about a first reactive functionality at, or proximal to, a first end of the linker that is capable of bonding to, or being modified to bond to, the targeting moiety and a second reactive functionality at, or proximal to, the opposite end of the linker that is capable of bonding to, or being modified to bond to, the cargo moiety being modified. The two or more reactive functionalities can be the same (i.e. the linker is homobifunctional) or they can be different (i.e. the linker is heterobifunctional). A variety of bifunctional or polyfunctional cross-linking agents are known in the art that are suitable for use as linkers (for example, those commercially available from Pierce Chemical Co., Rockford, Ill.), such as avidin and biotin. Alternatively, these reagents can be used to add the linker to the targeting moiety and/or cargo moiety.

The length and composition of the linker can be varied considerably provided that it can fulfill its purpose as a molecular bridge. The length and composition of the linker are generally selected taking into consideration the intended function of the linker, and optionally other factors such as ease of synthesis, stability, resistance to certain chemical and/or temperature parameters, and biocompatibility. For example, the linker should not significantly interfere with the ability of the targeting moiety to target the IL-4 targeted cargo protein to a cancer stem cell, or with the activity of the IL-4 targeted cargo protein relating to activation, pore-forming ability, or toxin activity.

Linkers suitable for use may be branched, unbranched, saturated, or unsaturated hydrocarbon chains, as well as peptides as noted above. Furthermore, if the linker is a peptide, the linker can be attached to the targeting moiety and/or the cargo moiety using recombinant DNA technology. Such methods are well-known in the art and details of this technology can be found, for example, in Sambrook et al., supra.

In one example, the linker is a branched or unbranched, saturated or unsaturated, hydrocarbon chain having from 1 to 100 carbon atoms, wherein one or more of the carbon atoms is optionally replaced by —O— or —NR— (wherein R is H, or C1 to C6 alkyl), and wherein the chain is optionally substituted on carbon with one or more substituents selected from the group of (C1-C6) alkoxy, (C3-C6) cycloalkyl, (C1-C6) alkanoyl, (C1-C6) alkanoyloxy, (C1-C6) alkoxycarbonyl, (C1-C6) alkylthio, amide, azido, cyano, nitro, halo, hydroxy, oxo (.dbd.O), carboxy, aryl, aryloxy, heteroaryl, and heteroaryloxy.

Examples of suitable linkers include, but are not limited to, peptides having a chain length of 1 to 500 amino acid residues (such as 1 to 100, 1 to 50, 6 to 30, such as less than 30 amino acids). Typically surface amino acids in flexible protein regions include Gly, Asn and Ser. Other neutral amino acids, such as Thr and Ala, can also be used in the linker sequence. Additional amino acids can be included in the linker to provide unique restriction sites in the linker sequence to facilitate construction of the fusions. Other exemplary linkers include those derived from groups such as ethanolamine, ethylene glycol, polyethylene with a chain length of 6 to 100 carbon atoms, polyethylene glycol with 3 to 30 repeating units, phenoxyethanol, propanolamide, butylene glycol, butyleneglycolamide, propyl phenyl, and ethyl, propyl, hexyl, steryl, cetyl, and palmitoyl alkyl chains.

In one example, the linker is a branched or unbranched, saturated or unsaturated, hydrocarbon chain, having from 1 to 50 carbon atoms, wherein one or more of the carbon atoms is optionally replaced by —O— or —NR— (wherein R is as defined above), and wherein the chain is optionally substituted on carbon with one or more substituents selected from the group of (C1-C6) alkoxy, (C1-C6) alkanoyl, (C1-C6) alkanoyloxy, (C1-C6) alkoxycarbonyl, (C1-C6) alkylthio, amide, hydroxy, oxo (.dbd.O), carboxy, aryl and aryloxy.

In a specific example, the linker is a peptide having a chain length of 1 to 50 amino acid residues, such as 1 to 40, 1 to 20, or 5 to 10 amino acid residues.

Peptide linkers that are susceptible to cleavage by enzymes of the complement system, urokinase, tissue plasminogen activator, trypsin, plasmin, or another enzyme having proteolytic activity may be used in one example. According to another example, the IL-4 targeted cargo protein includes a targeting moiety attached via a linker susceptible to cleavage by enzymes having a proteolytic activity such as a urokinase, a tissue plasminogen activator, plasmin, thrombin or trypsin. In addition, targeting moieties may be attached to the cargo moiety via disulfide bonds (for example, the disulfide bonds on a cysteine molecule). Since many tumors naturally release high levels of glutathione (a reducing agent) this can reduce the disulfide bonds with subsequent release of the cargo moiety at the site of delivery.

In one example, the IL-4 targeted cargo protein includes a targeting moiety linked by a cleavable linker region. In another example, the cleavable linker region is a protease-cleavable linker, although other linkers, cleavable for example by small molecules, may be used. Examples of protease cleavage sites are those cleaved by factor Xa, thrombin and collagenase. In one example, the protease cleavage site is one that is cleaved by a protease that is associated with a disease. In another example, the protease cleavage site is one that is cleaved by a protease that is up-regulated or associated with cancers in general. Examples of such proteases are uPA, the matrix metalloproteinase (MMP) family, the caspases, elastase, prostate specific antigen (PSA, a serine protease), and the plasminogen activator family, as well as fibroblast activation protein. In still another example, the cleavage site is cleaved by a protease secreted by cancer-associated cells. Examples of these proteases include matrixmetalloproteases, elastase, plasmin, thrombin, and uPA. In another example, the protease cleavage site is one that is up-regulated or associated with a specific cancer. The precise sequences are available in the art and the skilled person will have no difficulty in selecting a suitable cleavage site. By way of example, the protease cleavage region targeted by Factor Xa is I E G R. The protease cleavage region targeted by enterokinase is DDDD K. The protease cleavage region targeted by thrombin is L V P R G. In one example, the cleavable linker region is one which is targeted by endocellular proteases.

As known in the art, the attachment of a linker to cargo moiety (or of a linker element to a cleavable element, or a cleavable element to another cargo moiety) need not be a particular mode of attachment or reaction.

E. Exemplary Cargo Moiety/Targeting Moiety Combinations

1. PRX 321

PRX 321 has been developed for the treatment of recurrent/progressive glioblastoma (GB). Using current treatment paradigms, most GB patients experience tumor recurrence/progression after standard first line treatment. Treatment options for patients with recurrent GB are very limited and the outcome is generally unsatisfactory. Specifically, chemotherapy regimens for recurrent or progressive GB have been unsuccessful, producing toxicity without benefit (Weller et al., 2013). This is mainly due to the lack of tissue specificity with resultant toxicity to normal tissues and consequently, a narrow therapeutic index. As overall survival remains dismal, novel anti-cancer modalities, with greater tumor specificity, more robust cytotoxic mechanisms and novel delivery techniques are needed for the treatment of recurrent GB.

PRX 321 is a novel therapeutic that provides a targeted treatment approach whereby tumor cells are more sensitive to the toxic effects of the drug than normal cells. The target, IL-4R, is an ideal but under-exploited target for the development of cancer therapeutics, as it is frequently and intensely expressed on a wide variety of human carcinomas. Expression levels of IL-4R are low on the surface of healthy and normal cells, but increase several-fold on cancer cells. A majority of cancer biopsy and autopsy samples from adult and pediatric central nervous system (CNS) tumors, including recurrent GB biopsies, have been shown to over-express the IL-4R. There is little or no IL-4R expression in normal adult and pediatric brain tissue (Joshi, et al., 2001; Table 2 of the reference). This differential expression of the IL-4R provides PRX 321 a wide therapeutic window (see Table 4 of the reference for IC50 data). This feature alone makes PRX 321 an ideal candidate for the treatment of recurrent GB and other CNS tumors that over-express the IL-4R. Cells that do not express the IL-4R target do not bind to PRX 321 and are, therefore, not subject to PE-mediated effects.

2. Other Combinations

Any combination of cargo moiety and IL-4 based targeting moiety can be employed according to the present invention. In this section exemplary combinations of targeting moieties and cargo moieties are provided. In all examples that targeting moiety can be an antibody that specifically binds to a target, such as a fully humanized antibody.

IL-4 (including IL-4 circularly permuted ligands and other IL-4 receptor binding proteins such as IL-13) is another targeting moiety that can be linked to BCL-2 family proteins, such as BAX, BAD, BAT, BAK, BIK, BOK, BID BIM, BMF and BOK, or a toxin such as acrolysin, proaerolysin, *Pseudomonas* exotoxin, or combinations thereof. Any form or derivative of IL-4 can be used as the targeting moiety. For example, IL-4 or fragments of IL-4 that bind to the IL-4 receptor can be used. Additionally, multiple cargo moieties can be linked to IL-4 or multiple IL-4 proteins can be linked to cargo moieties.

Any form or derivative of IL-4 can be used as the targeting moiety. For example, IL-4 or fragments of IL-4 that bind to the IL-4 receptor can be used. Additionally, multiple cargo moieties can be linked to IL-4 or multiple IL-2 proteins can be linked to cargo moieties.

A circularly permuted ligand, for example a circularly permuted ligand derived from IL-4 can be employed as the targeting moiety. *Pseudomonas* exotoxin can be employed as the cargo moiety. Any form or derivative of circularly permuted IL-4 ligand can be used as the targeting moiety. Additionally, multiple cargo moieties can be linked to a circularly permuted ligand or multiple circularly permuted ligand proteins can be linked to cargo moieties.

V. Formulations/Compositions

Pharmaceutical compositions can include one or more IL-4 targeted cargo proteins and one or more non-toxic pharmaceutically acceptable carriers, diluents, excipients and/or adjuvants. If desired, other active ingredients may be included in the compositions. As indicated above, such compositions are suitable for use in the treatment of cancer. The term "pharmaceutically acceptable carrier" refers to a carrier medium which does not interfere with the effectiveness of the biological activity of the active ingredients and which is not toxic to the host or patient. Representative examples are provided below.

The pharmaceutical compositions may comprise, for example, from about 1% to about 95% of a IL-4 targeted cargo protein. Compositions formulated for administration in a single dose form may comprise, for example, about 20% to about 90% of the IL-4 targeted cargo proteins, whereas compositions that are not in a single dose form may comprise, for example, from about 5% to about 20% of the IL-4 targeted cargo proteins. Concentration of the IL-4 targeted cargo protein in the final formulation can be at least 1 ng/mL, such as at least 1 μg/mL or at least 1 mg/mL. For example, the concentration in the final formulation can be between about 0.01 μg/mL and about 1,000 μg/mL. In one example, the concentration in the final formulation is between about 0.01 mg/mL and about 100 mg/mL.

The composition can be a liquid solution, suspension, emulsion, sustained release formulation, or powder. The composition can be formulated as a suppository, with traditional binders and carriers such as triglycerides.

The IL-4 targeted cargo proteins can be delivered along with a pharmaceutically acceptable vehicle. In one example, the vehicle may enhance the stability and/or delivery properties. Thus, the disclosure also provides for formulation of the IL-4 targeted cargo protein with a suitable vehicle, such as an artificial membrane vesicle (including a liposome, noisome, nanosome and the like), microparticle or microcapsule, or as a colloidal formulation that comprises a pharmaceutically acceptable polymer. The use of such vehicles/polymers may be beneficial in achieving sustained release of the IL-4 targeted cargo proteins. Alternatively, or in addition, the IL-4 targeted cargo protein formulations can include additives to stabilize the protein in vivo, such as human serum albumin, or other stabilizers for protein therapeutics known in the art. IL-4 targeted cargo protein formulations can also include one or more viscosity enhancing agents which act to prevent backflow of the formulation when it is administered, for example by injection or via catheter. Such viscosity enhancing agents include, but are not limited to, biocompatible glycols and sucrose.

Pharmaceutical compositions formulated as aqueous suspensions contain the active compound(s) in admixture with one or more suitable excipients, for example, with suspending agents, such as sodium carboxymethylcellulose, methyl cellulose, hydropropylmethylcellulose, sodium alginate, polyvinylpyrrolidone, hydroxypropyl-.beta.-cyclodextrin, gum tragacanth and gum acacia; dispersing or wetting agents such as a naturally-occurring phosphatide, for example, lecithin, or condensation products of an alkylene oxide with fatty acids, for example, polyoxyethyene stearate, or condensation products of ethylene oxide with long chain aliphatic alcohols, for example, hepta-decaethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxy-benzoate, or one or more coloring agents.

Pharmaceutical compositions can be formulated as oily suspensions by suspending the active compound(s) in a vegetable oil, for example, *arachis* oil, olive oil, sesame oil or coconut oil, or in a mineral oil such as liquid paraffin. The oily suspensions may contain a thickening agent, for example, beeswax, hard paraffin or cetyl alcohol. Compositions can be preserved by the addition of an anti-oxidant such as ascorbic acid.

The pharmaceutical compositions can be formulated as a dispersible powder or granules, which can subsequently be used to prepare an aqueous suspension by the addition of water. Such dispersible powders or granules provide the active ingredient in admixture with one or more dispersing or wetting agents, suspending agents and/or preservatives. Suitable dispersing or wetting agents and suspending agents are exemplified by those already mentioned above.

Pharmaceutical compositions can also be formulated as oil-in-water emulsions. The oil phase can be a vegetable oil, for example, olive oil or *arachis* oil, or a mineral oil, for example, liquid paraffin, or it may be a mixture of these oils. Suitable emulsifying agents for inclusion in these compositions include naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the said partial esters with ethylene oxide, for example, polyoxyethylene sorbitan monoleate.

The pharmaceutical compositions containing one or more IL-4 targeted cargo proteins can be formulated as a sterile injectable aqueous or oleaginous suspension according to methods known in the art and using suitable one or more dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

In one example, the IL-4 targeted cargo protein is conjugated to a water-soluble polymer, e.g., to increase stability or circulating half life or reduce immunogenicity. Clinically acceptable, water-soluble polymers include, but are not limited to, polyethylene glycol (PEG), polyethylene glycol propionaldehyde, carboxymethylcellulose, dextran, polyvinyl alcohol (PVA), polyvinylpyrrolidone (PVP), polypropylene glycol homopolymers (PPG), polyoxyethylated polyols (POG) (e.g., glycerol) and other polyoxyethylated polyols, polyoxyethylated sorbitol, or polyoxyethylated glucose, and other carbohydrate polymers. Methods for conjugating polypeptides to water-soluble polymers such as PEG are described, e.g., in U.S. patent Pub. No. 20050106148 and references cited therein. In one example the polymer is a pH-sensitive polymers designed to enhance the release of drugs from the acidic endosomal compartment to the cytoplasm (see for example, Henry et al., Biomacromolecules 7 (8): 2407-14, 2006).

IL-4 targeted cargo proteins can also be administered in therapeutically effective amounts together with one or more anti-cancer therapeutics. The compound(s) can be administered before, during or after treatment with the anti-cancer therapeutic.

An "anti-cancer therapeutic" is a compound, composition, or treatment (e.g., surgery) that prevents or delays the growth and/or metastasis of cancer cells. Such anti-cancer therapeutics include, but are not limited to, surgery (e.g., removal of all or part of a tumor), chemotherapeutic drug treatment, radiation, gene therapy, hormonal manipulation, immunotherapy (e.g., therapeutic antibodies and cancer vaccines) and antisense or RNAi oligonucleotide therapy. Examples of useful chemotherapeutic drugs include, but are not limited to, hydroxyurea, busulphan, cisplatin, carboplatin, chlorambucil, melphalan, cyclophosphamide, Ifosphamide, danorubicin, doxorubicin, epirubicin, mitoxantrone, vincristine, vinblastine, Navelbine.RTM. (vinorelbine), etoposide, teniposide, paclitaxel, docetaxel, gemcitabine, cytosine, arabinoside, bleomycin, neocarcinostatin, suramin, taxol, mitomycin C, Avastin, Herceptin.RTM., flurouracil, and temozolamide and the like. The compounds are also suitable for use with standard combination therapies employing two or more chemotherapeutic agents. It is to be understood that anti-cancer therapeutics includes novel compounds or treatments developed in the future.

The pharmaceutical compositions described above include one or more IL-4 targeted cargo proteins in an amount effective to achieve the intended purpose. Thus the term "therapeutically effective dose" refers to the amount of the IL-4 targeted cargo protein that ameliorates the symptoms of cancer. Determination of a therapeutically effective dose of a compound is well within the capability of those skilled in the art. For example, the therapeutically effective dose can be estimated initially either in cell culture assays, or in animal models, such as those described herein. Animal models can also be used to determine the appropriate concentration range and route of administration. Such information can then be used to determine useful doses and routes for administration in other animals, including humans, using standard methods known in those of ordinary skill in the art.

Therapeutic efficacy and toxicity can also be determined by standard pharmaceutical procedures such as, for example, by determination of the median effective dose, or ED.sub.50 (i.e. the dose therapeutically effective in 50% of the population) and the median lethal dose, or LD.sub.50 (i.e. the dose lethal to 50% of the population). The dose ratio between therapeutic and toxic effects is known as the "therapeutic index," which can be expressed as the ratio, LD.sub.50/ED.sub.50. The data obtained from cell culture assays and animal studies can be used to formulate a range of dosage for human or animal use. The dosage contained in such compositions is usually within a range of concentrations that include the ED.sub.50 and demonstrate little or no toxicity. The dosage varies within this range depending upon the dosage form employed, sensitivity of the subject, and the route of administration and the like. Exemplary dosage ranges that can be used include at least 1 ng/g tumor, at least 1 μg/g tumor, or at least 1 mg/g tumor, such as dosage ranges from about 0.01 μg/g tumor to about 50 μg/g tumor, from about 0.02 u/g tumor to about 40 μg/g tumor, from about 0.02 μg/g tumor to about 35 μg/g tumor, 0.03 μg/g tumor to about 25 μg/g tumor, from about 0.04 μg/g tumor to about 20 μg/g tumor, from about 0.04 μg/g tumor to about 10 μg/g tumor, and from about 0.5 μg/g tumor to about 2 μg/g tumor.

One of ordinary skill in the art will appreciate that the dosage will depend, among other things, upon the type of IL-4 targeted cargo protein being used and the type of cancer stem cell being treated.

In some embodiments, the IL-4 targeted cargo protein is PRX 321 of SEQ ID NO:1:

```
MDTTEKETFCRAATVLRQFYSHHEKDTRCLGATAQQFHRHKQLIRFLKLR

DRNLWGLAGLNSCPVKEANQSTLENFLERLKTIMREKYSKCSSGGNGGHK
```

-continued

CDITLQEIIKTLNSLTEQKTLCTELTVTDIFAASKASGGPEGGSLAALTA

HQACHLPLETFTRHRQPRGWEQLEQCGYPVQRLVALYLAARLSWNQVDQV

IRNALASPGSGGDLGEAIREQPEQARLALTLAAAESERFVRQGTGNDEAG

AANGPADSGDALLERNYPTGAEFLGDGGDVSFSTRGTQNWTVERLLQAHR

QLEERGYVFVGYHGTFLEAAQSIVFGGVRARSQDLDAIWRGFYIAGDPAL

AYGYAQDQEPDARGRIRNGALLRVYVPRSSLPGFYRTSLTLAAPEAAGEV

ERLIGHPLPLRLDAITGPEEEGGRLETILGWPLAERTVVIPSAIPTDPRN

VGGDLDPSSIPDKEQAISALPDYASQPGKPPKDEL

PRX 321 has also been described in US Patent Publication NO. 2016/0271231, incorporated by reference herein in its entirety for all purposes.

In some embodiments, the IL-4 targeted cargo protein is diluted in artificial CSF. In some embodiments, the PRX 321 is diluted in an artificial cerebral spinal fluid (artificial CSF). In some embodiments, the artificial CSF comprises calcium chloride, dextrose, magnesium sulfate, potassium chloride, sodium bicarbonate, sodium chloride, sodium phosphate, dibasic, and is diluted in water. In some embodiments, the artificial CSF is Elliotts B® solution. In some embodiments, the artificial CSF is employed to produce an infusate having a final composition of PRX 321 at 3 µg/mL. In some embodiments, the artificial CSF is employed to produce an infusate having a final composition of PRX 321 at 3 µg/mL. In some embodiments, the artificial CSF is employed to produce an infusate having a final composition of PRX 321 at 3 µg/mL, 0.02% human serum albumin and gadolinium-diethylenetriamine pentaacetic acid (Gd-DTPA, Magnevist®) at 7 mM.

In some embodiments, the formulation and routes of administration described herein allow for about 80%, about 85%, about 90%, about 95%, or about 100% of the tumor and the 1 cm margin around it (at risk for tumor spread) to be successfully covered. In some embodiments, the formulation and routes of administration described herein allow for about 80% to about 100% of the tumor and the 1 cm margin around it (at risk for tumor spread) to be successfully covered. In some embodiments, the formulation and routes of administration described herein allow for about 85% to about 100% of the tumor and the 1 cm margin around it (at risk for tumor spread) to be successfully covered. In some embodiments, the formulation and routes of administration described herein allow for about 90% to about 100% of the tumor and the 1 cm margin around it (at risk for tumor spread) to be successfully covered. In some embodiments, the formulation and routes of administration described herein allow for about 95% to about 100% of the tumor and the 1 cm margin around it (at risk for tumor spread) to be successfully covered. In some embodiments, the formulation and routes of administration described herein allow for about 100% of the tumor and the 1 cm margin around it (at risk for tumor spread) to be successfully covered.

TABLE 3

Reagents used in the Preparation of Infusate

| Reagent | Type | Grade | Manufacturer/Distributor |
| --- | --- | --- | --- |
| PRX 321 | Drug Product | CGMP, sterile | Medicenna Therapeutics Inc. |
| Elliotts B® Solution | Excipient | USP, sterile | Lukare Medical, LLC |
| HSA 5% (aqueous) Solution | Excipient | USP, sterile | Octapharma |
| Gd-DTPA, Magnevist® 469.1 | Excipient | USP, sterile | Bayer Healthcare Pharmaceuticals Inc. |

Abbreviations:
CGMP, Current Good Manufacturing Practice;
NDC, National Drug Code;
USP, United States Pharmacopeia PRX 321 Formulation Embodiment Composition of PRX 321: Drug product is supplied as a sterile frozen solution of PRX 321 at a concentration of 500 µg/mL contained in 0.5 mL Phosphate Buffered Saline (10 mM sodium phosphate, 500 mM sodium chloride, pH 7.4±0.1), filled in a sterile, single-use, 2 mL Type 1 USP dehydrogenated clear glass vial sealed with 13 mm Teflon-faced stopper and labeled as shown below:

PRX 321 Vial: PRX-321 contains 0.5 mL of PRX 321 (500 µg/m) and should be stored at ≤−70° C. The vial is labeled with "Sterile Single Dose Vials for Intratumoral Administration via Stereotactically Placed Catheters".

Storage: Drug product is stored at −70° C.+/−10° C. in its secondary packaging until required for preparation of infusate. Hospital pharmacy temperature monitoring records must be provided for all periods in which drug product vial(s) are stored for review by the study monitor.

Handling: Infusate will be prepared, using aseptic technique using a pre-sanitized biological safety (vertical flow) cabinet. After the preparation of the infusate, the used drug product vial should be discarded according to the hospital pharmacy's standard operating procedure.

Excipients

Upon receipt of shipment, the shipping container will be opened by the hospital Pharmacist who must inspect condition of the contents and ensure that the excipient kits are undamaged. The pharmacist must follow the instructions that will be included in the shipment for downloading the temp tale monitor data as well as complete/return the proof of receipt documentation that arrives with the shipment whereby condition of receipt will be documented. The hospital pharmacist must record inventory of the shipment using the Excipient Kit Inventory Form (Appendix 3). In the event that there is an issue identified during receipt of a excipient kit shipment, the hospital pharmacy should notify the contacts specified in Section 3.0 of this manual immediately.

In some embodiments, the IL-4 targeted cargo protein is provided as a kit. In some embodiments, the PRX 321 is provided as a kit. In some embodiments, the kit contains 4 components:
Human Serum Albumin (HSA)
Elliotts B Solution
Magnevist (Gd-DTPA)
Empty IV Bag The container has a tamper seal at the opening end to secure closure. One Excipient Kit is to be used for one infusate preparation.

Excipient Kit components:
1×250 ml bottle HSA 5% (aqueous) Solution
1× unit Elliotts B Solution (10×10 mL ampules)
1×5 mL vial of Gd-DTPA
1 × empty (150 mL size) IV Bag The excipient kit components are to be used in PRX 321 infusate preparation as described in the present example. The kit provides materials for single (1×) PRX 321 infusate preparation.

Storage: Excipient kit is stored at controlled room temperature until required for preparation of infusate.

Handling: Excipient kit should be handled with care and stored right side up (label of kit in at the top).

Human Serum Albumin

In some embodiments, Human Serum Albumin (HSA) is added to the infusate, at a final concentration of 0.02%, to prevent adsorption of PRX 321 to the inner surfaces of the syringes, tubes and catheter used in the infusion assembly.

Supply: 1×250 ml bottle (Octapharma HSA 5% (aqueous) Solution, NCT #68982-0623-02)

Storage: at controlled room temperature as recommended by the manufacturer.

Handling: HSA should be handled using aseptic techniques in a pre-sanitized biological safety cabinet. Once opened and or used, the remaining HSA should be discarded according to the hospital pharmacy's standard operating procedure.

Buffered Intrathecal Electrolyte/Dextrose Injection (Elliotts B® Solution)

PRX 321 drug product is diluted in Elliotts B® Solution.

TABLE 4

Composition/Information on Ingredients:

| Specific Chemical Identity | CAS # | Chemical Formula | Quantity per mL |
|---|---|---|---|
| Calcium Chloride | 10035-04-8 | $CaCl_2$ | 0.2 mg |
| Dextrose | 50-99-7 | $C_6H_{12}O_6$ | 0.8 mg |
| Magnesium Sulfate | 10034-99-8 | $MgSO_4\ 7\ H_2O$ | 0.3 mg |
| Potassium Chloride | 7447-40-7 | KCl | 0.3 mg |
| Sodium Bicarbonate | 144-55-8 | $NaHCO_3$ | 1.9 mg |
| Sodium Chloride | 7647-14-5 | NaCl | 7.3 mg |
| Sodium Phosphate, Dibasic | 7782-85-6 | $Na_2HPO_4\ 7\ H_2O$ | 0.2 mg |
| Water for Injection | 7732-18-5 | $H_2O$ | 1 mL |

Further information on the Elliott's B Solution. Elliotts B® Solution is a sterile, nonpyrogenic, isotonic solution containing no bacteriostatic preservatives. Elliotts B Solution is a diluent for intrathecal administration of methotrexate sodium and cytarabine. Each 10 mL of Elliotts B Solution contains:

TABLE 5

Composition per 10 mL

| Specific Chemical Identity | Quantity per 10 mL |
|---|---|
| Sodium Chloride, USP | 73 mg |
| Sodium Bicarbonate, USP | 19 mg |
| Dextrose, USP | 8 mg |
| Magnesium Sulfate•7H2O, USP | 3 mg |
| Potassium Chloride, USP | 3 mg |
| Calcium Chloride•2H2O, USP | 2 mg |
| Sodium Phosphate, dibasic•7H2O, USP | 2 mg |
| Water for Injection, USP qs 10 mL | To 10 mL |

TABLE 6

Concentration of Electrolytes:

| | | | |
|---|---|---|---|
| Sodium | 149 mEq/liter | Bicarbonate | 22.6 mEq/liter |
| Potassium | 4.0 mEq/liter | Chloride | 132 mEq/liter |
| Calcium | 2.7 mEq/liter | Sulfate | 2.4 mEq/liter |
| Magnesium | 2.4 mEq/liter | Phosphate | 1.5 mEq/liter |

TABLE 7 formulae and molecular weights of the ingredients:

| INGREDIENT | MOLECULAR FORMULA | MOLECULAR WEIGHT |
|---|---|---|
| Sodium Chloride | NaCl | 58.44 |
| Sodium Bicarbonate | NaHCO3 | 84.01 |
| Dextrose | C6H12O6 | 180.16 |
| Magnesium Sulfate•7H2O | Mg2SO4•7H2O | 246.48 |
| Potassium Chloride | KCl | 74.55 |
| Calcium Chloride•2H2O | CaCl2•2H2O | 147.01 |
| Sodium Phosphate, dibasic•7H2O | Na2HPO4•7H2O | 268.07 |

The pH of Elliotts B Solution is 6.0-7.5, and the osmolarity is 288 mOsmol per liter (calculated).

Elliotts B Solution provides a buffered salt solution for use as a diluent for the intrathecal administration of methotrexate sodium and cytarabine. It has been demonstrated that Elliotts B Solution is comparable to cerebrospinal fluid in pH, electrolyte composition, glucose content, and osmolarity:

TABLE 8

Comparison of Electrolyte Composition, pH and Nonelectrolytic Constituents of Elliotts B Solution and CSF:

| Solution | Na+ mEq/L | K+ mEq/L | Co++ mEq/L | Mg++ mEq/L | HCO3− mEq7L | Cl− mEq/L | pH | Phosphorus mg/dL | Glucose mg/dL |
|---|---|---|---|---|---|---|---|---|---|
| Cerebrospinal Fluid | 117-137 | 2.3-4.6 | 2.2 | 2.2 | 22.9 | 113-127 | 7.31 | 1.2-2.1 | 45-80 |
| Elliotts B Solution | 149 | 4.0 | 2.7 | 2.4 | 22.6 | 132 | 6.0-7.5 | 2.3 | 80 |

The approximate buffer capacity of Elliotts B Solution is $1.1 \times 10^{-2}$ equivalents when the challenge solution is 0.01 N HCl and $7.8 \times 10^{-3}$ equivalents when the challenge solution is 0.01 N NaOH. Compatibility studies with methotrexate sodium and cytarabine indicate these drugs are physically compatible with Elliotts B Solution.

Elliott's B solution is a diluent used in the preparation of infusate; it is comparable to cerebrospinal fluid in pH, electrolyte composition, glucose content, osmolarity and buffering capacity.

Gadolinium-diethylenetriamine pentaacetic acid (Gd-DTPA) Magnevist®

In some embodiments, Gd-DTPA (diluted to ~1:70) is added to the infusate as a contrast agent as co-infusion of this surrogate tracer during infusion allows real-time monitoring of PRX 321 infusate distribution.

Supply: 1×5 mL single use vial of Gd-DTPA (Bayer HealthCare Pharmaceuticals Inc. Magnevist®; 469.1 mg/mL, NDC #50419-188-05).

Storage: stored according to manufacturer's instructions.

Handling: Gd-DTPA (Magnevist®) should be handled using aseptic techniques in a pre-sanitized biological safety cabinet. Once opened or used, the remaining should be discarded in accordance with regulations dealing with the disposal of such materials and according to the hospital pharmacy's standard operating procedure.

VI. Making Il-4 Targeted Cargo Proteins

IL-4 targeted cargo proteins can be prepared by many routine methods as known in the art. IL-4 targeted cargo proteins, as well as modifications thereto, can be made, for example, by engineering the nucleic acid encoding the IL-4 targeted cargo protein using recombinant DNA technology or by peptide synthesis. Modifications to the IL-4 targeted cargo protein may be made, for example, by modifying the IL-4 targeted cargo protein polypeptide itself, using chemical modifications and/or limited proteolysis. Combinations of these methods may also be used to prepare the IL-4 targeted cargo proteins.

Methods of cloning and expressing proteins are well-known in the art, detailed descriptions of techniques and systems for the expression of recombinant proteins can be found, for example, in Current Protocols in Protein Science (Coligan, J. E., et al., Wiley & Sons, New York). Those skilled in the art will understand that a wide variety of expression systems can be used to provide the recombinant protein. Accordingly, the IL-4 targeted cargo proteins can be produced in a prokaryotic host (e.g., *E. coli, A. salmonicida* or *B. subtilis*) or in a eukaryotic host (e.g., *Saccharomyces* or *Pichia*; mammalian cells, e.g., COS, NIH 3T3, CHO, BHK, 293, or Hela cells; or insect cells). The IL-4 targeted cargo proteins can be purified from the host cells by standard techniques known in the art.

Sequences for various exemplary cargo moieties and targeting moieties are provided in the Tables 1 and 2. Variants and homologs of these sequences can be cloned, if an alternative sequence is desired, using standard techniques [see, for example, Ausubel et al., Current Protocols in Molecular Biology, Wiley & Sons, NY (1997 and updates); Sambrook et al., supra]. For example, the nucleic acid sequence can be obtained directly from a suitable organism, such as *Aeromonas hydrophila*, by extracting mRNA and then synthesizing cDNA from the mRNA template (for example by RT-PCR) or by PCR-amplifying the gene from genomic DNA. Alternatively, the nucleic acid sequence encoding either the targeting moiety or the cargo moiety can be obtained from an appropriate cDNA library by standard procedures. The isolated cDNA is then inserted into a suitable vector, such as a cloning vector or an expression vector.

Mutations (if desired) can be introduced at specific, pre-selected locations by in vitro site-directed mutagenesis techniques well-known in the art. Mutations can be introduced by deletion, insertion, substitution, inversion, or a combination thereof, of one or more of the appropriate nucleotides making up the coding sequence.

The expression vector can further include regulatory elements, such as transcriptional elements, required for efficient transcription of the IL-4 targeted cargo protein-encoding sequences. Examples of regulatory elements that can be incorporated into the vector include, but are not limited to, promoters, enhancers, terminators, and polyadenylation signals. Vectors that include a regulatory element operatively linked to a nucleic acid sequence encoding a genetically engineered IL-4 targeted cargo protein can be used to produce the IL-4 targeted cargo protein.

The expression vector may additionally contain heterologous nucleic acid sequences that facilitate the purification of the expressed IL-4 targeted cargo protein, such as affinity tags such (e.g., metal-affinity tags, histidine tags, avidin/streptavidin encoding sequences, glutathione-S-transferase (GST) encoding sequences, and biotin encoding sequences). In one example, such tags are attached to the N- or C-terminus of a IL-4 targeted cargo protein, or can be located within the IL-4 targeted cargo protein. The tags can be removed from the expressed IL-4 targeted cargo protein prior to use according to methods known in the art. Alternatively, the tags can be retained on the IL-4 targeted cargo protein, providing that they do not interfere with the ability of the IL-4 targeted cargo protein to target and kill (or decrease growth of) cancer cells and/or cancer stem cells.

As an alternative to a directed approach to introducing mutations into naturally occurring pore-forming proteins, a cloned gene expressing a pore-forming protein can be subjected to random mutagenesis by techniques known in the art. Subsequent expression and screening of the mutant forms of the protein thus generated would allow the identification and isolation of targeted cargo moieties.

The IL-4 targeted cargo proteins can also be prepared as fragments or fusion proteins. A fusion protein is one which includes a IL-4 targeted cargo protein linked to other amino acid sequences that do not inhibit the ability of the IL-4 targeted cargo protein to selectively target and inhibit cancer stem cell growth or kill cancer cells and/or cancer stem cells. In an alternative example, the other amino acid sequences are short sequences of, for example, up to about 5, about 6, about 7, about 8, about 9, about 10, about 20, about 30, about 50 or about 100 amino acid residues in length. These short sequences can be linker sequences as described above.

Methods for making fusion proteins are well known to those skilled in the art. For example U.S. Pat. No. 6,057,133 discloses methods for making fusion molecules composed of human interleukin-3 (hIL-3) variant or mutant proteins functionally joined to a second colony stimulating factor, cytokine, lymphokine, interleukin, hematopoietic growth factor or IL-3 variant. U.S. Pat. No. 6,072,041 to Davis et al. discloses the generation of fusion proteins comprising a single chain Fv molecule directed against a transcytotic receptor covalently linked to a therapeutic protein.

The IL-4 targeted cargo protein can include one or more linkers, as well as other moieties, as desired. These can include a binding region, such as avidin or an epitope, or a tag such as a polyhistidine tag, which can be useful for purification and processing of the fusion protein. In addition, detectable markers can be attached to the fusion protein, so that the traffic of the fusion protein through a body or cell can be monitored conveniently. Such markers include radionuclides, enzymes, fluorophores, chromophores, and the like.

One of ordinary skill in the art will appreciate that the DNA can be altered in numerous ways without affecting the biological activity of the encoded protein. For example, PCR can be used to produce variations in the DNA sequence which encodes a IL-4 targeted cargo protein. Such variations in the DNA sequence encoding a IL-4 targeted cargo protein can be used to optimize for codon preference in a host cell used to express the protein, or may contain other sequence changes that facilitate expression.

A covalent linkage of a targeting moiety directly to a cargo moiety or via a linker may take various forms as is known in the art. For example, the covalent linkage may be in the form of a disulfide bond. The DNA encoding one of the components can be engineered to contain a unique cysteine codon. The second component can be derivatized with a sulfhydryl group reactive with the cysteine of the first component. Alternatively, a sulfhydryl group, either by itself or as part of a cysteine residue, can be introduced using solid phase polypeptide techniques. For example, the introduction of sulfhydryl groups into peptides is described by Hiskey (Peptides 3:137, 1981).

Proteins also can be chemically modified by standard techniques to add a sulfhydryl group. For example, Traut's reagent (2-iminothiolane-HCl) (Pierce Chemicals, Rockford, Ill.) can be used to introduce a sulfhydryl group on primary amines, such as lysine residues or N-terminal amines. A protein or peptide modified with Traut's reagent can then react with a protein or peptide which has been modified with reagents such as N-succinimidyl 3-(2-pyridyldithio) propionate (SPDP) or succinimidyl 4-(N-malcimidomethyl) cyclohexane-1-carboxylate (SMCC) (Pierce Chemicals, Rockford, Ill.).

The components can also be joined using the polymer, monomethoxy-polyethylene glycol (mPEG), as described in Maiti et al., Int. J. Cancer Suppl., 3:17-22, 1988.

The targeting moiety and the cargo moiety can also be conjugated through the use of standard conjugation chemistries as is known in the art, such as carbodiimide-mediated coupling (for example, DCC, EDC or activated EDC), and the use of 2-iminothiolane to convert epsilon amino groups to thiols for crosslinking and m-maleimidobenzoyl-n-hydroxysuccinimidyl ester (MBS) as a crosslinking agent.

VII. Testing II-4 Targeted Cargo Proteins

IL-4 targeted cargo proteins can be tested using standard techniques known in the art. Exemplary methods of testing candidate IL-4 targeted cargo proteins are provided below and in the examples included herein. One of ordinary skill in the art will understand that other methods of testing the IL-4 targeted cargo proteins are known in the art and are also suitable for testing candidate IL-4 targeted cargo proteins. For example, methods known in the art for testing for anti-tumor activity can be used. The IL-4 targeted cargo proteins can initially be screened against a panel of cancer cell lines or cancer stem cell lines. A cell proliferation assay, such as the WST-1 kit sold by Roche, can be used. Potency can be evaluated using different drug concentrations in the presence or absence of agents that inhibit cancer cells or sensitize cancer cells and/or cancer stem cells. Selected drug candidates from the initial cancer stem cell screen can be further characterized through additional in vitro assays and in relevant xenograft models to examine anti-tumor activity.

A. In Vitro

IL-4 targeted cargo proteins can be tested for their ability to kill cancer stem cells or significantly reduce or inhibit the growth of cancer cells and/or cancer stem cells using known methods. For example, the ability of the IL-4 targeted cargo proteins to kill or inhibit growth of cells can be assayed in vitro using suitable cells, typically a cell line expressing the target or a stem cancer cell. In general, cells of the selected test cell line are grown to an appropriate density and the candidate IL-4 targeted cargo protein is added. The IL-4 targeted cargo protein can be added to the culture at around at least 1 ng/mL, at least 1 μg/mL, or at least 1 mg/mL, such as from about 0.01 μg/mL to about 1 mg/mL, from about 0.10 μg/mL to about 0.5 mg/mL, from about 1 μg/mL to about 0.4 mg/mL. In some examples, serial dilutions are tested. After an appropriate incubation time (for example, about 48 to 72 hours), cell survival or growth is assessed. Methods of determining cell survival are well known in the art and include, but are not limited to, the resazurin reduction test (see Fields & Lancaster Am. Biotechnol. Lab., 11:48-50, 1993; O'Brien et al., Eur. J. Biochem., 267:5421-5426, 2000 and U.S. Pat. No. 5,501,959), the sulforhodamine assay (Rubinstein et al., J. Natl. Cancer Inst., 82:113-118, 1999) or the neutral red dye test (Kitano et al., Euro. J. Clin. Investg., 21:53-58, 1991; West et al., J. Investigative Derm., 99:95-100, 1992) or trypan blue assay. Numerous commercially available kits may also be used, for example the CellTiter 96.RTM. AQueous One Solution Cell Proliferation Assay (Promega). Cytotoxicity is determined by comparison of cell survival in the treated culture with cell survival in one or more control cultures, for example, untreated cultures and/or cultures pretreated with a control compound (typically a known therapeutic), or other appropriate control. IL-4 targeted cargo proteins considered to be effective in killing or reducing the growth of cancer cells and/or cancer stem cells are capable of decreasing cell survival or growth, for example, by at least about 10%, at least about 20%, at least about 30%, at least about 40%, or at least about 50%.

In some examples the IL-4 targeted cargo protein can be not significantly toxic to non-cancer cells and/or cancer stem cells. For example, the IL-4 targeted cargo protein when incubated at around at least 1 ng/mL, at least 1 μg/mL, or at least 1 mg/mL, such as from about 0.01 μg/mL to about 1 mg/mL, from about 0.10 μg/mL to about 0.5 mg/mL, from about 1 μg/mL to about 0.4 mg/mL in cell culture with cells not displaying the target (e.g., does not express IL-2R) will kill less than about 50%, less than about 40%, less than about 30%, less than about 20%, or less than about 10% of the non-cancer cells and/or cancer stem cells. In some examples, the IL-4 targeted cargo protein when incubated at around at least 1 ng/mL, at least 1 μg/mL, or at least 1 mg/mL, such as from about 0.01 μg/mL to about 1 mg/mL, from about 0.10 g/mL to about 0.5 mg/mL, from about 1 μg/mL to about 0.4 mg/mL in cell culture with cells not displaying the target (e.g., does not express IL-2R) will have at least a 10-fold greater $LD_{50}$ toward the non-cancer cells and/or cancer stem cells, such as an at least 20-fold greater, at least 50-fold greater, or at least 100-fold greater LD.sub.50 toward the non-cancer cells and/or cancer stem cells.

In some examples IL-4 targeted cargo proteins include a toxin that contains one or more modifications to an activation sequence. These activatable IL-4 targeted cargo proteins can be tested for their ability to be cleaved by the appropriate activating agent according to methods known in the art. For example, if the one or more modifications result in the addition of one or more protease cleavage sites, the IL-4 targeted cargo protein can be incubated with varying concentrations of the appropriate protease(s). The incubation products can be electrophoresed on SDS-PAGE gels and cleavage of the IL-4 targeted cargo protein can be assessed by examining the size of the polypeptide on the gel.

In order to determine if the activatable IL-4 targeted cargo proteins that have been incubated with protease retain pore-forming activity, and thus the ability to kill cells, after incubation with the protease, the reaction products can be tested in a hemolysis assay as is known in the art. An example of a suitable assay is described in Howard and Buckley, J. Bacteriol., 163:336-40, 1985, which is herein incorporated by reference.

IL-4 targeted cargo proteins that confer selectivity for a specific type of cancer may be tested for their ability to target that specific cancer cell type. For example, a IL-4 targeted cargo protein comprising an IL-4 that targets cancer cells and/or cancer stem cells displaying IL-4R can be assessed for its ability to selectively target cancer cells and/or cancer stem cells by comparing the ability of the IL-4 targeted cargo protein to kill cancer cells and/or cancer stem cells to its ability to kill a normal cell, or a different type of cancer cell (e.g., one that does not express IL-4R). Alternatively, flow cytometric methods, as are known in the art, may be used to determine if a IL-4 targeted cargo protein comprising an IL-4 targeting moiety is able to selectively target a specific type of cancer stem cell. Binding of a labeled antibody to the bound IL-4 targeted cargo protein will indicate binding of the IL-4 targeted cargo protein to the target.

A variety of cancer cell-lines suitable for testing the candidate IL-4 targeted cargo proteins are known in the art and many are commercially available (for example, from the American Type Culture Collection, Manassas, Va.). In one example, in vitro testing of the candidate compounds is conducted in a human cancer cell-line. In another example, cancer cells and/or cancer stem cells are isolated and cultured as described in US Patent Application No. 2007/0292389 to Stassi et al. The cultured stem cells are used to test the activity of the IL-4 targeted cargo protein. Initial testing of the targeting moiety can be performed by linking the targeting moiety to a detectable label such as a fluorescent label and contacting a sample known to contain the appropriate cancer cells and/or cancer stem cells with the targeting moiety and observing the associated fluorescent label bound to the cancer stem cell.

Additional in vitro testing of IL-4 targeted cargo proteins can be accomplished using cell lines that have been engineered to express the desired target. An antibody specific for the target can be used to ensure that the target is being expressed. Upon binding to the cell expressing the target, the IL-4 targeted cargo protein may cause cell lysis which can be detected using methods known in the art.

B. In Vivo

The ability of the IL-4 targeted cargo proteins to kill tumor cells in vivo can be determined in an appropriate animal model using standard techniques known in the art (see, for example, Enna, et al., Current Protocols in Pharmacology, J. Wiley & Sons, Inc., New York, N.Y.).

Current animal models for screening anti-tumor compounds include xenograft models, in which a human tumor has been implanted into an animal. Using these techniques cancer cells and/or cancer stem cells can be transplanted and the presence, size and morphology of the resulting tumor can be assessed. Examples of xenograft models of human cancer include, but are not limited to, human solid tumor xenografts, implanted by sub-cutaneous injection or implantation and used in tumor growth assays; human solid tumor isografts, implanted by fat pad injection and used in tumor growth assays; human solid tumor orthotopic xenografts, implanted directly into the relevant tissue and used in tumor growth assays; experimental models of lymphoma and leukemia in mice, used in survival assays, and experimental models of lung metastasis in mice. In addition to the implanted human tumor cells, the xenograft models can further comprise transplanted human peripheral blood leukocytes, which allow for evaluation of the anti-cancer immune response.

Alternatively, murine cancer models can be used for screening anti-tumor compounds. Examples of appropriate murine cancer models are known in the art and include, but are not limited to, implantation models in which murine cancer cells are implanted by intravenous, subcutaneous, fat pad or orthotopic injection; murine metastasis models; transgenic mouse models; and knockout mouse models.

For example, the IL-4 targeted cargo proteins can be tested in vivo on solid tumors using mice that are subcutaneously grafted bilaterally with 30 to 60 mg of a tumor fragment, or implanted with an appropriate number of cancer cells and/or cancer stem cells (e.g., at least 10.sup.3, at least 10.sup.4, or at least at least 10.sup.6 cancer cells and/or cancer stem cells, such as from about 10 to about 10.sup.5, from about 50 to about 10.sup.4, or from about 75 to about 10.sup.3), on day 0. The animals bearing tumors are randomized before being subjected to the various treatments and controls. In the case of treatment of advanced tumors, tumors are allowed to develop to the desired size, animals having insufficiently developed tumors being eliminated. The selected animals are distributed at random to undergo the treatments and controls. Animals not bearing tumors may also be subjected to the same treatments as the tumor-bearing animals in order to be able to dissociate the toxic effect from the specific effect on the tumor. Chemotherapy generally begins from 3 to 22 days after grafting, depending on the type of tumor, and the animals are observed every day. The IL-4 targeted cargo proteins can be administered to the animals, for example, by i.p. injection, intravenous injection, direct injection into the tumor (or into the organ having the tumor), or bolus infusion. The amount of IL-4 targeted cargo protein that is injected can be determined using the in vitro testing results described above. For example, at least about 1 ng/kg body weight, at least 1 μg/kg body weight, or at least 1 mg/kg body weight, such as from about 0.01 μg/kg body weight to about 1 mg/kg body weight, from about 0.10 μg/kg body weight to about 1.0 g/kg body weight, from about 1 mg/kg body weight to about 4 mg/kg body weight. The different animal groups are weighed about 3 or 4 times a week until the maximum weight loss is attained, after which the groups are weighed at least about once a week until the end of the trial.

The tumors are measured after a pre-determined time period, or they can be monitored continuously by measuring about 2 or 3 times a week until the tumor reaches a pre-determined size and/or weight, or until the animal dies if this occurs before the tumor reaches the pre-determined size/weight. The animals are then sacrificed and the tissue histology, size and/or proliferation of the tumor assessed. Orthotopic xenograft models are an alternative to subcutaneous models and may more accurately reflect the cancer development process. In this model, tumor cells are implanted at the site of the organ of origin and develop internally. Daily evaluation of the size of the tumors is thus more difficult than in a subcutaneous model. A recently developed technique using green fluorescent protein (GFP) expressing tumors in non-invasive whole-body imaging can help to address this issue (Yang et al., Proc. Nat. Aca. Sci., 1206-1211, 2000). This technique utilizes human or murine tumors that stably express very high levels of green fluorescent protein (GFP). The GFP expressing tumors can be visualized by means of externally placed video detectors, allowing for monitoring of details of tumor growth, angiogenesis and metastatic spread. Angiogenesis can be measured over time by monitoring the blood vessel density within the tumor(s). The use of this model thus allows for simultaneous monitoring of several features associated with tumor progression and has high preclinical and clinical relevance.

For the study of the effect of the compositions on leukemias, the animals are grafted with a particular number of cells, and the anti-tumor activity is determined by the increase in the survival time of the treated mice relative to the controls.

To study the effect of a particular IL-4 targeted cargo protein on tumor metastasis, tumor cells are typically treated with the composition ex vivo and then injected into a suitable test animal. The spread of the tumor cells from the site of injection is then monitored over a suitable period of time.

IL-4 targeted cargo proteins that are sufficiently effective at inhibiting cancer stem cell growth (as evidenced by in vitro cell survival assays, metastasis inhibition assays, and/or xenograph model systems) can be chosen for use in humans. IL-4 targeted cargo proteins can also be chosen for trial and eventual therapeutic use in humans based upon their relative toxicity at the potential therapeutic dosage range indicated by the assays. Therapeutic dosages and toxicity are further described below.

VIII. Therapeutic Uses

The IL-4 targeted cargo proteins described herein can be used for a variety of therapeutic purposes. Prior to administration for therapeutic purposes the IL-4 targeted cargo protein may need to be modified or adapted for the particular purpose, for example the concentration of IL-4 targeted cargo protein needed for whole body administration may differ from that used for local administration. Similarly, the toxicity of the therapeutic may change depending upon the mode of administration and overall composition being used (e.g., buffer, diluent, additional chemotherapeutic, etc.).

A. Toxicity

Therapeutic proteins may elicit some level of antibody response when administered to a subject, which in some cases may lead to undesirable side effects. Therefore, if necessary, the antigenicity of the IL-4 targeted cargo proteins can be assessed as known in the art and described below. In addition, methods to reduce potential antigenicity are described.

In vivo toxic effects of the IL-4 targeted cargo proteins can be evaluated by measuring their effect on animal body weight during treatment and by performing hematological profiles and liver enzyme analysis after the animal has been sacrificed. The general toxicity of the IL-4 targeted cargo proteins can be tested according to methods known in the art. For example, the overall systemic toxicity of the IL-4 targeted cargo proteins can be tested by determining the dose that kills 100% of mice (i.e. LD100) following a single intravenous injection. Doses that were at least about 2, 5, or 10-fold less than the LD100 or LD50 can be selected for administration into other mammals, such as a human.

The kinetics and magnitude of the antibody response to the IL-4 targeted cargo proteins described herein can be determined, for example, in immunocompetent mice and can be used to facilitate the development of a dosing regimen that can be used in an immunocompetent human. Immunocompetent mice such as the strain C57-BL6 are administered intravenous doses of IL-4 targeted cargo protein. The mice are sacrificed at varying intervals (e.g. following single dose, following multiple doses) and serum obtained. An ELISA-based assay can be used to detect the presence of anti-IL-4 targeted cargo protein antibodies.

To decrease antigenicity of IL-4 targeted cargo proteins the native binding domain of the toxin used as the cargo moiety can be functionally deleted and replaced, for example with a targeting moiety to make the IL-4 targeted cargo protein. The antigenicity of such IL-4 targeted cargo proteins can be determined following exposure to varying schedules of the IL-4 targeted cargo protein which lack portions of the native binding domain using the methods described above. IL-4 targeted cargo proteins that utilize fully humanized antibodies can also be used to minimize antigenicity.

Another method that can be used to allow continued treatment with IL-4 targeted cargo proteins is to use sequentially administered alternative IL-4 targeted cargo proteins derived from other cargo proteins with non-overlapping antigenicity. For example, a IL-4 targeted cargo protein derived from proaerolysin can be used alternately with a IL-4 targeted cargo protein derived from *Clostridium septicum* alpha toxin or *Bacillus thuringiensis* delta-toxin. All of these IL-4 targeted cargo proteins would target cancer cells and/or cancer stem cells, but would not be recognized or neutralized by the same antibodies.

Serum samples from these mice can be assessed for the presence of anti-IL-4 targeted cargo protein antibodies as known in the art. As another example, epitope mapping can also be used to determine antigenicity of proteins as described in Stickler, et al., J. Immunotherapy, 23:654-660, 2000. Briefly, immune cells known as dendritic cells and CD4+ T cells are isolated from the blood of community donors who have not been exposed to the protein of interest. Small synthetic peptides spanning the length of the protein are then added to the cells in culture. Proliferation in response to the presence of a particular peptide suggests that a T cell epitope is encompassed in the sequence. This peptide sequence can subsequently be deleted or modified in the IL-4 targeted cargo protein thereby reducing its antigenicity.

B. Treatment of Glioblastoma

In some embodiments, the IL-4 targeted cargo protein is employed for the treatment of a brain tumor. In some embodiments, the brain tumors is glioblastoma (GB). Glioblastoma (GB) is an aggressive brain tumor characterized by rapid proliferation of undifferentiated cells, extensive infiltration, and a high propensity to recur (Hamstra et al., 2005). It is a rapidly progressing and universally fatal cancer. For adults treated with concurrent Temozolomide (Termodar®) and radiotherapy, median survival is 14.6 months, two-year survival is approximately 30%, and five-year survival approximately 10%. Clinical impact is defined by rapid neurologic deterioration which affects the ability to perform everyday functions, such as eating, walking, and talking. There can also be distortion of personality and identity, such as mood, memory, emotion, and intelligence. GB does not typically metastasize outside of the CNS and death usually results due to increased intracranial pressure and herniation caused by uncontrolled growth of tumor within the bone-encased brain cavity. Annual worldwide incidence of primary GB in well-resourced countries is approximately 27,500 (Decision Recourses, 2013).

C. Patient Populations

The IL-4 targeted cargo proteins of the invention, including for example PRX 321 finds use for the treatment of recurrent GB in particular patient populations.

In some embodiments, the cancer biopsy and autopsy samples are from adult and pediatric CNS tumors (e.g., brain tumors). In some embodiments, the patient has glioblastoma (GB). In some embodiments, the patient has recurrent GB. In some embodiments, the patient tumor samples have been shown to over-express the IL-4R as compared to little or no IL-4R expression in normal adult and pediatric brain tissue (Puri et al., 1994a; Kawakami et al., 2002a; Joshi, et al., 2001; Konanbash et al., 2013). While not being bound by theory, cells that do not express the IL-4R target do not bind to PRX 321 and are, therefore, not subject to PE-mediated effects (Kawakami et al., 2002).

In some embodiments, the IL-4 targeted cargo proteins, including for example PRX 321, induce tumor growth killing that is not growth-rate dependent (Li and Hall, 2010). In some embodiments, quiescent cancer cells and/or cancer stem cells and slower growing non-malignant cells of the tumor microenvironment (TME) may be as sensitive to PRX 321 as rapidly dividing tumor cells In some embodiments, the cancer cells are 06-methylguanine-methyltransferase (MGMT) positive. In some embodiments, 06-methylguanine-methyltransferase (MGMT) positive cancer cells (harboring unmethylated MGMT promoters and therefore resistant to Temozolomide) are sensitive to PRX 321. Exemplary sensitive CNS cancer cell lines include T98G (glioblastoma) and have been shown to over-express MGMT. Such cell lines are resistant to alkylating agents such as Temozolomide (Huang et al., 2012; Kuo et al., 2007; Kokkinakis et al., 2003), but can be sensitive to PRX 321. In some embodiments, IL-4R-expressing cell lines show picomolar sensitivity to PRX 321. See, for example, Puri et al., 1996b; Kreitman et al., 1995; Shimamura et al., 2007. In some embodiments, IL-4R-expressing tumors exhibit picomolar sensitivity to the IL-4 targeted cargo proteins of the present invention. In some embodiments, IL-4R-expressing tumors exhibit picomolar sensitivity to PRX 321. In some embodiments, MGMT expressing tumors exhibit sensitivity to the IL-4 targeted cargo proteins of the present invention. In some embodiments, IL-4R-expressing gliobalstomas exhibit sensitivity to PRX 321. In some embodiments, MGMT-expressing tumors exhibit sensitivity to PRX 321. In some embodiments, MGMT-expressing gliobalstomas exhibit sensitivity to PRX 321.

Furin like protease cleavage of PRX 321 and result in activation of the PE toxin (Chironi et al., 1997; Shapira and Benhar, 2010) and glioblastomas often express furin (Mercapide, et al., 2002; Wick et al., 2004). The higher expression levels of furin in glioma cells as opposed to normal cells provides additional tumor specificity and also a contributes to factor to the exceptional picomolar sensitivity of cancer cells to PRX 321. In some embodiments, the tumor expresses furin. In some embodiments, the tumor expressing furin is more sensitive to the IL-4 targeted cargo proteins, such as PRX 321, than normal non-tumor cells.

IL-4R is over-expressed not only by CNS tumors but also by non-malignant cells (MDSCs and TAMs) of the immunosuppressive TME. In some embodiments, the IL-4R IL-4 targeted cargo proteins, including PRX 321, find use in the treatment adult and pediatric patients with aggressive forms of primary and metastatic brain cancer.

GB has a robust immunosuppressive TME and may comprise up to 40% of the tumor mass (Kennedy et al., 2013). Recently, it has been shown that malignant gliomas have a T-helper cell type-2 (Th2) bias and are heavily infiltrated by myeloid derived suppressor cells (MDSCs) and tumor associated macrophages (TAMs) and that the IL4/IL-4R bias mediates their immunosuppressive functions (Harshyne, et al., 2016). Furthermore, IL-4R is up-regulated on glioma-infiltrating myeloid cells but not in the periphery or in normal brain (Kohanbash et al., 2013). In some embodiments, purging Th2 cells, MDSCs, and TAMs using the IL-4 targeted cargo proteins of the present invention, including PRX 321, may alleviate the immune block associated with cancer. In some embodiments, the alleviation of immune block promotes anti-tumor immunity and aid in long-term disease control and/or disease treatment.

D. Administration and Dosing

The IL-4 targeted cargo proteins can be used to treat, stabilize or prevent CNS cancer, including for example the IL-4 targeted cargo protein PRX 321. IL-4 targeted cargo proteins can also be used in the treatment of indolent cancers, recurrent cancers including locally recurrent, distantly recurrent and/or refractory cancers (i.e. cancers that have not responded to other anti-cancer treatments), metastatic cancers, locally advanced cancers and aggressive cancers. In these contexts, the IL-4 targeted cargo proteins may exert either a cytotoxic or cytostatic effect resulting in, for example, a reduction in the number or growth of cancer cells and/or cancer stem cells, a reduction in the size of a tumor, the slowing or prevention of an increase in the size of a tumor, an increase in the disease-free survival time between the disappearance or removal of a tumor and its reappearance, prevention of an initial or subsequent occurrence of a tumor (e.g. metastasis), an increase in the time to progression, reduction of one or more adverse symptoms associated with a tumor, or an increase in the overall survival time of a subject having cancer.

Typically, in the treatment of cancer, IL-4 targeted cargo proteins are administered systemically to patients, for example, by bolus injection or continuous infusion into a patient's bloodstream. Alternatively, the IL-4 targeted cargo proteins may be administered locally, at the site of a tumor (intratumorally). When a IL-4 targeted cargo protein is administered intratumorally, the administration can be via any route, e.g., locally, regionally, focally, systemic, convection enhanced delivery or combinations thereof.

When used in conjunction with one or more known chemotherapeutic agents, the compounds can be administered prior to, or after, administration of the chemotherapeutic agents, or they can be administered concomitantly. The one or more chemotherapeutics may be administered systemically, for example, by bolus injection or continuous infusion, or they may be administered orally.

For administration to an animal, the pharmaceutical compositions can be formulated for administration by a variety of routes. For example, the compositions can be formulated for topical, rectal or parenteral administration or for administration by inhalation or spray. The term parenteral as used herein includes subcutaneous injections, intravenous, intramuscular, intrathecal, intrasternal injection or infusion techniques. Direct injection or infusion into a tumor is also contemplated. Convection enhanced delivery can also be used to administer the IL-4 targeted cargo protein.

In one example, the IL-4 targeted cargo protein can be injected into a subject having cancer, using an administration approach similar to the multiple injection approach of brachytherapy. For example, multiple aliquots of the purified IL-4 targeted cargo protein in the form of a pharmaceutical composition or formulation and in the appropriate dosage units, may be injected using a needle. Alternative methods of administration of the IL-4 targeted cargo proteins will be evident to one of ordinary skill in the art. Such methods include, for example, the use of catheters, or implantable pumps to provide continuous infusion of the IL-4 targeted cargo protein to the subject in need of therapy.

As is known in the art, software planning programs can be used in combination with brachytherapy treatment and ultrasound, for example, for placement of catheters for infusing IL-4 targeted cargo proteins to treat, for example, brain tumors or other localized tumors. For example, the positioning and placement of the needle can generally be achieved under ultrasound guidance. The total volume, and therefore the number of injections and deposits administered to a patient, can be adjusted, for example, according to the volume or area of the organ to be treated. An example of a suitable software planning program is the brachytherapy treatment planning program Variseed 7.1 (Varian Medical Systems, Palo Alto, Calif.). Such approaches have been successfully implemented in the treatment of prostate cancer among others.

If necessary to reduce a systemic immune response to the IL-4 targeted cargo proteins, immunosuppressive therapies can be administered in combination with the IL-4 targeted cargo proteins. Examples of immunosuppressive therapies include, but are not limited to, systemic or topical corticosteroids (Suga et al., Ann. Thorac. Surg., 73:1092-7, 2002), cyclosporin A (Fang et al., Hum. Gene Ther., 6:1039-44, 1995), cyclophosphamide (Smith et al., Gene Ther., 3:496-502, 1996), deoxyspergualin (Kaplan et al., Hum. Gene Ther., 8:1095-1104, 1997) and antibodies to T and/or B cells [e.g. anti-CD40 ligand, anti CD4 antibodies, anti-CD20 antibody (Rituximab)](Manning et al., Hum. Gene Ther., 9:477-85, 1998). Such agents can be administered before, during, or subsequent to administration of the IL-4 targeted cargo proteins. Such agents can be administered from about 10 mg/week to about 1000 mg/week, from about 40 mg/week to about 700 mg/week, or from about 200 mg/week to about 500 mg/week for 2, 3, 4, 5, 6, or 7 weeks. Courses of treatment can be repeated as necessary if the subject remains responsive (e.g., the symptoms of cancer are static or decreasing).

The IL-4 targeted cargo protein can also be administered in combination with a sensitizing agent, such as a radiosensitizers (see for example Diehn et al., J. Natl. Cancer Inst. 98:1755-7, 2006). Generally, a sensitizing agent is any agent that increases the activity of a IL-4 targeted cargo protein. For example, a sensitizing agent will increase the ability of a IL-4 targeted cargo protein to inhibit cancer stem cell growth or kill cancer cells and/or cancer stem cells. Exemplary sensitizing agents include antibodies to IL-10, bone morphogenic proteins and HDAC inhibitors (see for example Sakariassen et al., Neoplasia 9 (11): 882-92, 2007). These sensitizing agents can be administered before or during treatment with the IL-4 targeted cargo protein. Exemplary dosages of such sensitizing agents include at least 1 µg/mL, such as at least 10 µg/mL, at least 100 µg/mL, for example 5-100 g/mL or 10-90 µg/mL. The sensitizing agents can be administered daily, three times a week, twice a week, once a week or once every two weeks. Sensitizing agent can also be administered after treatment with the IL-4 targeted cargo protein is finished.

The IL-4 targeted cargo proteins may be used as part of a neo-adjuvant therapy (to primary therapy), as part of an adjuvant therapy regimen, where the intention is to cure the cancer in a subject. The IL-4 targeted cargo proteins can also be administered at various stages in tumor development and progression, including in the treatment of advanced and/or aggressive neoplasias (e.g., overt disease in a subject that is not amenable to cure by local modalities of treatment, such as surgery or radiotherapy), metastatic disease, locally advanced disease and/or refractory tumors (e.g., a cancer or tumor that has not responded to treatment).

"Primary therapy" refers to a first line of treatment upon the initial diagnosis of cancer in a subject. Exemplary primary therapies may involve surgery, a wide range of chemotherapies and radiotherapy. "Adjuvant therapy" refers to a therapy that follows a primary therapy and that is administered to subjects at risk of relapsing. Adjuvant systemic therapy is begun soon after primary therapy, for example 2, 3, 4, 5, or 6 weeks after the last primary therapy treatment to delay recurrence, prolong survival or cure a subject. As noted above, it is contemplated that the IL-4 targeted cargo proteins can be used alone or in combination with one or more other chemotherapeutic agents as part of an adjuvant therapy. Combinations of the IL-4 targeted cargo proteins and standard chemotherapeutics may act to improve the efficacy of the chemotherapeutic and, therefore, can be used to improve standard cancer therapies. This application can be particularly important in the treatment of drug-resistant cancers which are not responsive to standard treatment. The dosage to be administered is not subject to defined limits, but it will usually be an effective amount. The compositions may be formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. The unit dosage forms may be administered once or multiple unit dosages may be administered, for example, throughout an organ, or solid tumor. Examples of ranges for the IL-4 targeted cargo protein(s) in each dosage unit are from about 0.0005 to about 100 mg, or more usually, from about 1.0 to about 1000 mg. Daily dosages of the IL-4 targeted cargo proteins typically are at least 1 ng/kg of body weight, at least 1 µg/kg of body weight, at least 1 mg/kg of body weight, for example fall within the range of about 0.01 to about 100 mg/kg of body weight, in single or divided dose. However, it will be understood that the actual amount of the compound(s) to be administered will be determined by a physician, in the light of the relevant circumstances, including the condition to be treated, the chosen route of administration, the actual compound administered, the age, weight, and response of the individual patient, and the severity of the patient's symptoms. The above dosage range is given by way of example only and is not intended to limit the scope in any way. In some instances, dosage levels below the lower limit of the aforesaid range may be more than adequate, while in other cases still larger doses may be employed without causing harmful side effects, for example, by first dividing the larger dose into several smaller doses for administration throughout the day.

The IL-4 targeted cargo proteins can be used to treat and/or manage cancer, the methods include administering to a subject in need thereof a prophylactically or therapeutically effective regimen, the regimen comprising administering one or more therapies to the subject, wherein the regimen results in the stabilization or reduction in the cancer stem cell population and does not result in a reduction or only results in a small reduction of the circulating endothelial cell population and/or the circulating endothelial progenitor population. In one example, the regimen achieves a 5%-40%, a 10%-60%, or a 20 to 99% reduction in the cancer stem cell population and/or less than a 25%, less than a 15%, or less than a 10% reduction in the circulating endothelial cell population. In another example, the regimen achieves a 5%-40%, a 10%-60%, or a 20 to 99% reduction in the cancer stem cell population and/or less than a 25%, less than a 15%, or less than a 10% reduction in the circulating endothelial progenitor population. In another example, the regimen achieves a 5%-40%, a 10%-60%, or a 20 to 99% reduction in the cancer stem cell population and/or less than a 25%, less than a 15%, or less than a 10% reduction in the circulating endothelial cell population and the circulating endothelial progenitor population. In a specific example, the stabilization or reduction in the cancer stem cell population is achieved after two weeks, a month, two months, three months, four months, six month, nine months, 1 year, 2 years, 3 years, 4 years or more of administration of one or more of the therapies. In a particular example, the stabilization or reduction in the cancer stem cell population can be determined using any method known in the art. In certain examples, in accordance with the regimen, the circulating cancer stem cell population, the circulating endothelial cell population and/or the circulating endothelial progenitor population is monitored periodically (e.g., after 2, 5, 10, 20, 30 or more doses of one or more of the therapies or after 2 weeks, 1 month, 2 months, 6 months, 1 year, or more of receiving one or more therapies).

In some embodiments, a single infusion of the IL-4 targeted cargo protein, such as for example PRX 321, is administered at a concentration of 1.5 μg/mL (and up to 3 μg/mL) (see, for example, Examples 1 and 2). In some embodiments, infusion volume and parameters can be personalized for each subject/patient to achieve target coverage to the maximum extent possible. In some embodiments, infused volume will range from approximately 7 mL (smallest tumor) to 60 mL (largest tumor). In some embodiments, the duration of infusion will be approximately 6 to 32 hours depending on tumor volume, flow rate and number of catheters. In some embodiments, the maximum delivered dose will be 90 μg. In some embodiments, the dosage is administered intra-cranially. In some embodiments, the IL-4 targeted cargo protein is administered as a single dose of about 90 μg (1.5 μg/mL in 60 mL), about 240 μg (6 μg/mL in 40 mL), or about 300 μg (3 μg/mL in 100 mL). In some embodiments, the IL-4 targeted cargo protein is administered as a single dose of about 1.5 μg/mL to about 3 μg/mL.

In some embodiments, the dosing is 180 μg, or 3 μg/mL × 60 mL, of PRX 321 per subject. In some embodiments, the dosing is from about 1.5 μg/mL to about 3.0 μg/mL. In some embodiments, the dosing is about 1.5 μg/m, 2 μg/mL, 2.5 about 3.0 μg/mL or about 3.5 μg/mL In some embodiments, the dosage is for any IL-4 targeted cargo protein described herein. mL. In some embodiments, the dosage is for PRX 321.

In some embodiments, the dosing flow rate is about 5 μL/min/catheter to about 20 μL/min/catheter. In some embodiments, the dosing flow rate is about 10 μL/min/catheter to about 15 μL/min/catheter. In some embodiments, the dosing flow rate is about 15 μL/min/catheter. In some embodiments, 1-4 catheters are employed. In some embodiments, 1-3 catheters are employed. In some embodiments, 1-3 catheters are employed and the flow-rates of up to 15 μL/min/catheter. In some embodiments, 1.5 g/mL is administered via 1-3 catheters and the flow-rates of up to 15 μL/min/catheter. In some embodiments, 1.5 μg/mL is administered via 1-3 catheters and the flow-rates of up to 15 μL/min/catheter with a total dosage of 90 μg of PRX 321.

E. Convection Enhanced Delivery (CED)

The present invention contemplates the use of CED for delivery of therapeutics directly into the tumor. CED has been described in Patel et al., Neurosurgery 56:1243-52, 2005, (incorporated by reference herein in its entirety). This enables high local drug concentrations to be achieved while limiting systemic toxicity. The procedure has been used in the treatment of recurrent GB and other CNS disorders from early clinical development through to Phase 3 clinical trials with a good safety profile. In some embodiments, PRX 321 is delivered by convection-enhanced delivery (CED) intratumorally. In some embodiments, CED is performed by direct infusion through intracranial catheters (1 or more, depending on the size of the tumor) under constant pressure. In some embodiments, this is over a period of 1 to 7 days. The total dose of PRX 321 is about 90-100 μg. In some embodiments, the dosage can be adjusted within the range of range 5 μg to 1 mg. In some embodiments, MRI imaging prior to, during and following infusion is used to monitor drug distribution and tumor response. In some embodiments, subjects/patients are monitored by clinical evaluation and MRI on an ongoing basis after treatment.

In some embodiments, CED will be employed to administer the IL-4 targeted cargo proteins to the CNS tumor. In some embodiments, CED will be employed to administer PRX 321 for the treatment of CNS tumors. In some embodiments, CED will be employed to administer PRX 321 for the treatment of GB. In some embodiments, CED will be employed to administer PRX 321 for the treatment of progressive and/or recurrent GB.

In some embodiments, the CED process will employ the use of planning high precision planning software (e.g. iPlan® Flow Infusion Version 3.0.6, Brainlab AG) for determining catheter placement. In some embodiments, the CED process will employ catheters specifically designed for brain usage. In some embodiments, the CED process will not employ large diameter ventricular catheters, which can be prone to drug leakage from the intended delivery site (see, for example 3).

In some embodiments, the CED process will include co-infusion of a surrogate tracer, for example, a magnetic resonance imaging (MRI) contrast agent, will allow real-time monitoring of PRX 321 distribution ensuring adequate coverage of the tumor and the infiltrative edges.

In some embodiments, the surrogate tracer molecule can include but is no limited to any magnetic resonance imaging tracer. In some embodiments, the surrogate tracer is a gadolinium bound tracer. In some embodiments, the surrogate tracer is selected from the group consisting of gadolinium-diethylenetriamine pentaacetic acid [Magnevist®] [Gd-DTPA]; commercially available from Bayer Healthcare Pharmaceuticals, Inc.) and gadolinium-bound albumin (Gd-albumin). In some embodiments, the surrogate tracer used during CED will enable effective real-time monitoring of drug distribution. In some embodiments, the real-time monitoring allows for ensuring adequate coverage of the tumor and the peritumoral infiltrating margin with the IL-4 targeted cargo protein, including for example, PRX 321. In some embodiments, the surrogate tracer can be administered in combination with the targeted cargo protein to determine if the targeted cargo protein is delivered to a tumor, such as a brain tumor, safely at therapeutic doses while monitoring its distribution in real-time.

For further information regarding on CED and surrogate tracers, see for example, Chittiboina et al., 2014; Jahangiri et al., 2016; and Murad et al., Clin. Cancer Res. 12 (10): 3145-51, 2006), all of which are incorporated herein by reference in their entireties.

F. Monitoring Treatment

Any in vitro or in vivo (ex vivo) assays known to one of ordinary skill in the art that can detect and/or quantify cancer cells and/or cancer stem cells can be used to monitor cancer cells and/or cancer stem cells in order to evaluate the impact of a treatment utilizing a IL-4 targeted cargo protein. These methods can be used to assess the impact in a research setting as well as in a clinical setting. The results of these assays then may be used to alter the targeting moiety, cargo protein or alter the treatment of a subject. Assays for the identification of cancer cells and/or cancer stem cells are provided in US patent application no. 2007/0292389 to Stassi et al. (herein incorporated by reference).

Cancer cells and/or cancer stem cells usually are a subpopulation of tumor cells. Cancer cells and/or cancer stem cells can be found in biological samples derived from cell culture or from subjects (such as a tumor sample). Various compounds such as water, salts, glycerin, glucose, an antimicrobial agent, paraffin, a chemical stabilizing agent, heparin, an anticoagulant, or a buffering agent can be added to the sample. The sample can include blood, serum, urine, bone marrow or interstitial fluid. In another example, the sample is a tissue sample. In a particular example, the tissue sample is breast, brain, skin, colon, lung, liver, ovarian, pancreatic, prostate, renal, bone or skin tissue. In a specific example, the tissue sample is a biopsy of normal or tumor tissue. The amount of biological sample taken from the subject will vary according to the type of biological sample and the method of detection to be employed. In a particular example, the biological sample is blood, serum, urine, or bone marrow and the amount of blood, serum, urine, or bone marrow taken from the subject is 0.1 mL, 0.5 mL, 1 mL, 5 mL, 8 mL, 10 mL or more. In another example, the biological sample is a tissue and the amount of tissue taken from the subject is less than 10 milligrams, less than 25 milligrams, less than 50 milligrams, less than 1 gram, less than 5 grams, less than 10 grams, less than 50 grams, or less than 100 grams.

A test sample can be a sample derived from a subject that has been treated with a IL-4 targeted cargo protein. Test samples can also include control samples. In some examples a control sample is from a subject prior to treatment with a IL-4 targeted cargo protein and in other examples the test sample can be taken from a different location within a subject that has been treated with a IL-4 targeted cargo protein. Control samples can also be derived from cells that have been artificially cultured. The sample can be subjected to one or more pretreatment steps prior to the detection and/or measurement of the cancer stem cell population in the sample. In certain examples, a biological fluid is pretreated by centrifugation, filtration, precipitation, dialysis, or chromatography, or by a combination of such pretreatment steps. In other examples, a tissue sample is pretreated by freezing, chemical fixation, paraffin embedding, dehydration, permeabilization, or homogenization followed by centrifugation, filtration, precipitation, dialysis, or chromatography, or by a combination of such pretreatment steps. In certain examples, the sample is pretreated by removing cells other than stem cells or cancer cells and/or cancer stem cells from the sample, or removing debris from the sample prior to the determination of the amount of cancer cells and/or cancer stem cells in the sample.

In certain examples, the amount of cancer cells and/or cancer stem cells in a subject or a sample from a subject is/are assessed prior to therapy or regimen to establish a baseline. In other examples the sample is derived from a subject that was treated using a IL-4 targeted cargo protein. In some examples the sample is taken from the subject at least about 1, 2, 4, 6, 7, 8, 10, 12, 14, 15, 16, 18, 20, 30, 60, 90 days, 6 months, 9 months, 12 months, or >12 months after the subject begins or terminates treatment. In certain examples, the amount of cancer cells and/or cancer stem cells is assessed after a certain number of doses (e.g., after 2, 5, 10, 20, 30 or more doses of a therapy). In other examples, the amount of cancer cells and/or cancer stem cells is assessed after 1 week, 2 weeks, 1 month, 2 months, 1 year, 2 years, 3 years, 4 years or more after receiving one or more therapies.

Targets on cancer cells and/or cancer stem cells are also expressed on normal non-cancerous cells. Therefore, in some examples the identification of cancer cells and/or cancer stem cells can be made by comparing the relative amount of signal generated from target binding in a control sample and comparing it to the test sample for which the presence or absence of cancer cells and/or cancer stem cells is being determined. In such examples, the number, quantity, amount or relative amount of cancer cells and/or cancer stem cells in a sample can be expressed as the percentage of, e.g., overall cells, overall cancerous cells or overall stem cells in the sample.

The results from testing a sample for the presence of cancer cells and/or cancer stem cells and/or the amount of cancer cells and/or cancer stem cells present can be used to alter treatment regimes, including altering the variety of IL-4 targeted cargo protein used. For example, if testing before and after treatment reveals that the population of cancer cells and/or cancer stem cells increased and/or did not decrease treatment can be altered. For example, the dosage of the therapeutic can be altered and/or a IL-4 targeted cargo protein designed to target distinct target can be substituted or added to the treatment regime.

The amount of cancer cells and/or cancer stem cells can be monitored/assessed using standard techniques known to one of ordinary skill in the art. Cancer cells and/or cancer stem cells can be monitored by obtaining a sample, and detecting cancer cells and/or cancer stem cells in the sample. The amount of cancer cells and/or cancer stem cells in a sample (which may be expressed as percentages of, e.g., overall cells or overall cancer cells) can be assessed by detecting the expression of antigens on cancer cells and/or cancer stem cells. Any technique known to those skilled in the art can be used for assessing the population of the cancer cells and/or cancer stem cells. Antigen expression can be assayed, for example, by immunoassays including, but not limited to, western blots, immunohistochemistry, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, immunofluorescence, protein A immunoassays, flow cytometry, and FACS analysis. In such circumstances, the amount of cancer cells and/or cancer stem cells in a test sample from a subject may be determined by comparing the results to the amount of stem cells in a reference sample (e.g., a sample from a subject who has no detectable cancer) or to a predetermined reference range, or to the patient him/herself at an earlier time point (e.g., prior to, or during therapy). For the purposes of immunoassays one or more of the targets displayed by the cancer stem cell can be used as the target for the immunoassay.

For example, brain cancer cells and/or cancer stem cells can be identified using a CD133+ target, as well as other targets known to be expressed on brain cancer cells and/or cancer stem cells. Additional exemplary markers can be found in Sakariassen et al., Neoplasia 9 (11): 882-92, 2007 and Vermeulen et al., Cell. Death Differ. 15 (6): 947-58, 2008 and U.S. patent application 2008/0118518, which is herein incorporated by reference.

G. Therapeutic Variations

One of ordinary skill in the art will appreciate that targets on cancer cells and/or cancer stem cells can also be expressed on normal healthy cells. For example, CD133 was initially shown to be expressed on primitive hematopoietic stem and progenitor cells and retinoblastoma and then subsequently shown to be expressed on cancer cells and/or cancer stem cells. Therefore, in some examples where a cancer stem cell target is expressed on a class of non-cancerous cells therapy can involve removal of a population of the non-cancerous cells followed by IL-4 targeted cargo protein treatment directed to the cancer stem cell of interest and then reintroducing the non-cancerous cells expressing the target.

In another example, healthy populations of cells that express the same target as that of a cancer stem cell population are protected through the use of two or more IL-4 targeted cargo proteins. A first IL-4 targeted cargo protein is engineered to target a first cancer stem cell target (e.g., CD133). The cargo protein that is included in the first IL-4 targeted cargo protein can be a toxin that is in an inactive form. A second IL-4 targeted cargo protein is engineered to target a second target on the cancer stem cell (e.g., CD24). This second IL-4 targeted cargo protein includes a protein sequence capable of activating the first IL-4 targeted cargo protein. Thus, only a cancer stem cell that expresses the targets for both the first IL-4 targeted cargo protein and the second cargo protein will receive the therapeutic activity of the cargo moiety.

In another therapeutic variation the subject is treated with an agonist to the target displayed on the cancer stem cell. The cancer cells and/or cancer stem cells then display an increased level of the target. The treatment with the agonist can then be administered before, during or after administration of the IL-4 targeted cargo protein. One of ordinary skill in the art will appreciate that the exact timing of administration will depend upon the specific agonist chosen and the specific IL-4 targeted cargo protein.

EXAMPLES

Example 1: Treatment of Recurrent or Progressive Glioblastoma with PRX 321

An Open-Label Non-Randomized, Multi-Center Phase-2 Study of Convection-Enhanced Delivery (CED) of PRX 321 in Adults with Recurrent or Progressive Glioblastoma Rationale:

PRX 321 is a fusion toxin comprising a genetically engineered circularly permuted interleukin-4 (cpIL-4) fused to a modified version of the *Pseudomonas aeruginosa* exotoxin A (PE). PRX 321 binds to the IL-4 receptor (IL-4R), over-expressed by cancer cells and non-malignant immunosuppressive cells of the tumor micro-environment (TME), and delivers a potent cell-killing agent, PE. A large percentage of glioblastomas (GBs) and their TME express IL-4R in relatively high amounts, making it a relevant target for PRX 321. Intra- and peritumoral infusion minimizes systemic exposure to the fusion toxin, while the image-guided CED technique enhances exposure of active drug throughout the target region. PRX 321 shares many properties with immunotherapies, such as immune checkpoint inhibitors, including the possibility of response following a prolonged (>3 months) period of pseudo-progression. In this study, standard Response Assessment in Neuro-Oncology (RANO) criteria will be used for evaluating recurrence/progression after prior therapy in assessment of prospective patient eligibility, while modified RANO criteria will be used for post treatment follow-up to assess response and progression.

Study Objectives:

Primary

To determine the objective response rate (ORR) per a modified RANO criteria following an intra- and peritumoral infusion of PRX 321 using CED relative to pre-operative planning MRI (baseline)

Secondary

To assess the safety of PRX 321 following CED

To assess overall survival (OS)

To assess progression-free survival (PFS; using modified RANO criteria)

Exploratory

To assess the pharmacokinetics (PK) of PRX 321 in peripheral plasma

To assess serum anti-PRX 321 antibody titers and, if elevated, determine neutralizing antibody titers To perform additional ad hoc efficacy and safety analyses as needed based on the data acquired in this study.

Key Enrollment Criteria:

In order to be eligible to participate in this study, male and female subjects ≥18 years of age must have primary (de novo) GB that has recurred or progressed (per standard RANO criteria), a life expectancy >12 weeks and a Karnofsky performance status (KPS)≥70.

Subjects must have tumor diameter of ≥1 cm x≥1 cm (minimum) to 4 cm in any direction by pre-interventional magnetic resonance imaging (MRI); within 14 days of planned treatment) and not have features which make the tumor a poor target for CED (e.g. significant liquefaction or geometric features not conducive to CED).

Study Design:

This is a single-arm, open-label, multicenter study in approximately 52 adults with GB that has recurred or progressed (according to standard RANO criteria). The study will be conducted at up to 12 clinical sites following institutional review board approval and completion of informed consent.

Eligible subjects will undergo surgery associated with study drug administration. PRX 321 infusate will be administered with the objective of achieving coverage of the tumor and the peritumoral margin to the maximum extent possible as indicated by distribution of a co-infused gadolinium tracer observed by MRI. Pre-treatment catheter trajectory planning will be performed with aim to place 4 catheters with as many as possible but ordinarily a minimum of 2 catheters located in the enhancing tumor tissue, except in the smallest tumors where this is not feasible. Any remaining catheter(s) should be placed outside of enhancing tumor, within the T2 flair signal area and ≤2 cm from the enhancing rim of the tumor. The intended volume of infusion (Vi) will be 60 mL resulting in a total dose of 180 µg PRX 321 (3 µg/mL×60 mL).

Infusion via each catheter will be initiated at the rate of 3 µL/min/catheter and gradually increased in a stepwise manner. The infusion flow rate will be adjusted at the discretion of the Investigator during at least the first 3 hours of the infusion, during which time distribution of the infusate will be monitored by real time MRI (with subject maintained under anesthesia). The total flow rate of all functioning catheters should not exceed 50 µL/min and all functioning catheters should be convecting at similar flow rates. After the real-time MRI infusion monitoring period is completed, the remainder of the infusion will continue with the subject awake. An MRI will be performed upon completion of infusion as a final evaluation of PRX 321 infusate distribution.

A Safety Review Committee (SRC) conducted a safety and infusate-distribution data review after the first 6 subjects were treated on study. Adjustments to the treatment parameters were recommended to enhance drug delivery whilst remaining well within the established safety profile, nevertheless a further safety review will be completed 30 days after 6 subjects have been treated according to this revised dose regime. Changes to the protocol following this amendment will be submitted for approval to appropriate regulatory agencies and IRBs prior to implementation. All subjects under protocol versions 1.0, 2.0 and 3.0 will be included in efficacy and safety analyses. Enrollment will be extended to supplement the cohort with additional subjects under protocol version 3.0 with enhanced drug delivery, to enable subset and sensitivity analyses to be conducted.

Post-treatment follow-up assessment of safety will be performed 14 days after infusion. Thereafter, efficacy and safety assessments will be performed at 30, 60, 90, 120, 180, 240, and 360 days after infusion. Subjects who discontinue before the Day 360 visit will undergo all the procedures scheduled for the Day 360 visit at the time of discontinuation.

Subjects who complete the Day 360 study follow up visit without disease progression or discontinue early without disease progression will continue to be followed for disease status until progression where possible. After progression (on study or during post-study follow-up), subjects will continue to be followed for survival and post-study treatment(s) for GB and imaging for GB, where possible, until death (or termination of data collection by the Sponsor or withdrawal of consent by the subject).

Drug and Routes of Administration:

PRX 321 drug product is supplied as a sterile frozen solution at a concentration of 500 µg/mL in 0.5 mL phosphate buffered saline, filled in a sterile, single-use, 2 mL Type 1 USP depyrogenated clear glass vial sealed with 13 mm Teflon-faced stopper and labeled according to country-specific regulatory requirements.

For clinical use, PRX 321 drug product will be diluted in Elliotts B® solution to produce an infusate with a final composition of PRX 321 (3 µg/mL), 0.02% human serum albumin and gadolinium-diethylenetriamine pentaacetic acid (Gd-DTPA, Magnevist®) (7 mM). The infusate is prepared at the hospital pharmacy and instructions for its preparation are provided in the Pharmacy Manual.

PRX 321 is administered via intra- and peritumoral infusion using CED with precision planning and real-time MRI monitoring of infusate distribution.

Dosage & Frequency:

Each subject will receive a single administration of PRX 321 at a fixed concentration of 3.0 µg/mL with infused volume of 60 mL administered via up to 4 surgically placed catheters.

Duration of infusion is expected to range between 24 to 36 hours; however, it may continue for up to 48 hours, if needed for completion.

Efficacy Points:
Primary
ORR as determined by an independent central review (Imaging Core Lab) according to modified RANO criteria, as assessed by gadolinium-enhanced MRI approximately 30, 60, 90, 120, 180, 240, and 360 days post-infusion relative to pre-treatment baseline MRI (acquired for treatment planning prior to catheter placement).

Secondary
OS, defined as the time from treatment until death.
PFS, defined as the time from treatment until disease progression (per modified RANO criteria and as determined by an independent central review) or death.

Other
Duration of response (DOR), defined as the time from first response until disease progression (per modified RANO criteria and as determined by an independent central review) or death among those subjects achieving a complete response (CR) or partial response (PR) to treatment.

Duration of clinical benefit (DOCB), defined as the time from first response or disease stabilization until disease progression (per a modified RANO criteria and as determined by an independent central review) or death among those subjects achieving a complete response (CR), partial response (PR), or stable disease (SD)

Additional, exploratory, efficacy analyses may include ORR and PFS based on the Investigator's assessment of response, other time-to-event endpoints (e.g., time to post-study treatment of GB) and exploration of response according to biomarker status.

Safety Points:
Include: serious adverse events (SAEs) and treatment emergent adverse events (AEs); Clinical laboratory results; Physical and neurological examinations; KPS; and Electrocardiogram (ECG).

Additional, exploratory, safety analyses may include specific AEs of interest and the relationship of safety to plasma PRX 321 pharmacokinetic (PK) parameters and/or evaluation of immune parameters.

Other Endpoints
These include: PRX 321 PK parameters in peripheral plasma; Anti-PRX 321 antibody titer in serum; and Neutralizing antibody titer (if elevated anti-PRX 321 titer is observed).

Statistical Analyses:
Subject Populations:
IL-4R Analysis Population
The IL-4R analysis population will be the same as the mITT Population and will be used for efficacy analyses stratified by IL-4R levels.

Safety Population
The Safety population will comprise all subjects treated on study. Safety analyses will be presented on this population.

Analyses:
The primary efficacy analysis, conducted on the mITT population will include all patients evaluable on study from all protocol versions and will be assessed according to a single-arm, single-stage binomial design with primary hypothesis test comparing a null response rate of 6% with an alternative (pursue further study) rate of 18%, at 1-sided alpha=0.10.

The secondary analysis of the primary endpoint using the same hypotheses and alpha will be conducted on the subjects enrolled under Protocol Version 3.0 onwards, including patients treated similarly under previous protocol versions.

These primary and secondary analyses will be conducted in a fixed sequence, primary first. The secondary analysis will be descriptive only in case the primary analysis fails to reach statistical significance. This will control the overall trial false positive rate at 10% (one-sided).

With 36 mITT subjects there will be approximately 80% power for the secondary test and, with more than 36 mITT subjects pooled, more than 80% power for the primary test; accounting for approximately 10 to 15% non-evaluable, it is planned to enroll a total of 52 subjects in the trial, including approximately 35 under Protocol Version 3.0.

OS and PFS will be determined via Kaplan-Meier estimation, with medians, quartiles, and 95% confidence intervals (CIs) reported. Descriptive analysis of the OS and PFS at 6, 9, and 12 months after treatment will be based on the raw proportions of subjects surviving (and progression-free) at those time points as well as Kaplan-Meier estimation. Analyses will also be conducted by IL-4R stratum, including 95% confidence interval estimates of ORR within strata and examination of the treatment effect by IL-4R level.

Efficacy analyses may also explore subject subsets (e.g. IL-4R level, tumor size, KPS, gender, age, steroid use) and response by other applicable criteria.

Descriptive statistics will be provided for subject demographics and disposition, safety, and exposure data and will include the number of observations, mean, standard deviation, median, and range for continuous variables and number and percent for categorical variables; 95% CIs will be presented where appropriate.

Introduction

The study drug, PRX 321, is a fusion protein consisting of a targeting domain linked to a pro-apoptotic cell-killing payload. It was discovered and developed by Drs. Raj Puri (United States [US] Food and Drug Administration [FDA]) and Ira Pastan (National Cancer Institute "NCI") and has been described by various researchers in over 50 publications. It is a therapeutic agent that selectively targets cancer cells that over-express the interleukin-4 receptor (IL-4R).

The targeting domain is an engineered circularly permuted version of interleukin-4 (cpIL 4) which is genetically fused to potent payload comprised of a truncated version of the bacterial toxin, Pseudomonas aeruginosa exotoxin (PE) A (Kreitman et al., 1994). It was developed for the treatment of glioblastoma (GB) and other adult and pediatric central nervous system (CNS) cancers including immunosuppressive cells of the glioblastoma tumor microenvironment (TME) that frequently over-express the IL-4 receptor (IL-4R; Puri et al., 1994; Kohanbash et al., 2013).

The mechanism of action of PRX 321 is well documented (Kreitman et al., 1994; Rand et al., 2000; Puri et al., 2009) and is depicted in FIG. 1. PRX 321 binds to IL-4R overexpressed on the surface of tumor cells and the entire complex is endocytosed. Following cleavage and activation by furin-like proteases found in high concentrations in the endosome of cancer cells, the catalytic domain of the truncated PE is released into the cytosol where it induces cell death via adenosine diphosphate (ADP)-ribosylation of the Elongation Factor-2 and induction of apoptosis through caspase activation (Shapira and Benhar, 2010).

Many features of PRX 321 make it a rational choice for the treatment of GB and other primary and metastatic tumors in the CNS:

The majority of cancer biopsy and autopsy samples from adult and pediatric CNS tumors, including recurrent GB biopsies, have been shown to over-express the IL-4R with little or no IL-4R expression in normal adult and pediatric brain tissue (Puri et al., 1996; Kawakami et al., 2002; Joshi, et al., 2001; Konanbash et al., 2013). Cells that do not express the IL-4R target do not bind to PRX 321 and are, therefore, not subject to PE-mediated effects (Kawakami et al., 2002; Puri et al., 2005).

Unlike chemotherapeutic agents and radiation, PRX 321's cell-killing ability is not growth-rate dependent (Li and Hall, 2010). Due to its mechanism of action, quiescent cancer cells and/or cancer stem cells and slower growing non-malignant cells of the TME may be as sensitive to PRX 321 as rapidly dividing tumor cells.

06-methylguanine-methyltransferase (MGMT) positive cancer cells (harboring unmethylated MGMT promoters and therefore resistant to temozolomide) are sensitive to PRX 321. CNS and non-CNS cancer cell lines such as T98G (glioblastoma), HT-29 (colon cancer), and Mia-Paca-2 (pancreatic cancer) are known to over-express MGMT and are resistant to alkylating agents such as temozolomide (Huang et al., 2012; Kuo et al., 2007; Kokkinakis et al., 2003). However, these IL-4R-expressing cell lines show picomolar sensitivity to PRX 321 (Puri et al., 1996; Kreitman et al., 1995; Shimamura et al., 2007), indicating that PRX 321 could provide a treatment option for MGMT positive GB patients.

Furin-like proteases are required for cleavage of PRX 321 and activation of the PE toxin (Chironi et al., 1997; Shapira and Benhar, 2010). High expression levels of furin in targeted glioma cells as opposed to normal cells (Mercapide, et al., 2002; Wick et al., 2004) provides additional tumor specificity and is also a contributory factor to the exceptional picomolar sensitivity of cancer cells to PRX 321.

The pro-apoptotic domain of PRX 321 (i.e., PE) is far more potent than chemotherapeutic agents (Li and Hall, 2010). It kills cancer cells by arresting protein synthesis (Shapira and Benhar, 2010), a mechanism not employed by other anti-cancer agents.

Internalization of PRX 321 into the target cell occurs via a mechanism that is independent of p-glycoprotein (P-gp), a membrane associated protein that is commonly used to transport chemotherapeutic drugs. Mutations in P-gp often lead to cancer cells becoming resistant to traditional chemotherapeutic drugs, a problem not expected with PRX 321 since it does not rely on P-gp for entry into the cell (Strome et al., 2002; de Jong et al., 2003).

GB has a robust immunosuppressive TME and may comprise up to 40% of the tumor mass (Kennedy et al., 2013). Recently, it has been shown that malignant gliomas have a T-helper cell type-2 (Th2) bias and are heavily infiltrated by myeloid derived suppressor cells (MDSCs) and tumor associated macrophages (TAMs) and that the IL4/IL-4R bias mediates their immunosuppressive functions (Harshyne, et al., 2016). Furthermore, IL-4R is up-regulated on glioma-infiltrating myeloid cells but not in the periphery or in normal brain (Kohanbash et al., 2013). Thus, purging Th2 cells, MDSCs, and TAMs using PRX 321 may alleviate the immune block associated with cancer (in a manner similar to immunomodulators such as ipilumimab, pembrolizumab or nivolumab), thereby promoting anti-tumor immunity and aid in long-term disease control.

Safety of PRX 321 has been adequately characterized in non-clinical studies. In addition, safety and efficacy of PRX 321, administered as a single dose by local intra- and peritumoral infusion via convection-enhanced delivery (CED) has been evaluated in a total of 72 adults with high grade recurrent gliomas (including 66 adults with recurrent GB) in three prior clinical studies. All nonclinical and clinical studies conducted to date are summarized in the Investigator's Brochure (Edition 10).

Although not designed for efficacy, the Phase 1/2 clinical studies in adults with recurrent GB treated with PRX 321 generated sufficient data during and post-study to warrant supplemental analysis of tumor response, survival and the effect of tumor response on survival outcomes.

By implementing recent advances in CED, a multi-center, single-arm, open-label study will be carried out in approximately 52 patients with GB at recurrence or progression who will receive PRX 321 via intra- and peritumoral infusion using CED. The efficacy of PRX 321 will be investigated with subjects having tumor diameter of ≥1 cm x≥1 cm (minimum) to 4 cm in any direction, no more than 2 relapses, and a Karnofsky score of ≥70 which are consistent with the inclusion criteria used in recent clinical trials for recurrent GB. Of note, the IL-4R tumor expression profile, of subjects treated with PRX 321 in prior clinical studies was not determined. In this study, a retrospective analysis of IL-4R expression of the archived tissue obtained at first diagnosis of GB will be conducted to determine the role of the IL-4R biomarker on treatment response and patient outcome. Additionally, planning software will be utilized to optimize catheter placement (Rosenbluth et al., 2012) and small diameter catheters with a stepped design will be used to significantly reduce reflux along the catheter tract (Jahangiri et al., 2016; Krauze et al., 2005b) in order to improve intra- and peritumoral distribution of PRX 321. Furthermore, co-infusion of a surrogate tracer (gadolinium-diethylenetriamine pentaacetic acid [Magnevist®] [Gd-DTPA]) during CED will enable effective real-time monitoring of drug distribution thereby optimizing coverage of the tumor and the peritumoral infiltrating margin with PRX 321 (Chittiboina et al., 2014; Jahangiri et al., 2016).

Use of the latest CED technologies and real-time imaging has the potential to improve PRX 321 distribution, its safety as well as patient outcomes.

Treatment of Recurrent or Progressive GB

Standard first-line treatment for primary GB includes surgical resection of the bulk tumor to the maximal extent possible consistent with neurological preservation, followed by radiotherapy, often in combination with temozolomide (Stupp protocol; Stupp et al., 2005). When relapse or progression occurs in patients who have undergone the Stupp protocol, therapeutic options are unfortunately limited and generally not effective.

Surgery may be indicated in a minority of relapsed patients with disease that is symptomatic from mass effect, but it results in only limited prolongation of survival (Keles et al., 2004). Survival may be improved by combining surgery with the Gliadel® (carmustine) implant. However, the majority of patients with relapsed disease are not candidates for additional surgery (Weller et al., 2013). Thus, the use of Gliadel is limited as surgery is required for Gliadel administration.

Avastin® (bevacizumab) has been seen to improve 6-month progression free survival (PFS) to 42.6% and increase in median overall survival to 9.3 months in patients with recurrent GB. Genentech received accelerated approval from the US FDA for Avastin, in patients with recurrent GB patients who had failed first-line chemotherapy, based on an overall response rate of 28% (Friedman et al., 2009).

Despite these agents, there is an urgent need for more effective targeted therapies for the treatment of recurrent GB. Intra- and peritumoral infusion via CED of targeted fusion toxin, such as PRX 321, is a promising novel tumor-specific therapeutic for the treatment of this disease.

PRX 321 efficacy compares favorably to published data for Gliadel and Avastin (Brem et al., 1995, Cohen et al., 2009) despite the fact that nearly half of the patients treated with PRX 321 in previous clinical trials had multiple relapses prior to their enrolment, compared to one fifth of the Avastin cohort (see Investigator's Brochure Edition 10 for detail). Table 9 compares objective tumor response rate of PRX 321 vs. published reports for Avastin (Freidman et al., 2009). It is notable that the complete response rate was 20% in the PRX 321 treated patients and 1.2% in the Avastin treated group.

TABLE 9

Objective Response Rates for Non-Resected Recurrent GB Patients Treated with PRX 321

| Patient Characteristics | Avastin* (n = 85) | PRX 321** (n = 25) |
|---|---|---|
| Average age | 54 | 54 |
| Patients with >1 relapse | 19% | 48% |
| Karnofsky Performance Status ≥ 70 | 100% | 88% |
| Overall response rate (partial + complete responders) | 28% | 56% |
| Complete responders | 1.2% | 20% |

*Published Data (Avastin Data: Freidman et al., 2009);
**Single Treatment (Investigator's Brochure Edition 10)

Targeted Intratumoral Therapy
Fusion Toxins

Fusion toxins fall into the category of targeted therapy and generally consist of highly potent bacterial or plant toxin moieties (payloads) fused to tumor-specific ligands (targeting domains). They represent a novel anti-cancer modality that may offer several advantages over conventional therapies. One such novel fusion toxin in development is PRX 321. Fusion toxins such as PRX 321 take advantage of the selective expression of receptors (e.g., IL-4R) on tumor cells, cancer cells and/or cancer stem cells (CSCs) and tumor microenvironment (TME) (safety and tolerability) with the effectiveness of potent toxins (anti-tumor efficacy). The function of the targeting domain of PRX 321 (i.e., IL-4) is "to guide" the toxin specifically to the tumor cells while sparing normal cells. Fusion toxins such as PRX 321, directed at tumor specific targets therefore, exhibit a relatively wide therapeutic index when compared to conventional chemotherapeutic agents.

PRX 321 has the Following Unique Characteristics:

Induces tumor shrinkage independent of growth rate. Quiescent CSCs, slow growing cells of the TME and rapidly dividing cancer cells are equally sensitive at the picomolar range (Hall et al., 1992)

Uses a multi-pronged approach to cancer therapy. PRX 321 is able to simultaneously target bulk tumor, deplete CSCs (Merchant et al., 2015) and may also purge TAMs and MDSCs, key components of the TME (Bankaitis and Fingleton, 2015)

New understanding of the role played by the TME in protecting cancer indicates that targeting cancer cells alone will not significantly alter survival outcomes. With a multi-pronged approach, PRX 321 may therefore provide an overall meaningful and durable long-term response in CNS tumors that over-express the IL-4R.

Interleukin-4 Receptors as a Drug Target for GB

The study drug, PRX 321, was developed for the treatment of recurrent GB, as various types of CNS tumors have been known to frequently over-express the IL-4R and available data demonstrate that a large percentage of GBs express the IL-4R at relatively high levels (Puri et al., 1994; Puri et al., 1996; Joshi et al., 2001; Joshi et al., 2002). Detailed information on IL-4R as a drug target for GB including recent studies evaluating IL-4R expression in matched biopsy samples of newly diagnosed and recurrent GB obtained from the same patient are provided in the Investigator's Brochure (Edition 10). These data indicate that GB patients continue to express the IL-4R at recurrence and in some cases, at much higher levels.

Convection Enhanced Delivery

PRX 321 is a large fusion protein (53 kDa) and as such is not able to cross the blood brain barrier (BBB). In order to by-pass the BBB, localized delivery techniques such as convection enhanced delivery (CED) are being widely developed for CNS diseases. CED improves drug delivery to brain tumors intraparenchymally by utilizing bulk flow, or fluid convection, established as a result of a pressure gradient, rather than a concentration gradient (Yin et al., 2011). As such, CED offers markedly improved distribution of infused therapeutics within the CNS compared to direct injection or via drug eluting polymers, both of which depend on diffusion for parenchymal distribution. Additionally, CED obviates the challenges of systemic agents crossing the BBB while minimizing systemic exposure and toxicity. (Fiandaca et al., 2008; Yin et al., 2011; Vogelbaum and Aghi, 2015). Advantages of CED over diffusion-based delivery include:

Expanded volume of distribution (Vd); volume of distribution being greater than the volume of infusion (Vi);
Uniform concentration of the infused therapeutic within the target volume; and
Delivery of the vast majority of the infused therapeutic within the target volume.

CED distribution is enhanced by the arterial pulsations within the brain's perivascular spaces (Hadaczek et al., 2006). Additionally, better understanding of the complexities of the extracellular matrix and its effects on convection has led to improved distribution (Hamilton et al., 2001; Neeves et al., 2007; Nguyen et al., 2001). For example, technical infusion parameters, such as cannula size and shape, infusion rate, infusate concentration, and tissue sealing time, have been defined and refined to improve distribution of study agents while limiting potential toxicities and morbidities (Morrison et al., 1999; Chen et al., 1999; Wein et al., 2002; Krauze et al., 2005b; Healy and Vogelbaum, 2015; Lewis et al., 2016).

Real-Time Imaging of Convective Delivery

A major advance in the safe and potentially efficacious use of CED in neurosurgery has been the development of real-time imaging of convective delivery (RCD), which utilizes MRI to visualize the CED process with the aid of a co-convected contrast agent (Krauze et al., 2005a; Fiandaca et al., 2009; Nguyen et al., 2003; Krauze et al., 2005b; Murad et al., 2006; Lonser et al., 2007; Chittiboina, et al., 2014; Lonser, et al., 2015). Use of RCD allows physicians to directly monitor distribution of therapeutics within the brain. Thus, reflux along the CED catheter or leakage outside the target area, especially at higher flow rates, can be monitored and corrective steps taken, such as retargeting the catheter or altering the rate of infusion (Fiandaca et al., 2008; Varenika et al., 2008).

The RCD technique will be used in this study and represents an important advancement in drug delivery and distribution in the brain. Earlier clinical trials that did not utilize RCD did not achieve adequate distribution of the study drug, which may have caused the studies to not meet their clinical endpoints (Gill et al., 2003; Marks et al., 2010; Sampson et al., 2010). Use of RCD in this trial will enable direct visualization of the study drug distribution, permit uniform tumor coverage and enhanced contact between target cells (GB and TME) and PRX 321.

In many studies using RCD, the surrogate tracer of choice has been gadolinium. Gd-DTPA (Magnevist®) is a contrast agent manufactured by Bayer Healthcare Pharmaceuticals, Inc., and has been used clinically for many years.

Prior in vitro and in vivo studies (Mardor, et al., 2009; Ding et al., 2010) have shown that Gd-DTPA is biocompatible and safe when co-administered with PRX 321 (see Investigator's Brochure Edition 10). Gd-DTPA, in combination with fusion toxins, has also been safely administered intracerebrally to patients in multiple clinical studies using CED (Lonser et al., 2007; Weber et al., 2003a; Weber et al., 2003b; Sampson, et al., 2011; Chittiboina, et al., 2014). Although gadolinium-based contrast agents are not approved for intracerebral administration, these studies support that Gd-DTPA can be safely administered via infusion in combination with locally administered therapeutics, such as PRX 321.

Clinical Experience with PRX 321

To date, a total of 86 adults have received PRX 321, including 72 adults with high grade glioma.

PRX 321 has been granted orphan drug status by the US FDA and the European Medicines Agency for the treatment of gliomas and Fast Track designation for the treatment of recurrent GB and AA by the US FDA.

Study Rationale

This study is designed to test the hypothesis that ORR is improved to a clinically significant extent with PRX 321 as compared to current available treatments for recurrent/progressive GB. The assumptions regarding response to current treatment are based on ORR data from previous clinical trials in patients with recurrent/progressive glioblastoma. Levin et al. (2015) compiled and reported the case number-weighted mean ORR for clinical studies evaluating cytotoxic agents (21 clinical trials, N=1,745 patients) and non-cytotoxic/non-anti-angiogenic drugs (18 clinical trials, N=1,239). The ORR was 6% (range 0 to 17%) and 4% (range 0 to 9%), respectively, for patients treated with cytotoxic agents or non-cytotoxic/non-anti-angiogenic drugs. Results for non-cytotoxic/anti-angiogenic drugs were better with an ORR rate of 14%. The current design is based on a null hypothesis that ORR is 6% versus the alternative hypothesis that ORR is 18% following treatment with PRX 321.

Dosing

A total of 72 subjects with recurrent or progressive malignant glioma (66 subjects with recurrent GB and 6 subjects with AA) have received intratumoral doses of PRX 321 ranging from 6 µg (0.2 µg/mL×30 mL) to 855 µg (9 µg/mL×95 mL). The highest concentration and volume administered were 15 µg/mL and 185 mL (over 8 days), respectively.

In the first study (investigator initiated study; Rand et al., 2000), 9 subjects with histologically confirmed recurrent GB were infused with PRX 321. Infusion volumes ranged from 30 to 185 mL. Two subjects received more than one treatment. There were four infusions at the 0.2 µg/mL dose, three at the 2.0 µg/mL dose, and five at the 6.0 g/mL dose.

In the Phase 1 study (no resection post-infusion; consistent with the treatment plan for this study), subjects were enrolled in sequential groups with each group receiving an escalating dose: 240 µg (6 µg/mL×40 mL), 360 µg (9 µg/mL×40 mL), 600 µg (15 µg/mL×40 mL) and 900 µg (9 µg/mL×100 mL). Dose limiting toxicities were seen in the 15 µg/mL×40 mL dose group. Consequently, 9 µg/mL×40 mL was initially considered the maximum tolerated dose (MTD). Additional patients were enrolled at the 9 µg/mL×40 mL dosage to gain further experience with the MTD. Dose limiting toxicities were observed in the additional subjects that received the 9 μg/mL×40 mL dose and therefore the MTD was redefined to be 240 μg (6 μg/mL×40 mL).

In the Phase 2 study, PRX 321 was administered at doses of 90 μg (1.5 μg/mL×60 mL), 240 μg (6 μg/mL×40 mL), or 300 μg (3 μg/mL×100 mL) followed by surgical resection 3 weeks post-infusion. No MTD was established in this study.

Therapeutic activity independent of the administered doses or resection post-infusion was observed. Toxicity, on the other hand, appeared to be dose-related in both studies (see Investigator's Brochure Edition 10).

In this study, the total dose for each subject will 180 μg (3 μg/mL×60 mL). The administered volume has been calculated according to the treatment objective of administering sufficient volume of PRX 321 infusate to achieve coverage of the tumor and peritumoral margin for the largest possible 4 cm diameter tumor (assuming an estimated Vd/Vi ratio of 2.0 and a spherical shape). Concentration of PRX 321 in the infusate is set at 3 μg/mL. The proposed concentration of PRX 321 3 μg/mL or higher has already been used safely in 21 subjects in the previous Phase 1 and 2 studies. A total dose of 180 μg (3 μg/mL×60 mL) ensures remaining well within the selected MTD of 240 μg (6 μg/mL×40 mL) from the Phase 1 (N=9) and 2 (N=6) dose escalation studies, even in cases where over 60 mL were to be administered (in error).

Selection of Catheters to be Used for Administration of PRX 321

In earlier clinical studies conducted with PRX 321 and other therapeutic agents, catheters were not designed for effective CED and were prone to reflux and leakage of the therapeutic agent away from the region of interest. In recent years, smaller diameter MRI-compatible catheters with a stepped design have been introduced and have been shown to dramatically reduce reflux along the catheter tract when compared to the large diameter flexible ventricular catheters used in previous GB studies (Krauze et al., 2005b; Rosenbluth et al., 2011; White et al., 2011; Gill et al., 2013; Jahangiri et al., 2016). This has allowed for improved flow rates.

In the US, there are essentially 2 step design catheter options available and both are being and/or have been used in CED studies; these include the Brainlab Flexible Catheter [510 (k) K123605] and the MRI Interventions SmartFlow® Cannula [510 (k) K102101].

The Brainlab catheter is an MRI-compatible flexible catheter that has a rigid stylet design for accurate positioning. This catheter can be left in-place post-surgery and will therefore be employed in this study as it allows continued post-surgical infusion. On the other hand, the SmartFlow® cannula is rigid and can only be used intra-operatively. Like the Brainlab catheter, it is also MRI-compatible, has an identical tip design and is amenable for accurate placement.

Both catheters are intended for single use only and not intended for implantation. PRX 321 infusate (prepared in Elliotts BR solution together with 0.02% HSA and 7 mM of Gd-DTPA) has been tested and shown to be bio-compatible with the Brainlab catheter and all tubing components comprising the infusion assembly and will therefore be used in this study.

Infusion Planning/Catheter Placement Planning

The efficiency of CED in distributing a drug into a tumor depends on correct placement of catheters within the tumor, catheter diameter, flow rate, infusate characteristics, and tissue consistency of the treated area (Wein et al., 2002; Sampson et al., 2007; Jahangiri et al., 2016). An incorrectly placed catheter can lead to the infused drug exiting the tumor through sulci or taking a path of least resistance into the cerebrospinal fluid (CSF), resulting in limited drug exposure of the tumor, and consequently, a lack of efficacy and potential toxicity.

To ensure optimal placement for maximal tumor coverage, Brainlab iPlan® Flow software will be used as the primary tool for generating a pre-treatment plan for placement of catheters (Sampson et al., 2007) prior to infusion. Using MRI of the tumor obtained prior to infusion, the software will be used to predict the optimal trajectory for placement of each catheter, making sure to avoid fissures, sulci, and other elements that can contribute to inadequate distribution. iPlan® software will assist in predicting the placement of the catheter tip according to the catheter placement guidelines, optimizing convection of the infusate and in ensuring safe placement of catheters by avoiding blood vessels, etc.

Using the iPlan®Flow software, pre-treatment catheter trajectory planning will be performed with aim to place 4 catheters with as many as possible, but ordinarily a minimum of 2 catheters, located in enhancing tumor tissue, except in the smallest tumors when this is not feasible or practicable. Any remaining catheter(s) should be placed outside of enhancing tumor tissue, within the T2 flair signal area and ≤2 cm from the enhancing rim of the tumor.

All investigational sites selected for this study have prior CED experience; nevertheless, all sites will be thoroughly trained in the correct use of the catheter, infusion planning, catheter placement and infusion with peer-to-peer support of early cases to ensure consistency across study sites.

Rationale for Infusate Flow Rate

Infusion parameters, such as catheter size and shape, infusion flow rate and infusate concentration, have been defined as factors that have an effect on the efficiency of CED. In previous clinical studies with PRX 321, an infusion flow rate of 10 μL/min/catheter was evaluated (using large diameter ventricular catheters that were not designed for CED) to administer large volumes of infusate over several days.

As discussed above smaller diameter catheters designed specifically for CED of therapeutics into the brain tumor have been developed, which permit higher flow rates with minimal back flow due to their step design Krauze et al. (2005b) and Richardson et al. (2011). As well, recent studies at UCSF (Butowski et al., 2015), showed that 50 μL/min was a safe flow rate without reflux and afforded better manipulation of the dynamics of infusion, allowing for better tumor coverage, especially with larger volumes. Further, Butowski et al. (2015) reported that for efficient CED in brain tumors, the maximum volume of drug should be infused in the shortest possible time. In this study, flow rates will be individualized as use of real-time MRI infusion monitoring will enable the Investigator to determine the optimal flow rate of infusate for each subject.

Although the PRX 321 infusate has shown to be bio-compatible with the Brainlab catheters at flow rates of up to 50 μL/min, the optimal flow rate for effective intra- and peri-tumoral distribution of PRX 321 in vivo via the Brainlab flexible catheter is not established and may vary from patient to patient due to tumor heterogeneity. Therefore, the rate of infusion will be conservatively assessed whereby the flow rate will be initiated at 3 μL/min/catheter and gradually increased in a stepwise manner. The infusion flow rate will be adjusted at the discretion of the Investigator during at least the first 3 hours of infusion during which time distribution of the infusate will be monitored by real time MRI (with subject maintained under anesthesia). The total flow rate of all functioning catheters will not exceed 50 μL/min and all functioning catheters should be convecting at similar flow rates. After real-time MRI infusion monitoring period is completed, the remainder of the infusion will continue with the subject awake. The rate of infusion may be reduced by 50% or stopped and restarted at the discretion of the Investigator if the subject shows signs of intolerance.

Real-Time Imaging of Infusate Distribution

NeoPharm conducted a study from 2004 to 2006 using an IL-13-PE fusion protein (cintredekin besudotox, CB), to target the IL-13 decoy receptor, IL 13Ralpha2, known to be over-expressed in GB. This was a randomized Phase 3 trial of GB patients at first recurrence in which CED was used to locally administer CB following surgical resection of the tumor. CB did not show survival advantage when compared to Gliadel (Kunwar et al., 2010).

Several reasons have been proposed to explain the lack of efficacy of CB (Chandramohan et al., 2012; Jarboe et al., 2007; Sampson et al., 2010).

The trial did not include real-time imaging to ascertain if the required amount of drug was delivered to the tumor site (Sampson et al., 2010).

The estimated coverage of relevant target volumes was low, so that only 20.1% of the penumbra surrounding the resection cavity was covered (Chandramohan et al., 2012).

Post-trial analysis on catheter positioning revealed only 49.8% of catheters met all positioning criteria (Chandramohan et al., 2012).

Thus, even where IL-13Ralpha2 was present in the tumor (Jarboe et al., 2007), delivery of the drug to the tumor target was suboptimal. These results highlight the need for real-time imaging to assess catheter placement and drug distribution.

The objective in this study will be to achieve maximal coverage of the tumor and peritumoral margin. Therefore, real-time imaging of drug distribution, through co-infusion of a tracer will be employed as a means of assessing infusate distribution.

Preclinical studies using PRX 321 were carried out to evaluate the effect of the imaging agent Gd-DTPA in combination with various concentrations of PRX 321 (Ding et al., 2010) and human serum albumin (HSA) administered by direct infusion into rat brains via CED. Results showed that the addition of Gd-DTPA (7 µmol/mL) was well tolerated and that Gd-DTPA did not affect the potency of PRX 321. Feasibility of safely co-infusing Gd-DTPA as a surrogate tracer has been demonstrated in a number of clinical studies (Chittiboina et al., 2014; Lonser et al., 2007; Souweidane 2014; Weber et al., 2003a; Weber et al., 2003b). Therefore, in this study, co-infusion of Gd-DTPA (commercially available Magnevist®) with PRX 321 will be carried out to depict overall drug distribution without significant safety concern. Notably, co-infusion of Gd-DTPA will enable continuous real-time monitoring of PRX 321 distribution (during at least the first 3 hours of the infusion) and permit real-time adjustment of infusate delivery by either shutting down a non-convecting catheter, repositioning the catheter or adjusting the infusate flow rate, as necessary).

No Resection Following Infusion

In previous clinical studies carried out with PRX 321 in subjects with recurrent GB, the objective was to target the bulk tumor in situ by delivering increasing intra- and peritumoral doses of PRX 321. In the first study (Phase 1) resection was only performed in response to uncontrolled edema. In the second study (Phase 2), the objective was to resect the tumor three weeks post-infusion irrespective of the edema response.

Tumor resection post-treatment neither affected disease outcome nor improved patient survival (see Investigator's Brochure Edition 10). Histological examination of resected tumors showed that by the time they were removed (3 weeks post infusion) most tumors consisted mainly of necrotic tissue.

Thus, resection post treatment did not appear to provide a better treatment outcome compared to non-resected subjects while exposing subjects to an additional risk associated with CNS surgery. Thus, the treatment strategy for this study will consist of intra- and peritumoral administration of PRX 321 without tumor resection.

Study Objectives

Primary Objective

To determine the objective response rate (ORR) per a modified RANO criteria following intra- and peritumoral infusion using CED of PRX 321 relative to pre-operative planning MRI (baseline).

Secondary Objectives

These include assessment of the safety of PRX 321 following CED, assessment of overall survival (OS), assessment of PFS (using a modified RANO criteria)

Exploratory Objectives

These include assessment of the pharmacokinetics (PK) of PRX 321 in peripheral plasma, assessment of serum anti-PRX 321 antibody titers and, if elevated determine neutralizing antibody titers, and performing additional ad hoc efficacy and safety analysis as needed based on the data acquired in this study.

Study Design

This is a single-arm, open-label, multicenter study in approximately 52 adults with primary (de novo) GB that has recurred or progressed (according to RANO criteria). The study will be conducted at up to 12 clinical sites following institutional review board approval and completed informed consent.

Eligible subjects will undergo surgery associated with study drug administration. PRX 321 infusate will be administered with the objective of achieving maximal coverage of the tumor and peritumoral margin.

Duration of infusion is expected to range between 24 to 36 hours; however, it may continue for up to 48 hours, if needed for completion. MRI scans will be performed to record distribution prior to any change of catheter position and as a final evaluation of PRX 321 infusate distribution within 4 hours (ideally within 2 hours) of completion of infusion.

Post-treatment follow-up assessment of safety will be performed 14 days after infusion. Thereafter, efficacy and safety assessments will be performed at 30, 60, 90, 120, 180, 240, and 360 days after infusion. Subjects who discontinue before the Day 360 visit will undergo all the procedures scheduled for the Day 360 visit at the time of discontinuation.

Subjects who complete the Day 360 study follow up visit without disease progression or discontinue early without disease progression will continue to be followed for disease status until progression where possible. After progression (on study or during post-study follow-up), subjects will continue to be followed for survival and post-study treatment(s) for GB and imaging for GB, where possible, until death (or termination of data collection by the Sponsor or withdrawal of consent by the subject).

Study Population

The population for this study will consist of subjects with histologically proven primary (de novo) GB that has recurred or progressed (per RANO criteria) after treatment(s) including surgery and radiotherapy with or without chemotherapy (according to local practice; Stupp protocol, Stupp et al., 2005) and following discontinuation of any previous standard or investigational lines of therapy (up to 2 prior lines of therapy).

Number of Subjects

Approximately 52 subjects with recurrent or progressive GB will be enrolled in order to achieve 36 evaluable subjects for both the primary and secondary analyses.

Eligibility Criteria

Prospective subjects must have baseline evaluation performed prior to treatment with PRX 321 and must meet all inclusion and exclusion criteria. In addition, the subject must be thoroughly informed on all aspects of the study, including the study visit schedule and required evaluations and all regulatory requirements for informed consent. Written informed consent must be obtained from the subject before conducting any study-specific procedures.

The following criteria apply to all prospective subjects considered for enrollment into the study unless otherwise specified.

Inclusion Criteria

Prospective subjects will be eligible for participation if they meet all of the following criteria:
  Subjects must be ≥18 years old and have a life expectancy ≥12 weeks
  Histologically proven, primary (de novo) GB that has recurred or progressed (first or second recurrence, including this recurrence) after treatment(s) including surgery and radiotherapy with or without chemotherapy (according to local practice; Stupp protocol, Stupp et al., 2005) and following discontinuation of any previous standard or investigational lines of therapy
  Confirmation that archived tissue is available from first diagnosis of GB for biomarker analysis
  Subjects must have evidence of tumor recurrence/progression as determined by standard RANO criteria following standard therapy:
  Includes primary GB
  Screening MRI must be performed within 14 days prior to planned infusion, and subjects receiving steroids must be on a stable, or decreasing dose for at least 5 days prior to imaging.
  More than 12 weeks must have elapsed since the completion of radiation therapy at the time of study entry
  Recurrent tumor must be supratentorial, contrast-enhancing GB no smaller than 1 cm×1 cm (largest perpendicular dimensions) and no larger than 4 cm maximum in a single direction based on MRI taken within 14 days prior to catheter placement
  Karnofsky Performance Score (KPS)≥70
  Women of child-bearing potential must have a negative beta-human chorionic gonadotropin pregnancy test documented within 14 days prior to treatment
  Women and men of child-bearing potential must agree to use adequate contraception: hormonal or barrier method of birth control; abstinence, etc. for the duration of study participation and for 6 months post drug administration. Should a woman become pregnant or suspect she is pregnant while she or her partner is participating in this study, she should inform her treating physician immediately
  Requirements for organ and marrow function as follows:
    adequate bone marrow function:
    leukocytes >2,000/μL
    absolute neutrophil count >1,000/μL
    platelets >100,000/μL
    adequate hepatic function:
    total bilirubin <1.5× institutional upper limit of normal (ULN)
    aspartate transaminase (AST)<2.5× institutional upper limit of normal (ULN)
    alanine transaminase (ALT)<2.5× institutional ULN
    adequate renal function:
    creatinine not to exceed 1.5× institutional ULN
    OR
    creatinine clearance: ≥60 mL/min/1.73 m2 for subjects with creatinine levels above institutional ULN
    lymphocytes >500/μL
  adequate coagulation function
  international normalized ratio (INR)<1.4
  partial thromboplastin time (PTT)≤institutional ULN, unless receiving therapeutic low molecular weight heparin (corrected, if necessary, to exclude potential antibody effects)
  Able to read, understand, and sign the informed consent document before undergoing any study-specific procedures or have a legal representative willing to do so; subjects must be registered prior to treatment with study drug
  Subjects must be able and willing to undergo multiple brain MRI examinations
  Subjects must be able and willing to comply with all study procedures
  Any related toxicities following discontinuation of prior GB therapies must have resolved to CTCAE Grade 1 or lower prior to inclusion in this study Exclusion Criteria Subjects will be ineligible for participation if they meet any of the following criteria:
  Prior treatment with cytotoxic chemotherapy.
  Temozolomide (standard induction and/or maintenance dosing) within the past 4 weeks prior to planned infusion.
  "Metronomic" Temozolomide (low-dose, continuous administration) within the past 7 days prior to planned infusion
  Nitrosoureas within the past 6 weeks prior to planned infusion
  Treatment with any other cytotoxic agent within the past 4 weeks prior to planned infusion
  Prior investigational treatment within the past 4 weeks or prior immunotherapy or antibody therapy within the past 4 weeks prior to planned infusion; Subjects with prior immunotherapy within 6 months of planned infusion must have confirmed evidence of tumor recurrence/progression as determined by iRANO or mRANO criteria.
  Prior treatment with bevacizumab (Avastin) or other vascular-endothelial growth factor (VEGF) inhibitors or VEGF-receptor signaling inhibitors within the past 4 weeks prior to planned infusion.
  Prior therapy that included interstitial brachytherapy or Gliadel® Wafers (carmustine implants) within the past 12 weeks prior to planned infusion.
  Prior surgery (including stereotactic radiosurgery and biopsy procedures) within the past 4 weeks prior to planned infusion.
  Ongoing Optune© therapy within 5 days of planned infusion.
  Secondary GB (i.e., GB that progressed from low-grade diffuse astrocytoma or AA).
  Known mutation in either the isocitrate dehydrogenase 1 (IDH1) or the IDH2 gene.

Tumor in the brainstem (not including fluid-attenuated inversion recovery [FLAIR] changes), an infratentorial tumor, diagnosis of gliomatosis cerebri (highly infiltrative T2 hyperintense tumor with ill-defined margins encompassing at least three lobes of the brain.

Multifocal or multicentric satellite tumors with enhancement observed outside a 4 cm×4 cm area on a single plane (maximum area covered by infusate). Multifocal lesions are defined by >1 measurable enhancing lesion (1 cm×1 cm perpendicular dimensions) separated by at least 1 cm with confluent T2 hyperintensity between the lesions. Multicentric lesions are defined by >1 measurable enhancing lesion (1 cm×1 cm perpendicular dimensions) separated by at least 1 cm with normal brain between the lesions). Measurable enhancing tumors separated by at least 1 cm with any enhancing components >4 cm apart are excluded from the current study, as these regions will not be covered by the infusion.

Tumor with a mass effect (e.g. 1-2 cm midline shift) causing clinically significant effects while on a stable corticosteroid dose Subjects with tumors for which the preponderance of tissue is not of the type in which convection would be possible (e.g. preponderance of cystic component)

Tumor with geometric features that make them difficult to adequately cover the tumor volume with infusate by using CED catheters; these include the following:

tumors that appear to wrap around ventricular structures (such as an "elbow" or "L-shape") where convection is likely to be compromised tumors in which post-surgical enhancement in T1 images in the margins around a resection cavity may be confused with recurring tumor; subjects in whom this enhancement is below 1 cm thickness are excluded tumors determined by expert review not to be good candidates for convection (e.g. on grounds of consistency, location, geometry, relationship to surrounding structures, presence of cyst, etc.

superficial tumors where direct infiltration of tumor into the cortical surface is apparent on MRI unless the distal margin of the enhancing tumor is ≥3 cm from the cortical surface (Subjects with superficial tumors where separation of the tumor from the sub-dural space by a continuous layer of intact cortex is apparent on MRI remain eligible)

Clinical symptoms that are thought by the Investigator to be caused by uncontrolled increased intracranial pressure, hemorrhage, or edema of the brain Any condition that precludes the administration of anesthesia Known to be human immunodeficiency virus positive On-going treatment with cytotoxic therapy; no additional antineoplastic therapies (including surgical modalities) are planned until there is confirmed evidence of tumor progression (as per modified RANO criteria) after administration of PRX 321

Concurrent or a history of any significant medical illnesses that in the Investigator's opinion cannot be adequately controlled with appropriate therapy or would compromise the subject's ability to tolerate the study drug therapy and/or put the subject at additional risk or interfere with the interpretation of the results of this trial Known history of allergy to gadolinium contrast agents Presence of another type of malignancy requiring treatment within <3 years prior to the screening visit, except for adequately treated carcinoma in-situ of the cervix, prostate cancer not actively treated, and basal or squamous cell carcinoma of the skin Unwilling or unable to comply with the requirements of this protocol, including the presence of any condition (physical, mental, or social or geographical) that is likely to affect the subject's returning to the investigational site for follow-up visits including for imaging or other unspecified reasons that, in the opinion of the Investigator or Sponsor, make the subject's enrollment incompatible with study objectives Subject Withdrawal Criteria The Investigator will withdraw a subject whenever continued participation is no longer in the subject's best interests. Reasons for withdrawing a subject include, but are not limited to the following:

disease progression per the modified RANO criteria (Appendix 2); Investigators are encouraged to robustly differentiate between true and pseudo-progression on MRI and other modalities (e.g. perfusion MRI, PET scan, TRAM, biopsy)

occurrence of an AE or a concurrent illness, subject's non-compliance or significant uncertainty on the part of the Investigator that continued participation is prudent.

All subjects who begin treatment should be followed for safety and efficacy. Subjects who complete the Day 360 assessment without disease progression or discontinue early without disease progression will continue to be followed for disease status until progression where possible. After progression (on study or during post-study follow-up), subjects will continue to be followed, where possible, for survival, post-study treatment(s) for GB and imaging for GB until death (or termination of data collection by the Sponsor or withdrawal of consent by the subject). If subjects receive PRX 321 and need decompression surgery, they should not be discontinued because edema may be due to tumor necrosis (beneficial treatment change) as opposed to tumor progression.

The reason for discontinuation (e.g., withdrawal of consent, lost to follow-up, unable or unwilling to undergo imaging procedures) must be documented fully in the electronic data capture (EDC) form and in the subject's medical records. Subjects who discontinue the study for any reason should undergo the assessments scheduled for the Day 360 visit at the time of discontinuation and should be followed for progression/survival unless they withdraw consent to do so.

Study Duration

Study duration is 12 months for each subject with the day of catheter placement/start of infusion being designated as Day 0.

Post-treatment follow-up assessment of safety will be performed 14 days after infusion. Thereafter, efficacy and safety assessments will be performed at 30, 60, 90, 120, 180, 240, and 360 days after infusion. Subjects who discontinue before the Day 360 visit will undergo all the procedures scheduled for the Day 360 visit at the time of discontinuation.

Subjects who complete the Day 360 study follow up visit without disease progression or discontinue early without disease progression will continue to be followed for disease status until progression where possible. After progression (on study or during post-study follow-up), subjects will continue to be followed for survival and post-study treatment(s) for GB and imaging for GB, where possible, until death (or termination of data collection by the Sponsor or withdrawal of consent by the subject).

The study drug is PRX 321 (IL-4 [38-37]-PE38KDEL), which is a recombinant fusion toxin, of approximately 53 kDa, consisting of an engineered circularly permuted (cp) version of interleukin-4 (cpIL 4) which is genetically fused to potent payload comprised of a truncated version of the bacterial toxin, *Pseudomonas aeruginosa* exotoxin (PE) A (Kreitman et al., 1994).

Mechanism of Action

The mechanism of action of PRX 321 has been described (Rand et al., 2000; Kreitman et al., 1994, Puri et al., 2009) and is depicted in FIG. 1. PRX 321 binds to IL-4R overexpressed on the surface of tumor cells and the entire complex is endocytosed. Following cleavage and activation by furin-like proteases found in high concentrations in the endosome of cancer cells, the catalytic domain of the truncated PE is released into the cytosol where it induces cell death via ADP-ribosylation of the Elongation Factor-2 and induction of apoptosis through caspase activation (Shapira and Benhar, 2010).

PRX 321 is produced by a fed batch fermentation process using recombinant *Escherichia coli*. It is expressed intracellularly in the form of inclusion bodies. Following cell lysis and solubilization of the inclusion bodies, crude protein is purified using multiple chromatographic purification steps.

PRX 321 is supplied as a sterile frozen solution at a concentration of 500 µg/mL in 0.5 mL phosphate buffered saline (PBS, 10 mM sodium phosphate, 500 mM sodium chloride, pH 7.4±0.1), filled into a sterile, single-use, 2 mL Type 1 United States Pharmacopoeia/European Pharmacopoeia (USP/EP) depyrogenated clear glass vial sealed with 13 mm Teflon-faced stoppers and labeled according to country-specific regulatory requirements.

Storage and Handling

Vials will be stored at −70° C. (±10° C.); PRX 321 is known to be stable for at least 3 years.

Composition of Infusate for CED

PRX 321 drug product will be diluted in Elliotts B® Solution to produce an infusate with a final concentration of 3 µg/mL, with 0.02% HSA and Gd DTPA (commercially available Magnevist®; 469.1 mg/mL; diluted 1:70). Details on the preparation of PRX 321 infusate are provided in the Pharmacy Manual.

NOTE: Concentration of Gd-DTPA may be adjusted to optimize visualization of infusate distribution and minimize artifacts.

Side Effects

Complete and updated AE information is available in the Investigator's Brochure (Edition 10).

Treatment Plan

Dose

PRX 321 will be administered at a fixed concentration of 3 µg/mL. The study is designed to utilize a fixed volume of infusion (Vi) so as to achieve maximal coverage of the tumor and peritumoral margin and also maintain identical local intra- and peritumoral concentration of PRX 321 in all subjects. Use of a surrogate tracer (Gd-DTPA) during infusion of PRX 321 will aim to monitor the pattern of coverage of the tumor and peritumoral margin and estimate the volume of distribution (Vd). Assuming a Vd/Vi ratio of 2.0 and a maximum tumor diameter of 4 cm in any direction, a 60 mL volume of infusion (180 µg total dose) is expected to cover the largest permitted tumor (4 cm in any direction at screening) and peritumoral margin.

Dose Administration

Total volume of infusion of 60 mL (3 µg/mL×60 mL=total dose of 180 µg PRX 321), will be administered via up to 4 catheters surgically placed according to catheter placement guidelines.

The infusate will consist of PRX 321 at 3 µg/mL with 0.02% HSA and Gd-DTPA (commercially available Magnevist®; 469.1 mg/mL; diluted 1:70) in Elliotts B® Solution.

Customary antibiotic prophylaxis for such a procedure is required and shall be administered in accordance with institutional policy; an example antibiotic protocol is outlined in Table 10.

Example dexamethasone protocol is outlined in Table 11. Routine steroid prophylaxis or treatment is not required and should be guided by clinical symptomatology. Example mannitol protocol is outlined in Table 12, if required.

TABLE 10

Example Antibiotic and H-2 Antagonist Therapy*

| Drug | Dose | Route | Duration |
| --- | --- | --- | --- |
| Ceftriaxone | 1 to 2 g/day | IV | Beginning the day of |
| Cefazolin | 3 g/day | IV | catheter implantation and |
| Vancomycin | 1 g/day | IV | continuing until the completion of the PRX 321 infusion |
| Cimetidine | 300 mg/QID | Oral | Beginning the day that |
| Ranitidine | 150 mg/BID | Oral | dexamethasone is started |
| Famotidine | 20 mg/BID | Oral | until it is stopped |

*To be administered in accordance with institutional policy;
Abbreviation:
BID = twice daily;
IV = intravenous;
QID = 4 times daily

TABLE 11

Example Dexamethasone Protocol*

| Time point | Dexamethasone Dose |
| --- | --- |
| Day of catheter placement and postoperative Days 0 and 1: | 6 mg every 6 hours |
| Postoperative Days 2 and 3: | 4 mg every 6 hours |
| Postoperative Days 4 and 5: | 3 mg every 6 hours |
| Postoperative Days 6 and 7: | 2 mg every 6 hours |
| Postoperative Days 8 and 9: | 1 mg every 6 hours |
| Thereafter | taper to off in 8 to 28 days based on neurological exam |

*As an example only. To be administered in accordance with institutional policy. If a lower dose regime or more rapid taper is considered effective, these should be used preferentially.

TABLE 12

Example Mannitol Protocol*

| Time point | Mannitol Dose |
| --- | --- |
| At any time during the duration of the infusion if subject develops symptoms of increased intracranial pressure Day 0, 1, or 2 depending on duration of planned infusion | 25 g every 6 hours for 24 hours; or per institutional practice usually 0.25 to 2 g/kg IV over at least 30 min administered not more frequently than every 6 to 8 hours. +dexamethasone up to maximum of 16 mg daily |

*To be administered in accordance with institutional policy

Instructions for PRX 321 Infusate Administration

Preliminary pre-treatment catheter trajectory planning using CT scan and screening MRI (registered with iPlan®

Flow Infusion planning software) will be performed within 14 days of catheter placement following approval of subject for enrollment. Catheter trajectories will be planned using the following guidelines:
- a) Aim to place 4 catheters in all cases with as many as possible, but ordinarily a minimum of 2 catheters, located in enhancing tumor tissue, except in the smallest tumors where this is not feasible.
- b) Any remaining catheter(s) should be placed outside of enhancing tumor, within the T2 flair signal area and ≤2 cm from the enhancing rim of the tumor.
- c) The catheter tip must not be located within necrotic, cystic, or CSF regions including the ventricular system, sulci, and any resection cavity.
- d) The catheter tip should generally be placed ≥0.5 cm from the ventricular system or sulci in areas where ependyma/pia mater remains intact and ≥1 cm away from such areas and previous resection cavities where there is no intact margin.
- e) Catheter(s) should not cross sulci.
- f) Suitability of the skull surface (bone condition and prosthetic material from previous surgery) should be considered in planning the locations for the catheter anchor screw points (per reference CT scan).

Timing of planning images to support catheter trajectory planning is described in Planning MRI images will be registered with iPlan® Flow Infusion planning software to support finalization of catheter trajectory plan.

The approved neuro-navigation system VarioGuide™ by Brainlab will be utilized for surgical placement of catheters on Day 0. Workflow for administration of PRX 321 employing VarioGuide™ is described in Table 13. This table also outlines the required materials for catheter placement and infusion.

It is recognized that experience is likely to result in minor refinement of these procedures. Such refinements will not require amendment of the protocol as long as they do not increase the risk for the subject.

TABLE 13

Procedure using VarioGuide ™ Neuro-navigation for Catheter Placement, Followed by Infusion A. List of Required Materials*

Brainlab iPlan ® Flow Infusion planning software
Brainlab Flexible Catheter kits
Brainlab VarioGuide ™ frameless image-guided stereotactic system
VarioGuide Drill Kit (one drill kit is needed for all catheters placed)
B Braun (USA) micro bore extension tubing lines
B Braun (USA) Perifix ® catheter connectors
Rubber tubing
Medfusion 3500 syringe pumps with corresponding pole clamps
1 syringe pump per catheter placement + 1 back up pump
MRI safe IV stand for stationing the Medfusion 3500 Syringe pumps
Medfusion 3500 compatible Luer-lock syringe(s)
PRX 321 infusate
See Pharmacy Manual for instructions on preparation and dispensing of the infusate
Hospital pharmacy will be informed of the planned treatment date in a timely manner for them to prepare and dispense the infusate required on Day 0.
PRX 321 Study Reference Guide provides supplemental information as indicated throughout this protocol to facilitate the execution of the study
PRX 321 Image Acquisition Guide provides information on sequences required for image acquisition and image data transfer
Study specific source document worksheets for capture of specific catheter placement and infusion parameter data
* Specifications for the required materials are provided as described herein.

B. Pre-operative Planning

1) Following approval of subject for enrollment, pre-treatment catheter trajectory planning will be performed in conjunction with catheter placement guidelines
   a. Preliminary trajectory planning can be performed using screening MRI and CT scans
2) Within 24 hours of catheter placement pre-operative planning MRI with in situ scalp fiducials will be performed
   a. Timing of planning images to support catheter trajectory planning is described in herein; Planning MRI images will be registered with iPlan ® Flow Infusion planning software to support finalization of catheter trajectory plan.
   b. Functions of planning MRI are also described in herein.
3) Within 24 hours of catheter placement Treatment Plan study specific source worksheet will be completed and reported to hospital pharmacy for dispensing infusate.

C. Catheter Placement

Subject will be hospitalized in accordance with the institution's standard of care before catheter placement.
See above for example of mandatory antibiotic/H-2 antagonist therapy and for optional dexamethasone and mannitol therapy for management of raised intra-cranial pressure (ICP), respectively.
1) Completion of study specific source document worksheets as required throughout procedure
2) On the day of surgery, the subject will be prepped and anaesthetized according to institution's standard procedures
   a) Subject will receive general anesthesia for the procedure and a member of the anesthesiology department must remain present for the entire procedure

TABLE 13-continued

Procedure using VarioGuide ™ Neuro-navigation
for Catheter Placement, Followed by Infusion

- b) Hospital Pharmacy will dispense PRX 321 infusate in luer lock syringes to the operating room
  NOTE: See Pharmacy Manual for instructions on preparation and dispensing of the infusate
  NOTE: Syringes are required to be in the operating room prior to catheter placement; therefore, important for hospital pharmacy to be made aware of surgery start time
3) Sequential placement of catheters according to the following process:
   a) Prior to inserting each catheter, the corresponding infusion assembly will be set up and it must be primed with the infusate using Medfusion 3500 syringe pump
   b) VarioGuide navigation is used to make a burr hole at the cranial entry site using VarioGuide Drill Kit. Brainlab Flexible Catheter(s) will be guided into the tumor using VarioGuide. The catheter has a rigid stylet design for accurate positioning. Once catheter(s) are positioned, the stylet component is removed and the flexible catheter(s) secured with bone anchor(s) to the skull at the desired depth of placement.
      NOTE: each Brainlab catheter kit and drill kit comes with instructions for use which provides details on depth control for catheter placement
      NOTE: See Study Reference Guide for instructions for preparing and priming the infusion assembly as well as pump operation D. Real-Time Infusion

***FOLLOWING CATHETER PLACEMENT SUBJECT WILL REMAIN UNDER GENERAL ANEASTHESIA FOR AT LEAST THE FIRST 3 HOURS OF THE INFUSION TO ALLOW FOR A CONTNUOUS PERIOD OF REAL-TIME MONITORING OF DRUG DISTRUTION AND ADJUSTMENT OF INFUSION PARAMETERS AS NEEDED BY THE INVESTIGATOR

4) Subject will be loaded into the MRI machine
   a) If placement of the catheter(s) occurred in an operating room that is not equipped with an intraoperative MRI (iMRI), transport of the subject to MRI suite is required; subject will be escorted under supervision of anesthesiology per each institution's guidelines.
   b) All equipment used must be MRI compatible and all members of the team who are present in the MRI suite must have documented MRI safety training
      NOTE: Medfusion syringe pumps must be secured to a non-moveable object and the magnetic fringe field should not exceed 150 gauss
5) Prior to start of infusion, MRI scan will be performed to confirm catheter placement
6) Infusion via each catheter will be initiated at the rate of 3 µL/min/catheter and gradually increased in a stepwise manner and catheter depth adjusted at the discretion of the Investigator (see 6 a-f below)
   NOTE: See Study Reference Guide for instructions on pump operation (e.g. how to set and change flow rate)
   a) Infusion flow rate can be adjusted, in increments that do not exceed 5 µL/min/catheter
   b) Total (combined) flow rate for all functioning catheters should not exceed 50 µL/min and all functioning catheters should convect at similar flow rates.
   c) Flow rate adjustments will be based on subject specific tolerance of infusion (e.g. tissue reaction, initial infusate distribution, evidence of backflow up the catheter tract and infusate leakage or escape into CSF spaces) as observed by real time assessment of infusate distribution.
   d) MRI will be performed during the first 3 hours of the infusion to monitor the distribution of the infusate in real time. Repeat MRIs will be collected continuously (at approximately 10-15 minute scanning intervals) during the first hour and then approximately every 20 to 30 minutes for the remainder of the time spent monitoring the infusion in the MRI scanner.
   e) The time of any catheter adjustments should be noted using the Study Specific source document worksheets.
   f) If evidence of backflow along the catheter is observed the infusion rate may be slowed. Flow rate may be adjusted until an optimal maintenance flow rate is established (this established maintenance flow rate should be employed for the remainder of the infusion where possible).
   g) If sub-optimal distribution from a specific catheter placement is observed (e.g. back flow or leakage into CSF) or if distribution is not observed the catheter may be advanced along the same trajectory by adjustment of the skull screw.
      The catheter skull screw system secures into the skull and a compression cap secures the catheter in place. Loosening the compression cap allows the catheter to advance without the stylet; The catheter can be advanced up to 2-3 cm to optimize tumor coverage and infusate distribution.
      NOTE: retraction of the catheter during infusion is not permitted routinely.

E. Post-surgical Infusion

7) Administration of the total 60 mL infusate volume cannot be completed intra-operatively; thus, following the real time MRI infusion monitoring period, catheters will remain in final position, and subject will be moved to the post anesthesia recovery unit (PACU) to be weaned off anesthesia.
9) Infusion will continue for the duration required to administer the remainder of the infusate volume during an inpatient admission on a hospital floor with appropriate personnel trained in post-operative neurological/neurosurgical monitoring.
   a) Should the subject develop symptoms suggestive of intolerance of the maintenance flow rate, the rate of infusion of all convecting catheters may be reduced by 50% or the infusion stopped and restarted at the discretion of the Investigator.

TABLE 13-continued

Procedure using VarioGuide ™ Neuro-navigation
for Catheter Placement, Followed by Infusion b) Total infusion duration is expected to range between 24 to 36 hours depending on flow rate and number of convecting catheters; however, it may continue for up to 48 hours, if needed for completion.
10) End of infusion assessments:
  a) First PK sampling time point as soon as possible but not more than 1 hour after infusion end time (see herein for details on PK sampling time points post infusion)
  b) Within 2 hours after infusion end time 12 lead ECG (triplicate assessment) performed
  c) Within 4 hours (ideally within 2 hours) after infusion end time MRI performed for a final evaluation of drug distribution and catheter positions
11) See herein for details on additional post infusion procedures/assessments.
12) Completion of study specific source document worksheets as required throughout hospitalization period.

Image Acquisition—Schedule and Requirements

MRI will be used in this study to evaluate eligibility, plan and confirm catheter placement, assess infusate distribution and follow the subject for response, progression or pseudo-progression.

An Imaging Core Lab, Intrinsic Imaging LLC (San Antonio, TX) will provide independent central image review, for purposes of this protocol. Interpretation of medical images will be performed according to a study specific Imaging Charter.

Table 14 summarizes images which must be acquired for this study. All scans must be obtained using pre-defined imaging protocols to ensure reproducibility at different time points and in a manner consistent with Consensus Guidelines (Ellingson et al., 2015). All image data will be sent to the Imaging Core Lab through electronic transfer. Training will be provided to the relevant site staff (radiologists, radiology technicians) to ensure that the required MRI scanning parameters are used for the indicated time points.

A study-specific Image Acquisition Guide details the imaging protocol and minimum requirements for the successful acquisition and transfer of image data. A general procedure for image acquisition/transfer is outlined in Table 14.

TABLE 14

Imaging Schedule*

| SCAN | PURPOSE |
|---|---|
| Screening MRI Within 14 days prior to catheter placement | Assess radiologic eligibility criteria |
| | independent central assessment of objective tumor characteristics |
| | Preliminary catheter trajectory planning using iPlan ® Flow Infusion planning software |
| | Electronic image data transfer immediately following acquisition (<4 hours) |
| Screening CT Scan [a] Within 14 days prior to catheter placement | Assessed during screening to ensure no prior skull defects or hardware that would preclude catheter placement |
| | Catheter trajectory planning to ensure no prior skull defects or hardware in the way of planned entry points for any of the planned catheter trajectories |
| | Electronic image data transfer immediately following acquisition (<4 hours) |
| Pre-Operative Planning MRI [b] Within 24 hours prior to catheter placement [c] | Baseline scan for tumor response assessment, including tumor dimensions, using same MRI scanner that will be used for all follow-up MRIs |
| | Baseline image acquisition for TRAMs assessment (for sites using TRAM) |
| | Finalization of catheter trajectory planning using iPlan ® Flow Infusion planning software |
| | Pre-operative scan with in situ scalp fiducials to assure optimal catheter placement (within 24 hours of catheter placement) |
| | Electronic image data transfer immediately following acquisition (< 4 hours) |
| Catheter Placement Confirmation [b] Day 0 - Following surgical placement of catheters | Confirmation of catheters placed by MRI prior to starting infusion |
| | Electronic image data transfer following acquisition (<2 days) |
| REAL-TIME INFUSION MONITORING [b] Day 0 - At least first 3 hours of Infusion | MRI will be performed during the first 3 hours of the infusion to monitor the distribution of the infusate in real time. |
| | Repeat MRIs will be collected continuously (at approximately 10-15 minute scanning intervals) during the first hour and then approximately every 20 to 30 minutes for the remainder of the time spent monitoring the infusion in the MRI scanner. |
| | Electronic image data transfer following acquisition (<2 days) |

TABLE 14-continued

Imaging Schedule*

| SCAN | PURPOSE |
| --- | --- |
| End of Infusion MRI Within 4 hours (ideally within 2 hours) following infusion end time | MRI will be performed after completion of the infusion to allow for a final evaluation of drug distribution<br>Confirmation of final catheter positions<br>Electronic image data transfer following acquisition (<2 days) |
| Follow Up MRI 30, 60, 90, 120,180, 240, and 360 days post infusion | Tumor response assessment, including tumor dimensions [d]<br>Tissue response assessment (TRAMs), Day 30, 60, 90, 120 and 180 and additional time points (if clinically indicated) for sites using TRAMs<br>Electronic image data transfer immediately following acquisition (<24 hours) |
| Unscheduled Follow up MRI | CR or PR or PD confirmation by repeat assessment 4 weeks after it is observed [d]<br>Required if response or progression observed at Day 120, 180, 240 or 360 relative to baseline pre-operative planning MRI<br>Electronic image data transfer immediately following acquisition (<24 hours) |

*A study-specific Image Acquisition Guide details the imaging protocols and minimum requirements for the successful acquisition and electronic transfer of images to the Imaging Core Lab;
[a] CT scan acquisition only required when no CT scan is available within 3 months of planned infusion
[b] Remote and/or on-site case support will be provided to the Investigator by the Sponsor for catheter trajectory planning and real-time infusion monitoring
[c] Full quality MRI scanning is required for baseline response assessments, central tumor measurement and to finalize catheter trajectory planning, in case of tumor growth since screening. In addition, MRI imaging is needed to register the placement of scalp fiducials which may require only a limited scanning protocol and may be conducted using an intraoperative scanner. Final catheter trajectory plans should be completed sufficiently in advance of surgery to enable timely central peer review;
Timing of planning MRI - Pre-operative planning MRI can be performed in one or two MRI exams as required, based on local capabilities and operational scheduling. Where it is possible to fulfill all functions of the planning MRI in a single examination, in terms of the required quality and timing for the availability of reviewers, a single planning MRI will be completed within 24 hours prior to catheter placement, with scalp fiducials in situ. Where it is not possible to fulfill all functions of the planning MRI within a single examination, the planning MRI should be conducted within 3 working days of planned catheter placement and a further check image completed within 24 hours prior to catheter placement, with scalp fiducials in situ.
[d] Modified RANO criteria (see belwow) and site tumor measurement guideline (see Imaging Acquisition Guide).

Screening MRIs will be assessed for determination of disease status and subject eligibility. These images will be evaluated at the site and transmitted to the Imaging Core Lab to provide independent central assessment of objective tumor characteristics. All image reviews concerning study endpoints will be conducted in a blinded manner by an independent reviewer, without knowledge of the clinical condition or identity of the subject or the local site assessment. Additional image reviews pertaining to evaluation of suitability of subjects for convection may be performed by CED experts.

The following criteria will be utilized for independent evaluation of objective tumor characteristics for consideration in determination of eligibility as follows:

Tumor diameter of ≥1 cm x≥1 cm (perpendicular dimensions), minimum, and a maximum size in any single dimension of 4 cm Tumor location not infratentorial or involving brainstem Diagnosis of gliomatosis cerebri (highly infiltrative T2 hyperintense tumor with ill-defined margins encompassing at least three lobes of the brain)

Multifocal lesions and multicentric lesions are discouraged, but allowable so long as all boundaries of any multifocal, measurable enhancing lesions are within a 4 cm×4 cm area (maximum area covered by infusate). Multifocal lesions are defined by >1 measurable enhancing lesion (1 cm×1 cm perpendicular dimensions) separated by at least 1 cm with confluent T2 hyperintensity between the lesions. Multicentric lesions are defined by >1 measurable enhancing lesion (1 cm×1 cm perpendicular dimensions) separated by at least 1 cm with normal brain between the lesions.

Independent central review of screening MRIs will be expedited. No subject will be enrolled in the study without this central imaging assessment being performed and reviewed by the Medical Monitor with further advice based on imaging reviews from CED experts, as required, especially in regard to tumors considered not to be good candidates for CED (see above). All subjects will be approved for enrollment by the Medical Monitor following a comprehensive review of the screening eligibility package comprising the independent central imaging assessment as well as documentation substantiating screening assessments.

Follow up MRIs will be subject to local site review for determination of response/progression including tumor dimensions per a modified RANO criteria (see Appendix 2). Tumor measurements will be performed following a specific guideline in order to ensure consistency in all local tumor response assessments (see Image Acquisition Guide). Importantly, the modified RANO criteria used in the current study allows for patients to stay on study past initial radiographic progression to exclude possible pseudo-progression. Specifically, the modified RANO criteria suggests an initial progressive disease (PD) event be designated "preliminary PD" and followed up with confirmation of true PD, and subsequent withdrawal of the patient from treatment, only after repeat MRI and supportive assessments (e.g. perfusion MRI) at least 4 weeks following the preliminary PD event. While adherence to this modified RANO criteria is recommended, as there is a high likelihood of early progressive enhancement following treatment, patient management is at the discretion of the Investigator.

Follow up MRIs will also be subject to independent central image review for determination of response/progression including tumor dimensions at each follow up time point.

Study Procedures and Observations
Efficacy Evaluation—Tumor Response Assessment

Independent assessment of tumor response, relative to pre-operative planning MRI (baseline), will be performed by the Imaging Core Lab, and be based on the evaluation of MRI scans performed at 30, 60, 90, 120, 180 240, and 360 days post-infusion with respect to baseline examinations. Response and progression will be determined using the modified RANO criteria (Ellingson et al., 2017 Appendix 2), which allows for patients to stay on study past initial radiographic progression in order to exclude pseudo-progression. Subject should only be withdrawn after repeat MRI and supportive assessments (e.g. perfusion MRI) at least 4 weeks following a preliminary PD event.

PFS, ORR, duration of response (DOR), and duration of clinical benefit (DOCB) will be assessed based on the independent assessment.

Survival

After progression (on study or during follow-up), subjects will continue to be followed for survival and post-study treatment(s) for GB and imaging for GB, where possible, until death (or termination of data collection by the Sponsor or withdrawal of consent by the subject).

Safety Evaluation

Safety will be evaluated through AE monitoring, clinical evaluations (i.e., vital signs, physical examinations, electrocardiogram [ECG]), laboratory tests (i.e., hematology, serum chemistries, and urinalysis), antibody (serum anti-PRX 321 antibody and neutralizing antibody where applicable) assessments, and plasma drug levels on PK samples from the signing of informed consent until the last study visit (360 days post-infusion or termination).

Required Clinical Laboratory Tests for Each Panel Will be as Follows:

- Hematology: hemoglobin, hematocrit, platelet count, white blood cell (WBC) count, and WBC differential;
- Coagulation: prothrombin time (PT)/PTT/INR (PTT, corrected, if necessary);
- Serum chemistry: AST, ALT, lactate dehydrogenase (LDH), total bilirubin, indirect bilirubin, alkaline phosphatase, total protein, albumin, sodium, potassium, chloride, carbon dioxide, calcium, phosphorus, blood urea nitrogen (BUN), creatinine, uric acid, and glucose;
- Urinalysis: pH, specific gravity, protein, glucose, ketones, blood, leukocyte esterase, and nitrite. Microscopy required only to follow-up clinically significant abnormal findings; and
- Pregnancy: Serum pregnancy tests will be performed at screening and at 30 and 180 days post infusion for all women of childbearing potential.

The Investigator or a designated associate will review all clinical laboratory results, and clinically significant findings will be reported as AEs and followed or treated according to institutional guidelines or the treating physician's medical judgment.

Safety Considerations

Physical examinations will be performed at screening, within 24 hours prior to catheter placement and following infusion on Days 1 or 2 (according to infusion duration), 14, 30, 60, 90, 120, 180, 240, and 360 (or early termination). The screening and Day 360 (or early termination) examinations will be complete physical examinations; other examinations should be focused, at the discretion of the Investigator, to assess changes from the previous examination. Clinically significant changes in physical examination findings during or after treatment, including transient neurological symptoms, will be reported as AEs.

Other safety assessments will include vital signs. The Investigator or a designated associate will review all vital sign results, and clinically significant findings will be reported as AEs and followed or treated according to institutional guidelines or the treating physician's medical judgment. Triplicate twelve-lead ECGs are taken during screening and within 2 hours following completion of infusion, and clinically significant abnormal findings must be followed by the Investigator.

Pharmacokinetic and Immune Parameter Evaluations

Systemic exposure to PRX 321 is not expected following intra- and peritumoral infusion, and circulating PRX 321 has not been detected in previous clinical studies. To continue to evaluate the potential of systemic exposure, blood samples will be collected for analysis at the times indicated in Table 15.

Blood samples will also be collected for testing for the presence of antibodies against PRX 321 (Table 15). If serum anti-PRX 321 antibodies are present, further immunogenicity assessments will be carried out for determination of antibody neutralization potential and other immune parameters may also be assessed.

All collected blood samples will be processed according to a laboratory manual and samples will be stored at −70° C. until instructions are provided to the site to ship the samples to the central testing laboratory (MicroConstants Inc., San Diego, CA).

Tumor Tissue Analysis

During screening, confirmation that archived tumor tissue from initial GB diagnosis is available for the patient is required.

Tissue sample archived from initial GB diagnosis and/or tissue sample archived following recurrence will be utilized for retrospective analysis of IL-4R expression using immunohistochemistry (IHC). The tissue sample may also be subject to retrospective analysis of other biomarkers, including but not be limited to methylation status of the MGMT gene, as described herein.

Biomarker analysis will be conducted to determine if there is a correlation between IL-4R expression and/or MGMT status and treatment response to PRX 321.

Analyses on other tumor tissue samples obtained during other surgical procedures or local evaluations of disease status (e.g. samples from repeat resections or biopsies taken to establish tissue response status) should be recorded and may be used in sensitivity, sub-group and other exploratory analyses.

IL-4R Expression

Archived tumor tissue specimens from subjects entering the study will be processed by IHC at a CLIA certified laboratory (QualTek Molecular Laboratories, Goleta, CA) for analysis of IL-4R expression to determine if there is a correlation between IL-4R expression and tumor response following PRX 321 treatment.

Tissue sections will be graded for IL-4R expression by examining staining intensity in a blinded fashion for each specimen using a semi-quantitative scale of 0, 1+, 2+, and 3+ (as well as H-Score). Further quantitative assessment of IL-4R staining may include standardized image analysis. Efficacy endpoints (such as PFS, ORR, OS, DOR, DOCB) will be evaluated versus intensity of IL-4R expression.

O6-Methylguanine-Methyltransferase Analysis

MGMT-expressing cancer cells (harboring unmethylated MGMT promoters and therefore resistant to temozolomide) are sensitive to PRX 321.

Thus, tumor tissue specimens from subjects will be processed at a CLIA certified laboratory for MGMT DNA methylation analysis using a quantitative methylation-specific PCR technique. Primary and secondary endpoints will be analyzed against the MGMT methylation status.

Evaluation of Progression Versus Pseudo-Progression

For malignant gliomas, conventional MRI is currently used to determine radiologic response. While this method has been used to determine overall tumor response, image interpretation is at a few occasions confounded by either pseudo-response or pseudo-progression due to the fact that conventional MRI is unable to differentiate tumor/non-tumor enhancing tissues (Verma et al., 2013). Therefore, determination of true response may take several months post-treatment (Floeth et al., 2002). To address this issue, advanced imaging techniques such delayed contrast extravasation MRI for calculating high resolution treatment response assessment maps (TRAMs) has been evaluated for its ability to determine local treatment effects, distinguish between true response and pseudo-response or pseudo-progression and confirm response in GB patients at earlier time points (Zach et al., 2012; Zach et al., 2015; Daniels et al., 2016). Likewise, perfusion MRI, PET scan and biopsy may be used to aid differentiation between true and pseudo-response or progression.

Study Visit Schedule

All clinical study evaluations and procedures will be performed according to the schedule of assessments (Table 15) and the instructions listed in the sections following.

All on-study visit procedures are allowed a window of time unless otherwise noted. *Treatment or visit delays for weekends, public holidays or weather conditions do not constitute a protocol violation.

TABLE 15

Schedule of Evaluations and Procedures*

| Evaluation | Screen | Hospitalization | | | | 14 Day | 30, 60, 90 120 180, 240, and 360 Day | Long Term F/up |
|---|---|---|---|---|---|---|---|---|
| | | Before Catheter Placement | Catheter Placement | Infusion | End of Infusion | | | |
| Day | −14 to 0 | −24 hrs to 0 | 0 | 0-2 | 1-2 $^a$ | 14 $^a$ | a, b, c | p |
| Informed Consent $^d$ | X | | | | | | | |
| Hospital Registration | | X | | | | | | |
| Medical/Oncological History | X | X | | | X | | | |
| Operative & Pathology Reports for Index Tumor (resection/biopsy) $^e$ | | X | | | | | | |
| Confirmation of archived tissue being available for biomarker analysis $^f$ | X | | | | | | | |
| MRI | $X^{g1}$ | $X^{g2}$ | $X^{g3}$ | | $X^{g4}$ | | $X^{g5}$ | |
| CT | $X^{g6}$ | | | | | | | |
| Physical Exam, KPS | X | X | | | $X^q$ | X | X | |
| Vital Signs (pulse, respiratory rate, weight and blood pressure) | X | X | $X^r$ | $X^r$ | $X^s$ | X | X | |
| Neurological Exam | X | X | | | X | X | X | |
| Standard 12-lead Electrocardiogram (triplicate assessment) | X | | | | $X^t$ | | | |
| Serum Pregnancy Test $^{h1}$ | X | | | | | | X | |
| Hematology/Serum Chemistry $^{h2}$ | X | | | | $X^u$ | X | X | |
| Coagulation $^{h3}$ | X | | | | $X^u$ | X | X | |
| Urinalysis $^{h4}$ | X | | | | | | | |
| Pharmacokinetics $^i$ | X | | | X | | X | | |
| Immunogenicity $^j$ | X | | | | | X | X | |
| Baseline Conditions $^k$ | X | X | | | | | | |
| Pharmacy Preparation of Infusate $^l$ | | | X | X | | | | |
| Catheter placement $^l$ | | | X | | | | | |
| Infusion: PRX 321/Gadolinium $^l$ | | | | X | | | | |

TABLE 15-continued

Schedule of Evaluations and Procedures*

| Evaluation | Screen | Hospitalization | | | | 14 Day | 30, 60, 90 120 180, 240, and 360 Day | Long Term F/up |
| --- | --- | --- | --- | --- | --- | --- | --- | --- |
| | | Before Catheter Placement | Catheter Placement | Infusion | End of Infusion | | | |
| Catheters Removal $^m$ | | | | | X | | | |
| Concomitant Meds/Corticosteroids $^n$ | X | X | X | X | X | X | X | |
| Adverse Events $^o$ | | | X | X | X | X | X | |
| Telephone Contact $^p$ | | | | | | | | X |

*Treatment or visit delays for weekends, public holidays or weather conditions do not constitute a protocol violation $^a$ Safety assessed after initiation of infusion (during and following infusion throughout entire hospitalization period) and safety follow-up to be performed on Days 14 and 30 (±3 days), and 60, 90, 120, 180, 240, and 360 (±7 days)

$^b$ Scheduled follow-up to be performed with MRI up to 12 months after infusion on Day 30 (±3 days) and Days 60, 90 120, 180, 240, and 360 (±7 days) after initiation of infusion $^c$ Subjects who discontinue before the Day 360 visit will undergo all the procedures scheduled for the Day 360 visit if early termination is between follow-up visit time points with the specific provision that MRI will not be required if last MRI performed was within 2 weeks prior to the early termination date. When early termination is in line with a study follow up visit time point (i.e. Day 30, 60, 90, 120, 180 or 240) time that visit will be considered the early termination time point and no other assessments apart from the respective visit date assessments will be required.

$^d$ ICF can be signed in advanced of the 14 day screening period $^e$ Operative report to be accessioned $^f$ Archived tissue from the resection of the initial GB diagnosis required for biomarker analysis including IL-4R IHC, MGMT DNA methylation, and other translational biomarkers g All MRIs acquired throughout entire study schedule will follow will be performed according to imaging protocols outlined in the study specific Image Acquisition Guide $^{g1}$ Screening MRI to be subject to independent assessment to verify objective radiologic tumor characteristics [e.g. tumor size; subjects must have tumor diameter of ≥1 cm × ≥1 cm (minimum) to 4 cm in any direction, etc.]; additional image reviews of screening MRI pertaining to evaluation of suitability of subjects for convection may be performed by CED experts; if subject approved for enrollment, screening MRI can also be used for preliminary catheter trajectory planning using iPlan ® Flow $^{g2}$ Pre-operative planning MRI can be performed in one or two MRI exams as required, based on local capabilities and operational scheduling. Where it is possible to fulfill all functions of the planning MRI in a single examination, in terms of the required quality and timing for the availability of reviewers, a single planning MRI will be completed within 24 hours prior to catheter placement, with scalp fiducials in situ. Where it is not possible to fulfill all functions of the planning MRI within a single examination, the planning MRI should be conducted within 3 working days of planned catheter placement and a further check image completed within 24 hours prior to catheter placement, with scalp fiducials in situ.

$^{g3}$ On Day 0 MRI performed following catheter placement prior to the start of infusion as well as during infusion for real-time MRI infusion monitoring (for a minimum time of 3 hours while subject is maintained under anesthesia) (see infusion procedure, described herein)

$^{g4}$ On Day 1 or Day 2 (depending on duration of infusion) MRI performed within 4 hours (ideally within 2 hours) after completion of infusion relative to infusion end date/time $^{g5}$ MRI performed as part of the scheduled follow-up visits on Days 30, 60, 90, 120, 180, 240, and 360/early termination $^{g6}$ CT scan acquisition only required when no CT scan is available within 3 months of planned infusion $^{h1}$ Females of child bearing potential only at Screening, Days 30 and Day 180

$^{h2}$ Hematology: hemoglobin, hematocrit, platelet count, white blood cell (WBC) count, and WBC differential;
Serum chemistry: AST, ALT, lactate dehydrogenase (LDH), total bilirubin, indirect bilirubin, alkaline phosphatase, total protein, albumin, sodium, potassium, chloride, carbon dioxide, calcium, phosphorus, blood urea nitrogen (BUN), creatinine, uric acid, and glucose $^{h3}$ Coagulation: prothrombin time (PT)/PTT/INR (PTT, corrected, if necessary)

$^{h4}$ Urinalysis: pH, specific gravity, protein, glucose, ketones, blood, leukocyte esterase, and nitrite. Microscopy required only to follow-up clinically significant abnormal findings $^i$ PK assessed at Screening (baseline), as soon as possible but not more than 1 hour following infusion end time, approximately 3 hours following completion of infusion and then (after the ~3 hour sample collection) every 6 hours ± 2 hours until 24 hours or until subject is discharged from the hospital (whichever occurs first) and at Day 14

$^j$ Immunogenicity assessed at Screening (baseline) and at Days 14, 30, 120, 240, and 360/early termination $^k$ Baseline/conditions symptoms will be collected from Screening until Day 0 before subject is anesthetized for catheter placement surgery; any baseline condition or symptom noted prior to catheter placement will be recorded in the Medical History $^l$ see herein for infusate preparation and dispensing instructions $^m$ Following completion of infusion (only after the end of infusion MRI and at any time poor to subject's discharge from the hospital), the catheters can be removed and the incisions closed in accordance with institutional practice. Removal of catheters must be performed by a delegated neurosurgeon.

$^n$ All concomitant medications and corticosteroid medications will be collected on the Electronic Data capture (EDC) system from the date of informed consent through 30-day safety period. Thereafter, concomitant medications associated with treatment-related SAEs and detailed anti-tumor therapy will be collected.

$^o$ All AEs will be collected from catheter placement through the end of study visit and all AEs and SAEs will be followed until resolution, stabilization, data cut-off, or death $^p$ Subjects who complete the Day 360 study follow up visit without disease progression or discontinue early without disease progression will continue to be followed for disease status until progression where possible. After progression (on study or during post-study follow-up), subjects will continue to be followed for survival and post-study treatment(s) for GB and imaging for GB, where possible, until death (or termination of data collection by the Sponsor or withdrawal of consent by the subject).

$^q$ Physical exam and KPS assessments will be performed after completion of infusion when the subject is ambulatory prior to hospital discharge $^r$ Vital signs monitoring (without weight parameter) will be performed according to institutional best practice throughout entire surgical workflow for catheter placement and infusion; study specific vital signs check points during the surgical workflow are prior to initiation of anesthesia, following placement of all catheters but prior to patient being loaded into MRI machine for the real-time infusion monitoring segment and approximately 1 hour post initiation of infusion; NOTE: Site will record any abnormal vitals observed at any time during surgical vital signs monitoring as unscheduled findings.

$^s$ Vital signs taken after completion of infusion when the subject is ambulatory prior to hospital discharge $^t$ ECG (triplicate assessment) will be performed at Screening and immediately following completion of infusion (within 2 hours of infusion end time); triplicate assessment in 3 immediate traces $^u$ Blood samples for hematology, serum chemistry, and coagulation shall be taken in parallel with either the PK blood collection that is performed within 1 hour following completion of infusion or the PK blood collection that is performed ~3 hours following completion of infusion Pretreatment Period Screening Assessments (within 14 Days of Infusion)

Before a subject can be considered for entry into the study, the Investigator must receive the subject's clinical history, general laboratory results, specific radiological evaluations and diagnoses, and a chronology of all previous therapies for the treatment of GB, including outcomes, from the referring physician. Subjects should have results from a previous histological diagnosis of initial primary (de novo) GB and a pre-study MRI scan providing radiological evidence of recurrence or progression.

A written and signed ICF and HIPAA authorization must be obtained before any study-specific assessments are initiated. The ICF can be signed in advanced of the 14-day screening period.

The following assessments must be carried out within 14 days before catheter placement:

Screening MRI to assess radiologic eligibility criteria.
  Electronic image data transfer immediately following acquisition (<4 hours).
CT scan assessed during screening to ensure no prior skull defects or hardware that would preclude catheter placement (CT scan acquisition only required when no CT scan is available within 3 months of planned infusion).
  Electronic image data transfer (should be concomitant with transfer of screening MRI).
Verification that archived tumor tissue (from initial GB diagnosis) is available for retrospective biomarker analysis.
Complete medical and oncologic history, including history of prior surgical procedures and prior treatments, prior conditions, signs and symptoms and any residual/ongoing toxicity relating to prior treatment(s).
Complete physical and neurological examinations, including height, weight, mental status, cranial nerves, motor and sensory examinations, and KPS.
Baseline signs and symptoms.
Vital signs (pulse, respiratory rate, weight and blood pressure).
Standard 12-lead ECG (triplicate assessment).
Hematology, serum chemistry, and coagulation.
  If the coagulation values are clinically significant, they must be repeated until within normal limits, unless subject is receiving therapeutic low molecular weight heparin.
NOTE: Any test results outside of the reference ranges may be repeated at the discretion of the Investigator.
Collection of blood sample for Immunogenicity analysis (baseline).
Collection of blood sample for PK analysis (baseline).

Concomitant medications and treatments will be recorded from 14 days before infusion (Day 0) until the Day 360 (or early termination) visit, and AEs will be recorded from the time of signing the informed consent document until the Day 360 (or early termination) visit.

In addition, a serum pregnancy test must be performed within 14 days before infusion (Day 0) for all female subjects of childbearing potential.

While the above assessments are being carried out, screening MRI will be subject to review by CED experts pertaining to evaluation of suitability of tumor for convection. The screening MRI will also be sent to the Imaging Core Lab for independent central assessment of objective radiologic tumor characteristics.

Subjects will be approved for enrollment by the Medical Monitor following comprehensive review all screening results.

Following approval of subject for enrollment, Investigator/site will be notified and preliminary pre-treatment catheter trajectory planning using CT scan and screening MRI (registered with iPlan® Flow Infusion planning software) can ensue.

NOTE: use of iPlan® Flow software will be employed for catheter trajectory planning.

Treatment Period
Pre-Operative Study Procedures within 24 Hours of Catheter Placement Within 24 hours prior to catheter placement, subjects will undergo the following procedures and assessments:
Pre-Operative Planning MRI Pre-operative planning MRI can be performed in one or two MRI exams as required, based on local capabilities and operational scheduling. Where it is possible to fulfill all functions of the planning MRI in a single examination, in terms of the required quality and timing for the availability of reviewers, a single planning MRI will be completed within 24 hours prior to catheter placement, with scalp fiducials in situ. Where it is not possible to fulfill all functions of the planning MRI within a single examination, the planning MRI should be conducted within 3 working days of planned catheter placement and a further check image completed within 24 hours prior to catheter placement, with scalp fiducials in situ.

Planning MRI images will be registered with iPlan® Flow Infusion planning software to support finalization of catheter trajectory plan.

NOTE: use of iPlan® Flow software is required for catheter trajectory planning.

Brief medical history and physical and neurological examinations including KPS, noting/recording any changes since screening;
Vital Signs (pulse, respiratory rate, weight and blood pressure)
Review of Baseline Signs and Symptoms noting/recording any changes or new signs/symptoms since screening in medical history; Any changes to concomitant medications will also be recorded;
Treatment Plan (study specific source worksheet) will be completed and reported to hospital pharmacy for dispensing infusate at the time required on Day 0.
Study Drug Administration (Day 0)

On Day 0 subjects will undergo the following procedures and assessments:
Catheter placement and infusion, per the above.
See above tables for example of mandatory antibiotic/H-2 antagonist therapy and for optional dexamethasone and mannitol therapy for management of raised intra-cranial pressure (ICP).

Throughout entire surgical workflow for catheter placement and infusion vital signs (pulse, respiratory rate and blood pressure) will be performed according to institutional best practice; study specific vital signs check points during the surgical workflow are as follows:
Vital signs taken prior to initiation of anesthesia
Vitals signs taken following placement of all catheters but prior to patient being loaded into MRI machine for the real-time infusion monitoring segment
Vital signs taken approximately 1 hour post initiation of infusion
Site will record any abnormal vitals observed at any time during surgical vital signs monitoring as unscheduled findings
Any AEs experienced or concomitant medications received during the catheter placement procedure or during the infusion will be recorded in the subjects' medical records and EDC system NOTE: Subjects will likely be admitted to hospital for 2 nights.
Interruption or Discontinuation of Infusion If a subject experiences a clinically significant Grade 3 or 4 AE considered by the Investigator to be related to the study drug or due to infusion procedure, the infusion will be stopped. Infusion may be restarted at the Investigator's discretion if the AE responds to medical management; otherwise, the infusion should be discontinued permanently.

Should an interruption of the infusion be due to observed mass effect/increased intracranial pressure (ICP), treatment with mannitol is suggested (see above) with infusion resuming after recovery (if possible), such that it can be completed within the maximum infusion duration window of 48 hours.

Treatment may be discontinued at the discretion of the Investigator. In the unlikely event that all catheters are placed erroneously (not in line with placement guidelines) or cannot be used (e.g. catheters do not function/convect), the procedure will be halted and no infusion given to the subject.

End of Infusion (Day 1-2)

These procedures must be completed at the end of the infusion:

A standard 12 Lead ECG (triplicate assessment) will be performed immediately following completion of the infusion (within 2 hours)

MRI for final evaluation of drug distribution (with catheters maintained in place) will be performed within 4 hours (ideally within 2 hours) following completion of infusion Removal of catheters and closure of incisions in accordance with institutional practice at bedside. NOTE: catheters are only removed after the end of infusion MRI is performed.

Collection of blood samples for PK analysis as soon as possible but not more than 1 hour following infusion end time, approximately 3 hours following completion of infusion and then (after the ~3 hour sample collection) every 6 hours±2 hours until 24 hours or until subject is discharged from the hospital (whichever occurs first)

Blood samples for hematology, serum chemistry, and coagulation shall be taken in parallel with either the PK blood collection that is performed within 1 hour following completion of infusion or the PK blood collection that is performed ~3 hours following completion of infusion.

Brief medical history and physical and neurological examinations including KPS, noting any changes since prior to study drug administration shall be performed when the subject is ambulatory prior to hospital discharge.

Vital signs (pulse, respiratory rate, blood pressure and weight) taken when the subject is ambulatory prior to hospital discharge.

Any AEs and new concomitant medications and/or changes to concomitant medications will be recorded throughout entire hospitalization period.

Post-Treatment Follow-Up Assessments

Assessment of safety will be performed on Day 14 (±3 days) after infusion. Both efficacy and safety assessments will be performed on Days 30 (±3), 60 (±7), 90 (±. 7), 120 (±7), 180 (±7), 240 (±7), and 360 (±7) after start of infusion. Unscheduled MRI exams may be required for confirmation of overall response status when preliminary CR or PR or PD (modified RANO criteria; see APPENDIX 2) by repeat assessment 4 weeks after it is observed (required if preliminary response or preliminary progression is observed at Day 120, 180, 240 or 360).

Following completion of the Day 360 end of study visit, subjects will be contacted by telephone at 18 and 24 months to determine disease/survival status. Subjects who discontinue before the Day 360 visit will undergo all the procedures scheduled for the Day 360 visit, and, if possible, followed for disease status, disease related treatments and survival.

14 Days (±3 days) After Infusion

Subjects will return 14 (±3) days after infusion.

Concomitant medications/therapies and AEs will be assessed by asking non-leading questions, and the following procedures will also be performed:

Vital signs (pulse, respiratory rate, weight and blood pressure)

Physical and neurological examinations including KPS

Hematology, serum chemistry, and coagulation

Collection of a blood sample for immunogenicity;

Collection of a blood sample for PK 30, 60, 90, 120, 180, 240, and 360 Days After Infusion Subjects will return on Days 30 (±3), 60 (±7), 90 (±7), 120 (±7), 180 (±7), 240 (±7), and 360 (±7) after infusion to undergo follow-up MRI. For sites that are using TRAMs, delayed contrast extravasation MRI can be performed on Days 30, 60, 90, 120 and 180 for calculation of TRAMs image map to be used for exploratory analyses of tissue response (calculation of TRAMs may be performed at the other follow up visits as or if requested by the Investigator so long as the baseline acquisition is available).

At all of the above named visits concomitant medications/therapies and AEs will be assessed by asking non-leading questions, and the following procedures will also be performed:

Physical and neurological examinations including KPS.

Vital signs (pulse, respiratory rate, weight and blood pressure).

Hematology, serum chemistry, and coagulation.

Serum pregnancy test (female subjects; Day 30 and Day 180 visits only).

Collection of blood samples for immunogenicity (Day 30, Day 120, Day 240 and Day 360 or early termination).

At any time-point during the follow-up period, should analyses on tumor tissue sample material occur at the discretion of the Investigator (e.g. biopsies to establish tissue response status), result should be recorded and material retained for biomarker analysis, where possible.

Other assessments will be performed at the Investigator's discretion and as necessary to follow up any AEs previously recorded.

The Day 360 visit will be equivalent to the early termination visit and will end the subject's safety reporting.

Early Termination Visit

Subjects who discontinue before the Day 360 visit will undergo all the procedures scheduled for the Day 360 visit if early termination is between follow-up visit time points. A new/repeat MRI will not be required if the last MRI performed was within 2 weeks prior to the early termination date, results from this prior MRI will be carried forward for the early termination assessment. When early termination is within 2 weeks following study follow up visit time point (i.e. Day 30, 60, 90, 120, 180 or 240) that visit will be considered the early termination time point and no additional assessments beyond the respective visit date assessments will be required. In the event that a subject is withdrawn from the study prior to the Day 360 visit, post-study follow-up should ensue (see below).

Post-Study Follow-Up

Subjects will be contacted by telephone at 18 and 24 months after completing treatment to assess survival status. Subjects who complete the Day 360 study follow up visit without disease progression or discontinue early without disease progression will continue to be followed for disease status until progression, where possible. After progression (on study or during post-study follow-up), subjects will continue to be followed for survival and post-study treatment(s) for GB and imaging for GB, where possible, until death (or termination of data collection by the Sponsor or withdrawal of consent by the subject).

Usage of Concomitant Medications

All concurrent medical conditions and complications of the underlying malignancy will be treated at the discretion of the Investigator according to acceptable local standards of medical care. Subjects should receive analgesics, antiemetics, antibiotics, anti-pyretics, and blood products as necessary. Although warfarin-type anticoagulant therapies are permitted, careful monitoring of coagulation parameters is imperative to avoid complications of any possible drug interactions. All concomitant medications, including transfusions of blood products, will be recorded in the EDC system.

Guidelines for treating certain medical conditions are discussed below; however, institutional guidelines for the treatment of these conditions may also be used. The concomitant therapies that warrant special attention are discussed below.

Antiemetic Medications

Dexamethasone and a 5-HT3 blocker (e.g., ondansetron or granisetron) may be administered to subjects as pre-medications unless contraindicated for the individual subject. Antiemetics will also be prescribed as clinically indicated during the study period.

Colony Stimulating Factors

Though unlikely to be needed, the use of granulocyte colony-stimulating factors is permitted to treat subjects with neutropenia or neutropenic fever but not to allow for study eligibility.

Dietary Restrictions

None.

Prohibited Medications

The following therapies are not contemplated for inclusion as part of the present study:
  Other anti-neoplastic therapy, including cytotoxics, targeted agents, endocrine therapy, or other antibodies, including Avastin® (bevacizumab) with any treatment intent
  Radiotherapy
  Any other investigational therapy Should such therapies be administered if a subject is withdrawn from the study due to progressive disease, relevant disease related treatment data will continue to be collected until death or termination of data collection by the Sponsor or withdrawal of consent by the subject.

Results

Evaluation of Efficacy

Objective Response Rate

Objective Response Rate (ORR) is the proportion of subjects who achieved a confirmed, durable complete response (CR) or confirmed, durable partial response (PR) out of all treated subjects.

According to the modified RANO criteria, a responder is defined by radiographic and clinical criteria (see Appendix 2). CR and PR will be first assessed by radiographic changes as determined by an improvement of the bi-dimensional evaluation of the tumor size. In addition, changes in neurologic function and steroid use will be considered to determine overall objective response status. Volumetric change in contrast enhancing tumor size will also be examined as an exploratory measure of treatment efficacy.

PRX 321 shares many properties with immunotherapies, including the possibility of response following prolonged (>3 months) pseudo-progression (Weber et al., 2003a; 2003b). Therefore, progression will be assessed using a modification of the standard RANO criteria (see below and Appendix 2).

Pseudo-progression is an increase in contrast enhancement on MRI without true tumor progression. Failure to recognize this phenomenon may result in a premature withdrawal from the study. Subjects with pseudo-progression frequently develop brain edema, mass effect, and other symptoms, making clinical examination an important component of separation from other causes of imaging change. However, clinical examination alone is not the only factor of consideration in the challenge of determination of pseudo-progression; the amount and extent of enhancement on an MRI may be influenced by factors that are not related to the tumor, such as differences in radiologic techniques, the amount of contrast enhancement administered, the timing of the contrast enhancement in relationship to image acquisition, postsurgical changes, infarction, treatment-related inflammation, seizure activity, subacute radiation effects, radiation or treatment-related necrosis, and changes in corticosteroid doses. The modified RANO criteria and other features of this study are designed to minimize uncertainty in the identification of true progression, as follows:

Imaging assessment will be carried out using current and comprehensive imaging guidelines to help identify pseudo-progression where possible. These guidelines, created by members of the RANO Working Group, are outlined in the protocol Appendix 1) and may also be found in Wen et al., 2010 (standard RANO criteria) and Ellingson et al., 2017 and protocol Appendix 2 (modified RANO criteria). This group developed standardized response criteria (standard RANO criteria) for clinical trials for subjects with brain tumors which accounts for both the known challenges of radiographic assessment of GB and the emerging challenges associated with novel agents. A modified RANO criteria was subsequently introduced to further improve upon operational and scientific weaknesses found after implementation of the standard RANO criteria, including allowing continuation on therapy during initial evidence of radiographic progression in order to confirm subsequent tumor growth and/or identify possible pseudo-progression.

The main features of the modified RANO criteria include:
  precise definitions of measurable and non-measurable disease;
  comment on available imaging techniques which may differentiate pseudo-progression;
  more precise definition of response and progression.
  further minimization of the risk of making treatment decisions based on pseudo-progression by requiring that radiological progression, in the absence of clinical progression, must be confirmed on a subsequent examination before it is considered true progression.

The treating neuro-oncologist and neuro-radiologist (and site-specific tumor board if needed to resolve discrepancy) will assess and quantify the contrast images, T2/FLAIR signal, and all MRI sequences and differentiate them from other causes of signal change including radiation effects, decreased corticosteroid dosing, demyelination, ischemic injury, infection, seizures, and postoperative changes by using clinical history, other parts of the MRI like diffusion weighted imaging (DWI) and perfusion, or another short-interval MRI (TRAMs).

An Imaging Core Lab (Intrinsic Imaging LLC, San Antonio, TX) will be employed to provide independent assessment of response, progression following treatment with PRX 321 according to modified RANO criteria (see Appendix 2).

Identification of signatures that identify pseudo-progression during early progressive enhancement using advanced imaging, including TRAMs, diffusion MRI, perfusion MRI or biopsy. Note: Sites may use preferred local methodologies to aid in differentiation of true and pseudo-progression.

Time-to-Event Endpoints

The time-to-event endpoints are defined in Table 16.

TABLE 16

Efficacy Endpoints

| Endpoint | Definition |
| --- | --- |
| Overall Survival (OS) | The time from start of treatment to the date of death from any cause. For subjects who are not known to have died as of the data-inclusion cut-off date, OS time will be censored at the date of the last contact the confirming the subject was alive. OS at 6 (OS-6), 9 (OS-9) and 12 (OS-12) months will also be estimated. |
| Progression-Free Survival (PFS) | The time from start of treatment to the date of confirmed objective progression (per the modified RANO criteria and as determined by independent image review) or death from any cause, whichever occurs first. For subjects who are not known to have died or progressed as of the data-inclusion cut-off date, PFS time will be censored at the date of the last objective progression-free disease assessment prior to the date of any subsequent recurrent GB treatment. PFS at 6 (PFS-6), 9 (PFS-9) and 12 (PFS-12) months will also be estimated. |
| Duration of response (DOR) | The time from first response until confirmed disease progression (per the modified RANO criteria and as determined by independent image review) or death among those subjects achieving a complete response (CR) or partial response (PR) to treatment |
| Duration of clinical benefit (DOCB) | The time from first response or disease stabilization until confirmed disease progression (per the modified RANO criteria and as determined by the Imaging Core Lab) or death among those subjects achieving a CR, PR, or stable disease (SD) |

The use of MRI is mandatory to determine tumor response and to assess when objective progressive disease has occurred (for use in estimating PFS, DOR, and DOCB).

Evaluation of Safety

Each subject receiving PRX 321 via CED will be evaluable for safety. Safety parameters include all laboratory tests and hematological abnormalities, physical findings, ECG, imaging parameters and AEs.

Each subject will be assessed periodically for the development of any toxicity as outlined herein.

Definitions and reporting procedures for AEs provided in this protocol comply with current ICH E6 and other applicable international and local regulatory requirements. The Medical Monitor will promptly review all information relevant to the safety of PRX 321. The Investigator will carefully monitor each subject throughout the study for AEs and all AEs will be followed until adequately resolved. CTCAE 4.0 will be used to determine severity of AEs and SAEs.

Definitions

Adverse Event

An AE (also known as an adverse experience) is defined as any untoward medical occurrence associated with the use of a drug in humans, whether or not considered drug related. More specifically, an AE can be any unfavorable and unintended sign (e.g., an abnormal laboratory finding), symptom, or disease temporally associated with the use of a drug, without any judgment about causality. An AE can arise from any use of the drug (e.g., off-label use, use in combination with another drug) and from any route of administration, formulation, or dose, including an overdose.

Any condition present before the catheter placement, including pre-existing conditions and pre-study AEs, will be considered medical history and will not be reported as a treatment-emergent AE unless the condition worsens during or after catheter placement.

Any worsening (i.e., any clinically significant adverse change in frequency and/or intensity) of a preexisting condition, which is temporally associated with the use of the Sponsor's product, is also an AE.

Adverse Reaction

An adverse reaction is defined as any AE caused by the use of a drug. Adverse reactions are a subset of all suspected adverse reactions for which there is reason to conclude that the drug caused the event.

Suspected

A suspected adverse reaction is defined as any AE for which there is a reasonable possibility that the drug caused the AE. For the purposes of IND safety reporting, "reasonable possibility" indicates that there is evidence to suggest a causal relationship between the drug and the AE. A suspected adverse reaction implies a lesser degree of certainty about causality than an adverse reaction.

Serious

An AE or suspected adverse reaction is considered serious if, in the view of either the Investigator or Sponsor, it results in any of the following outcomes:

Death

Life-threatening AE an AE or suspected adverse reaction is considered life-threatening if, in the view of either the Investigator or Sponsor, its occurrence places the subject at immediate risk of death. It does not include an AE or suspected adverse reaction that, had it occurred in a more severe form, might have caused death.

Inpatient hospitalization or prolongation of existing hospitalization applies if the reported AE requires at least a 24 hour in-patient hospitalization or, if in the opinion of the Investigator, prolongs an existing hospitalization. A hospitalization for an elective procedure or a routinely scheduled treatment is not an SAE by this criterion because a "procedure" or a "treatment" is not an untoward medical occurrence. An emergency room visit of less than 24 hours by itself does not constitute a SAE.

A persistent or significant incapacity or substantial disruption of the ability to conduct normal life function Congenital anomaly/birth defect
applies if a subject exposed to a medicinal (investigational) product gives birth to a child with congenital anomaly or birth defect.

Medical and scientific judgment should be exercised in determining seriousness in other situations, such as important medical events that may not be immediately life-threatening, result in death, or hospitalization, but may jeopardize the subject or may require intervention to prevent one of the other outcomes listed in the definition above.

Examples of such events are intensive treatment in an emergency room or at home for allergic bronchospasm; blood dyscrasias or convulsions that do not result in hospitalization.

Evaluating and Recording of Adverse Events

At each visit, all AEs that are observed, elicited by the Investigator, or reported by the subject will be recorded in the appropriate section of the EDC System and evaluated by the Investigator and the Medical Monitor.

Minimum information required for each AE includes description of the event, duration (start and end dates), severity, assessment of seriousness, and causal relationship to study drug and delivery/infusion procedure.

If discernible at the time of completing the AE section in the EDC System, a specific disease or syndrome rather than individual associated signs and symptoms should be identified by the Investigator and recorded in the appropriate AE section in the EDC System. However, if an observed or reported sign, symptom, or clinically significant laboratory anomaly is not considered by the Investigator to be a component of a specific disease or syndrome, then it should be recorded as a separate AE in the appropriate AE section in the EDC System (clinically significant laboratory abnormalities are those that are identified as such by the Investigator and/or those that require intervention).

Relatedness of Adverse Events

The Investigator will assign attribution of the possible association of the event with use of the investigational drug and, separately, for the surgical/infusion procedure (i.e. AEs that occur during catheter placement prior to start of infusion of study treatment versus AEs with onset after start of infusion). Relationship will be determined for each as follows:

Related: There is evidence to suggest a causal relationship between the drug and the AE, such as:

An event that is uncommon and known to be strongly associated with drug exposure (e.g., angioedema, hepatic injury, Stevens-Johnson Syndrome)

An event that is not commonly associated with drug exposure, but is otherwise uncommon in the population exposed to the drug (e.g., tendon rupture)

Unrelated: Another cause of the AE is more plausible (e.g., due to underlying disease or occurs commonly in the study population), or a temporal sequence cannot be established with the onset of the AE and administration of the study treatment, or a causal relationship is considered biologically implausible.

In general, AEs that are worsening of baseline or pre-existing conditions are considered unrelated, unless there is reason to believe that the worsening was attributable to the investigational drug. Further, if death occurs due to progressive disease it is not considered attributable to PRX 321.

Severity of Adverse Events

The severity of AEs will be graded and recorded by the Investigator using the National Cancer Institute CTCAE version 4.0 guidelines. When specific AEs are not listed in the CTCAE 4.0 they will be graded by the Investigator as none, mild, moderate or severe according to the following grades and definitions:

Grade Definition
Grade 0: No AE (or within normal limits).
Grade 1: Mild; asymptomatic or mild symptoms; clinical or diagnostic observations only; intervention not indicated
Grade 2: Moderate; minimal, local, or noninvasive intervention (e.g., packing, cautery) indicated; limiting age-appropriate instrumental activities of daily living (ADL)
Grade 3: Severe or medically significant but not immediately life-threatening; hospitalization or prolongation of hospitalization indicated; disabling; limiting self-care ADL
Grade 4: Life-threatening consequences; urgent intervention indicated
Grade 5: Death related to AE Follow-Up of Adverse Events All AEs will be followed with appropriate medical management until resolved. Subjects withdrawn from study for unacceptable AEs will be followed until resolution or stabilization of the AE. For selected AE for which administration of the investigational drug was stopped, a re-challenge of the subject with the investigational drug may be conducted if considered both safe and ethical.

Statistical Methods

Determination of Sample Size

A single-stage binomial design test for a null ORR of 6% versus an alternative ("pursue") ORR of 18%, at alpha=0.1, 1-sided, will have 80% power with 36 evaluable subjects (PASS 14, 2016; Fleming, T. R. 1982. 'One-sample multiple testing procedure for Phase II clinical trials.' Biometrics, Volume 38, pages 143-151). To account for the possibility that approximately 10 to 15% of patients will not meet the criteria for evaluable (see below), it is planned to enroll approximately 52 subjects in the trial, including approximately 35 under Protocol Version 3.0.

Evaluable subjects will be those who receive any amount of study drug and have adequate imaging or clinical data for the primary analysis; this will be the primary analysis population (mITT) and will include all patients evaluable on study from all protocol versions. A secondary analysis of the primary endpoint using the same hypotheses and alpha will be conducted on the subjects enrolled under Protocol Version 3.0 onwards, including patients treated similarly under previous protocol versions. These primary and secondary analyses will be conducted in a fixed sequence, primary first, and allowing that the secondary analysis will be descriptive only in case the primary analysis fails to reach statistical significance. This will control the overall trial false positive rate at 10% (one-sided). With 36 mITT subjects there will be approximately 80% power for the secondary test and, with more than 36 mITT subjects pooled, more than 80% power for the primary test.

Statistical and Analytical Plans

The primary analysis will occur when all subjects have completed the Day 360 visit or discontinued prior to completing the Day 360 visit. All available data will be analyzed at the primary analysis. Collection of follow-up data will continue until all patients have withdrawn from follow-up. Supplementary reports, presenting updated time-to-event data, will be prepared after completion of the 2 year survival follow-up period and beyond, if required.

Descriptive statistics will be presented including the number and percent for categorical variables and the number of observations, mean, standard deviation, median, and range for continuous variables; 95% confidence intervals (CIs) will be presented as appropriate.

Randomization

This study is a single-arm design. All subjects will receive active treatment. No randomization will be performed.

Analysis Populations

Modified Intent to Treat (mITT)

The assessment of treatment effect and efficacy will be performed on the mITT population. The mITT population will comprise all subjects who receive any amount of study drug and have adequate imaging or clinical data for the primary analysis from all protocol versions; this will be the primary analysis population (mITT).

The secondary analysis population (see below) will comprise all subjects enrolled under Protocol Version 3.0 and onwards, including patients treated similarly under previous protocol versions, who receive any amount of study drug and have adequate imaging or clinical data for the primary analysis.

NOTE: Patients who expire or progress clinically prior to the first MRI examination will not be evaluable for any of the response assessments.

Per Protocol (PP) Population

The PP population will comprise all patients in the mITT population who also have no major protocol violations during the study. This population will be finalized prior to the final lock and primary analysis of the study data. Efficacy analyses will be conducted on this population in support of the primary efficacy results.

IL-4R Analysis Population

The IL-4R Analysis Population will be the same as the mITT Population and will be used for efficacy analyses stratified by IL-4R level.

Safety Population

The Safety population will comprise all patients treated on study. Safety analyses will be presented on this population.

Baseline and Demographic Characteristics

Baseline and demographic characteristics will be summarized and presented descriptively.

Analysis of Efficacy

Primary Efficacy Variable

ORR will be presented as the percentage of subjects with CRs or PRs by the modified RANO criteria (Appendix 2) with respect to pre-operative planning MRI (baseline); only confirmed responses (i.e., those observed on 2 consecutive MRI scans not less than 4 weeks apart while on a stable corticosteroid use for 14 days before each scan at the same dose administered at the time of the previous scan or at the reduced dose, with stable or improved neurologic condition) will be considered.

Secondary Efficacy Variables

Secondary Efficacy Variables Will be OS and PFS.

OS and PFS will be summarized using the Kaplan-Meier method, including graphical displays and incidence estimates at 6, 9, and 12 months. OS will also be tested in secondary analyses using a single sample logrank test with null and alternative hypotheses pre-specified in the Statistical Analysis Plan prior to primary analysis of the study. This hypothesis test will be conducted in a fixed sequence analysis with the primary hypothesis test of ORR so as to control the overall trial false positive rate. If the primary ORR analysis fails at the pre-specified significance level the secondary OS analysis will be considered purely exploratory and significance will not be claimed.

OS will be defined as the time (in weeks) from start of the infusion until death from any cause. Subjects not know to have died at the time of the analysis will be censored at the time of last contact.

PFS will be defined as the time (in weeks) from start of the infusion until radiologic or neurologic disease progression or death from any cause. Subjects not know to have died or experienced disease progression at the time of the analysis will be censored at the time of the last radiologic assessment demonstrating lack of progression or, if during the follow-up period, the time of last contact indicating lack of progression.

Other Efficacy Variables and Analyses

DOR will be summarized using the Kaplan-Meier method, including graphical displays. DOR will be calculated only for the subset of subjects with a response (CR or PR), and it will be defined as the time (in weeks) from first response until radiologic disease progression (per the modified RANO criteria and as determined by independent image review) or death from any cause. Responders alive and progression-free at the time of the analysis will be censored at the time of the last radiologic assessment demonstrating lack of progression or, if during the follow-up period, the time of last contact indicating lack of progression.

DOCB will be summarized using the Kaplan-Meier method, similar to DOR. DOR will be calculated only for the subset of subjects with a stable disease or better (CR, PR, or SD), and it will be defined as the time (in weeks) from first response until radiologic disease progression (per the modified RANO criteria and as determined by independent image review) or death from any cause. Censoring will be performed in a fashion similar to DOR.

Additional, exploratory, efficacy variables may include ORR and PFS based on the Investigator's assessment of response and other time-to-event endpoints (e.g., time to post-study treatment of GB). Analyses will also be conducted by IL-4R stratum, including 95% confidence interval estimates of ORR within strata and examination of the treatment effect by IL-4R level.

Efficacy analyses will also explore subject subsets (procedural success, IL-4R level, sequence number by site [learning], tumor size, tumor coverage, time of infusion, maximum flow rate, number of catheters, percentage of planned infusate administered, KPS, gender, age, steroid use, immune status) and response by other applicable criteria. Subgroup and sensitivity analyses comparing subjects included before and after protocol version 3.0 may be explored.

Analysis of Safety Variables

Safety variables, including AEs, laboratory results, vital signs, ECGs, antibody assessments, and serum drug levels on PK samples, will be summarized and presented, by study time where appropriate.

AEs will be coded using the Medical Dictionary for Regulatory Activities (MedDRA). Cancer Therapy Evaluation Program (CTEP) Common Terminology Criteria for Adverse Events NCI CTCAE v4.0 will be used to grade the severity of AEs. Treatment emergent AEs will be summarized by system organ class (SOC) and by preferred terms for all treated subjects and subset of subjects of interest. Certain summaries of the treatment-emergent AEs will also be generated by severity, relationship to study drug, relationship to infusion, catheter placement, volume of infusate, and prior therapies. Proportion of patients experiencing Grade 3 and 4 laboratory test results will be summarized.

MRI Analysis

Exploratory analyses will be performed to assess the relationships between planned tissue coverage, actual tissue coverage, tissue toxicity, tissue response (TRAMs correlation) and clinical results and IL-4R expression. These analyses will be descriptive in nature.

Tumor Tissue Analysis

Exploratory analyses will be performed to assess the relationship of IL-4R expression levels in tumor tissue with treatment response, tissue response and survival. This analysis will be descriptive in nature.

References

Assaf Shapira and Itai Benhar. Review Toxin-Based Therapeutic Approaches. Toxins 2010, 2, 2519-2583.

Bankaitis K V and Fingleton B. Targeting IL4/IL-4R for the treatment of epithelial cancer metastasis. Clin Exp Metastasis. 2015 December; 32 (8): 847-56.

Brem H, Piantadosi S, Burger P C, et al. Placebo-controlled trial of safety and efficacy of intraoperative controlled delivery by biodegradable polymers of chemotherapy for recurrent gliomas. Lancet 1995; 345:1008-12.

Butowski N, et al. Abstract: Initial Clinical Development of a Nano-liposomal Formulation of CPT-11. 2015 SNO-SCIDOT Joint Conference. http://www.soc-neuro-onc.org/therapeutic-delivery-conference/

Chandramohan V, Sampson J H, Pastan I, et al. Toxin-based targeted therapy for malignant brain tumors. Clin Dev Immunol. 2012; 2012:480429.

Chen M Y, et al., Variables affecting convection-enhanced delivery to the striatum: a systematic examination of rate of infusion, cannula size, infusate concentration, and tissue-cannula sealing time. J Neurosurg 1999; 90 (2): 315-20.

Chiron M F, Fryling C M, FitzGerald D. Furin-mediated cleavage of *Pseudomonas* exotoxin-derived chimeric toxins. J Biological Chemistry; 272:50, 31707-11.

Chittiboina P, Heiss J D, Warren K E, Lonser R R. Magnetic resonance imaging properties of convective delivery in diffuse intrinsic pontine gliomas. J Neurosurg Pediatr 2014 March; 13 (3): 276-82.

Cohen M H, Yuan L S, Keegan P, Pazdur R. FDA Drug Approval Summary: Bevacizumab (Avastin®) as Treatment of Recurrent Glioblastoma Multiforme. The Oncologist 2009; 14:1131-38.

Daniels et al. Early biomarkers from conventional and delayed-contrast MRI to predict the response to bevacizumab in recurrent high-grade gliomas. AJNR Am J Neuroradiol. 2016 Jul. 7.

De Jong M C, Scheffer G L, Broxterman H J, et al. Multidrug-resistant tumor cells remain sensitive to a recombinant interleukin-4-*Pseudomonas* exotoxin, except when overexpressing the multidrug resistance protein MRP1. Clin Cancer Research 2003; 9:5009-17.

Ding D, Kanaly C W, Cummings T J, et al. Long term safety of combined intracerebral delivery of free gadolinium and targeted chemotherapeutic agent PRX 321. Neurol Res 2010 October; 32 (8): 810-5.

Ellingson B M, Bendszus M, Boxerman J, et al. Consensus recommendations for a standardized Brain Tumor Imaging Protocol in clinical trials. Neuro-Oncology 2015; 17 (9): 1188-98.

Ellingson B M, Wen P Y, Cloughesy T F. Modified Criteria for Radiographic Response Assessment in Glioblastoma Clinical Trials. Neurotherapeutics. 2017 Jan. 20. doi: 10.1007/s13311-016-0507-6. [Epub ahead of print] PubMed PMID: 28108885.

Fiandaca M S, et al. Image-guided convection-enhanced delivery platform in the treatment of neurological diseases. Neurotherapeutics 2008; 5 (1): 123-7.

Fiandaca M S, et al. Real-time M R imaging of adeno-associated viral vector delivery to the primate brain. Neuroimage 2009; 47 Suppl 2: T27-35.

Floeth F W, et al. Comparative follow-up of enhancement phenomena with MRI and Proton M R Spectroscopic Imaging after intralesional immunotherapy in glioblastoma—Report of two exceptional cases. Zentralbl Neurochir. 2002; 63 (1): 23-8.

Friedman H S, et al. Bevacizumab alone and in combination with irinotecan in recurrent glioblastoma. J Clin Oncol 2009 Oct. 1; 27 (28): 4733-40.

Gill S S, et al. Direct brain infusion of glial cell line-derived neurotrophic factor in Parkinson disease. Nat Med 2003; 9 (5): 589-95.

Gill T, Barua N U, Woolley M, et al. In vitro and in vivo testing of a novel recessed-step catheter for reflux-free convection-enhanced drug delivery to the brain. J Neurosci Methods. 2013 Sep. 30; 219 (1): 1-9.

Hadaczek P, et al. The "perivascular pump" driven by arterial pulsation is a powerful mechanism for the distribution of therapeutic molecules within the brain. Mol Ther 2006; 14 (1): 69-78.

Hall W A, Fodstad A E. Immunotoxins and central nervous system neoplasia. J Neurosurg 1992; 76:1-2.

Hamilton J F, et al. Heparin coinfusion during convection-enhanced delivery (CED) increases the distribution of the glial-derived neurotrophic factor (GDNF) ligand family in rat striatum and enhances the pharmacological activity of neurturin. Exp Neurol 2001; 168 (1): 155-61.

Harshyne L A, Nasca B J, Kenyon L C, et al. Serum exosomes and cytokines promote a T-helper cell type 2 environment in the peripheral blood of glioblastoma patients. Neuro Oncol 2016 February; 18 (2): 206-15.

Healy A T, Vogelbaum M A. Convection-enhanced drug delivery for gliomas. Surg Neurol Int 2015 Feb. 13; 6 (Suppl 1): S59-67.

Huang H. Lin H. Zhang X. Li J. Resveratrol reverses temozolomide resistance by downregulation of MGMT in T98G glioblastoma cells by the N F-κ B-dependent pathway. Oncology Reports 2012; 27:2050-56.

Jahangiri A, Chin A T, Flanigan P M, et al. Convection-enhanced delivery in glioblastoma: a review of preclinical and clinical studies. J Neurosurg. 2016 Apr. 1:1-10.

Jarboe J, Johnson K, Choi Y, et al., Expression of interleukin-13 receptor A2 in glioblastoma multiforme: Implications for targeted therapies. Cancer Res 2007; 67 (17): 7983-6.

Joshi B H, Leland P, Asher A, et al. In situ expression of interleukin-4 (IL-4) receptors in human brain tumors and cytotoxicity of a recombinant IL-4 cytotoxin in primary glioblastoma cell cultures. Cancer Res 2001; 61:8058-61.

Joshi B H, Leland P, Silber J, et al. IL-4 receptors on human medulloblastoma tumours serve as a sensitive target for a circular permuted IL-4-*Pseudomonas* exotoxin fusion protein. British Journal of Cancer (2002) 86, 285-291.

Kanner A A, Wong E T, Villano J L, Ram Z; EF-11 Investigators. Post hoc analyses of intention-to-treat population in phase III comparison of NovoTTF-100 ATM system versus best physician's choice chemotherapy. Semin Oncol. 2014; 41 (suppl 6): S25-S34.

Kawakami M, Kawakami K, Stepensky V A et al. IL4-R on Human Lung Cancer A molecular target for cytotoxin therapy. Clin Cancer Res 2002; 8:3503-11.

Keles G E, Lamborn K R, Chang S M, et al. Volume of residual disease as a predictor of outcome in adult patients with recurrent supratentorial glioblastoma multiforme who are undergoing chemotherapy. J Neurosurg 2004; 100:41-6.

Kennedy B, Showers C, Anderson D, et al. Tumor-associated macrophages in glioma: friend or foe? J Oncol. 2013; 2013:486912.

Kohanbash G, McKaveney K, Sakaki M, et al. G M-CSF promotes the immunosuppressive activity of glioma-infiltrating myeloid cells through interleukin-4 receptor-a. Cancer Res. 2013; 73 (21): 6413-23.

Kokkinakis D M, Ahmed M M, Chendil D, et al. Sensitization of pancreatic tumor xenografts to carmustine and temozolomide by inactivation of their 06-methylguanine-DNA methyltransferase with 06-benzylguanine or 06-benzyl-2'-deoxyguanosine. Clin Cancer Res 2003; 9:3801-07.

Krauze M T, et al. Real-time visualization and characterization of liposomal delivery into the monkey brain by magnetic resonance imaging. Brain Res Brain Res Protoc 2005a; 16 (1-3): 20-6.

Krauze M T, Saito R, Noble C, et al. Reflux-free cannula for convection-enhanced high-speed delivery of therapeutic agents. J Neurosurg 2005b; 103:923-29.

Kreitman R J, Puri R K, Pastan I. A circularly permuted recombinant interleukin 4 toxin with increased activity. Proc Natl Acad Sci USA 1994; 91:6889-93.

Kreitman R J, Puri R K, Pastan I. Increased antitumor activity of a circularly permuted interleukin 4-toxin in mice with interleukin 4 receptor-bearing human carcinoma. Cancer Res 1995; 55:3357-63.

Kunwar S, Chang S, Westphal M, et al. Phase III randomized trial of CED of IL13-PE38QQR vs Gliadel wafers for recurrent glioblastoma. Neuro Oncol 2010; 12:871-81.

Kuo C C, Liu J F, Shiah H S, et al. Tamoxifen accelerates proteasomal degradation of 06-methylguanine DNA methyltransferase in human cancer cells. Int. J. Cancer 2007; 121:2293-2300.

Levin V A, Mendelssohn N D, Chan J, et al. Impact of bevacizumab administered dose on overall survival of patients with progressive glioblastoma. J Neurooncol 2015 March; 122 (1): 145-50.

Levin V A, Tonge P J, Gallo J M, et al. CNS Anticancer Drug Discovery and Development Conference White Paper Neuro-Oncology 17: vil-vi26, 2015

Lewis O, Woolley M, Johnson D, et al. Chronic, intermittent convection-enhanced delivery devices. J Neurosci Methods 2016 Feb. 1; 259:47-56.

Lonser R R, Sarntinoranont M, Morrison P F, et al. Convection-enhanced delivery to the central nervous system. J Neurosurg 2015 March; 122 (3): 697-706.

Lonser R R, Warren K E, Butman J A, et al. Real-time image guided direct convective perfusion of intrinsic brainstem lesions. Technical note. J Neurosurg 2007; 107 (1): 190-7.

Mardor Y, Last D, Daniels D, et al. Convection-Enhanced Drug Delivery of Interleukin-4, Pseudomonas Exotoxin (PRX 321): Increased Distribution and Magnetic Resonance Monitoring. JPET 330:520-525, 2009.

Marks W J Jr., et al. Gene delivery of AAV2-neurturin for Parkinson's disease: a double-blind, randomized, controlled trial. Lancet Neurol 2010; 9 (12): 1164-72.

Mercapide J, Lopez De Cicco R, Bassi D E, et al. Inhibition of furin-mediated processing results in suppression of astrocytoma cell growth and invasiveness. Clin Cancer Res 2002 June; 8 (6): 1740-6.

Merchant F, Fidai S, Patel B. Inhibition of Pancreatic And Colon Cancer cells and/or cancer stem cells By Targeting ILA-Ra With PRX 321. Abstract #420. Innovations in Cancer Prevention and Research Conference. Nov. 9-10, 2015, Austin, Texas.

Morrison P F, et al. Focal delivery during direct infusion to brain: role of flow rate, catheter diameter, and tissue mechanics. Am J Physiol 1999; 277 (4 Pt 2): R1218-29.

Murad G J, et al. Real-time, image-guided, convection-enhanced delivery of interleukin 13 bound to *pseudomonas* exotoxin. Clin Cancer Res 2006; 12 (10): 3145-51.

Neeves K B, et al. Dilation and degradation of the brain extracellular matrix enhances penetration of infused polymer nanoparticles. Brain Res 2007; 1180:121-32.

Nguyen J B, et al. Convection-enhanced delivery of AAV-2 combined with heparin increases T K gene transfer in the rat brain. Neuroreport 2001; 12 (9): 1961-4.

Nguyen T T, et al. Convective distribution of macromolecules in the primate brain demonstrated using computerized tomography and magnetic resonance imaging. J Neurosurg 2003; 98 (3): 584-90.

Puri et al., A review of studies on targeting interleukin 4 receptor for central nervous system malignancy. Curr Mol Med 2009; 9:732-39.

Puri R K, Hoon D S, Leland P, et al. Preclinical development of a recombinant toxin containing circularly permuted interleukin 4 and truncated *pseudomonas* exotoxin for therapy of malignant astrocytoma. Cancer Res 1996; 56:5631-37.

Puri R K, Leland P, Kreitman R J, et al. Human neurological cancer cells express interleukin-4 (IL-4) receptors. Int. J. Cancer 1994; 58:574-81.

Puri S., Joshi, B H, Sarkar C et al. Expression and structure of interleukin 4 receptors in primary meningeal tumors. Cancer, 2005, 103:2132-2142.

Rand R W, Kreitman R J, Patronas N, et al. Intratumoral administration of recombinant circularly permuted interleukin-4-*pseudomonas* exotoxin in patients with high-grade glioma. Clin Can Res 2000; 6:2157-2165.

Richardson R M, et al. Novel platform for MRI-guided convection-enhanced delivery of therapeutics: preclinical validation in nonhuman primate brain. Stereotact Funct Neurosurg 2011; 89 (3): 141-51.

Rosenbluth K H, Eschermann J F, Mittermeyer G, et al. Analysis of a simulation algorithm for direct brain drug delivery. Neuroimage. 2012 Feb. 1; 59 (3): 2423-9.

Rosenbluth K H, Luz M, Mohr E, et al. J Neurosci Methods. Design of an in-dwelling cannula for convection-enhanced delivery. 2011 Mar. 15; 196 (1): 118-23.

Sampson J H, Archer G, Pedain C, et al. Poor drug distribution as a possible explanation for the results of the PRECISE trial. J Neurosurg. 2010; 113 (2): 301-9.

Sampson J H, Brady M, Raghavan R, et al. Colocalization of gadolinium-diethylene triamine pentaacetic acid with high-molecular-weight molecules after intracerebral convection-enhanced delivery in humans. Neurosurgery. 2011 September; 69 (3): 668-76.

Sampson J H, Raghavan R, Brady M L, et al. Clinical utility of a patient-specific algorithm for simulating intracerebral drug infusions. Neuro-Oncology 2007; 9:343-353.

Shimamura T, Royal R E, Kioi M, et al. Interleukin-4 Cytotoxin Therapy Synergizes with Gemcitabine in a Mouse Model of Pancreatic Ductal Adenocarcinoma. Cancer Res 2007; 67:9903-9912.

Sorensen A G, Patel S, Harmath C, et al. Comparison of diameter and perimeter methods for tumor volume calculation. J Clin Oncol 2001 Jan. 15; 19 (2): 551-7.

Souweidane M M. Editorial: Convection-enhanced delivery for diffuse intrinsic pontine glioma. J Neurosurg Pediatr. 2014 March; 13 (3): 273-5.

Strome S E, Kawakami K, Alejandro D, et al. Interleukin 4 receptor-directed cytotoxin therapy for human head and neck squamous cell carcinoma in animal models. Clin Cancer Res 2002; 8:281-6.

Stupp R, Mason W P, van den Bent M J, Weller M, Fisher B, et al. Radiotherapy plus concomitant and adjuvant temozolomide for glioblastoma. N Engl J Med 2005; 352:987-96.

Varenika V, et al. Detection of infusate leakage in the brain using real-time imaging of convection-enhanced delivery. J Neurosurg, 2008, 109 (5): 874-80.

Verma N, Cowperthwaite M C, Burnett M G and Markey M K. Differentiating tumor recurrence from treatment necrosis: a review of neuro-oncologic imaging strategies. Neuro Oncol. 2013 May; 15 (5): 515-34.

Weber F, Asher A, Bucholz R, et al. Safety, tolerability, and tumor response of IL4-*Pseudomonas* exotoxin (NBI-3001) in patients with recurrent malignant glioma. Journal of Neuro-Oncology 2003a; 64:125-37.

Weber F W, et al. Local convection enhanced delivery of IL4-*Pseudomonas* exotoxin (NBI-3001) for treatment of patients with recurrent malignant glioma. Acta Neurochir Suppl 2003b; 88:93-103.

Wein L M, Wu J T, Lanculescu A G, et al. A mathematical model of the impact of infused targeted cytotoxic agents on brain tumors: implications for detection, design and delivery. Cell Prolif 2002; 35:343-61.

Weller M, Coughesy T, Perry J, Wick W. Standards of care for treatment of recurrent glioblastoma—are we there yet? Neuro Oncol 2013 January; 15 (1): 4-27.

Wen P Y, et al. Response assessment challenges in clinical trials of gliomas. Curr Oncol Rep 2010; 12 (1): 68-75.

Wen P Y, et al. Updated response assessment criteria for high-grade gliomas: response assessment in neuro-oncology working group. J Clin Oncol 2010; 28 (11): 1963-72.

White E, Bienemann A, Malone J, et al. An evaluation of the relationships between catheter design and tissue mechanics in achieving high-flow convection-enhanced delivery. J Neurosci Methods. 2011 Jul. 15; 199 (1): 87-97.

Wick W, Wild-Bode C, Frank B, Weller M. BCL-2-induced glioma cell invasiveness depends on furin-proteases. J Neurochem. 2004 Decl 91 (6): 1275-83.

Yin D, Valles F E, Fiandaca M S, et al. Optimal region of the putamen for image-guided convection-enhanced delivery of therapeutics in human and non-human primates. Neuroimage. 2011 January; 54 Suppl 1: S196-203.

Zach L, Guez D, Last D, et al. Delayed contrast extravasation MRI for depicting tumor and non-tumoral tissues in primary and metastatic brain tumors. PLOS One. 2012; 7 (12): e52008.

Zach L, Guez D, Last D, et al. Delayed contrast extravasation MRI: a new paradigm in neuro-oncology. Neuro Oncol. 2015 March; 17 (3): 457-65.

Response Assessment in Neuro-Oncology (RANO)

In this study, the standard RANO criteria (Wen et al., 2010) will only be used to determine eligibility.

Subjects must have histologically proven primary (de novo) GB that has recurred or progressed (per standard RANO criteria) after treatment(s) including surgery and radiotherapy with or without chemotherapy (according to local practice; Stupp protocol, Stupp et al., 2005) and following discontinuation of any previous standard or investigational lines of therapy (up to 2 prior lines of therapy).

Definition of Progressive Disease Less than 12 Weeks from Completion of Radiochemotherapy Progression can only be defined using diagnostic imaging if there is new enhancement outside of the radiation field (beyond the high dose region or 80% isodose line).

OR

If there is unequivocal evidence of viable tumor on histopathologic sampling (e.g., solid" tumor areas [i.e., >70% tumor cell nuclei in areas], high or progressive increase in MIB-1 proliferation index compared to prior biopsy, or evidence for histologic progression or increased anaplasia in tumor.

Note: Given the difficulty of differentiating true progression from "pseudo-progression", clinical decline alone, in the absence of radiographic or histologic confirmation of progression, will not be sufficient for definition of progressive disease in the first 12 weeks following completion of treatment.

Definition of Progressive Disease at and Beyond 12 Weeks of Radiochemotherapy Completion New contrast-enhancing lesion outside of radiation field on decreasing, stable or increasing doses of corticosteroids.

Increase by 25% or greater in the sum of the products of perpendicular diameters between the first post-radiotherapy scan, or a subsequent scan with smaller tumor size, and the scan at 12 weeks or later on stable or increasing doses of corticosteroids.

Clinical deterioration not attributable to concurrent medication or comorbid conditions is sufficient to declare progression on current treatment, but not for entry on a clinical trial for recurrence.

For patients receiving anti-angiogenic therapy, significant increase in T2/FLAIR non-enhancing lesion may also be considered progressive disease. The increased T2/FLAIR must have occurred with the patient on stable or increasing doses of corticosteroids compared to baseline scan or best response following initiation of therapy, and not due to co-morbid events (e.g., effects of radiotherapy, demyelination, ischemic injury, infection, seizures, post-operative changes, or other treatment effects).

Reference:

Wen PY, Macdonald DR, Reardon D A, et al. Updated response assessment criteria for high-grade gliomas: response assessment in neuro-oncology working group. J Clin Oncol 2010; 28 (11): 1963-1972.

Modified Response Assessment in Neuro-Oncology (Modified RANO) for Malignant Glioma In this study, response and progression following treatment with PRX 321 will be determined according to modified RANO criteria (Ellingson et al. 2017) whereby definitions are outlined below.

The overall objective status is determined by combining the patient's radiographic response on target lesions, new disease, neurological status (KPS), and steroid dose/usage as defined in Table 17 below. Note that patients with possible pseudo-progression (PsP) or pseudo-response should be given the Objective Status of Preliminary Progression or Preliminary Response, respectively. Once PsP, pseudo-response, or true progression/response are confirmed, the Objective Status can be changed accordingly (see definitions below).

TABLE 17

Summary of the Overall Objective Status for the Modified RANO Criteria for Malignant Glioma
(for patients with measurable (>1 cm × 1 cm) disease): (continued on the next page)

| Target Lesions (Current Scan) | Target Lesions (Previous Scan) | New Sites of Measurable Disease [a] | Neurological Status (KPS) | Steroid Usage | Steroid Dose | Overall Objective Status | Action |
|---|---|---|---|---|---|---|---|
| CR | Planning MRI | No | Stable/Better | No | N/A | Preliminary CR | Schedule confirmatory scan in 4 weeks |
| PR | Planning MRI | No | Stable/Better | Any | Stable/Decreased | Preliminary PR | Schedule confirmatory scan in 4 weeks |
| PD | Planning MRI | Yes or No | Stable/Better | Any | Stable/Increased | Preliminary PD | Schedule confirmatory scan in 4 weeks |
| PD | Preliminary or Confirmed PR/CR | No | Stable/Better | Any | Stable/Increased | Preliminary PD | Schedule confirmatory scan in 4 weeks |
| SD | Preliminary or Confirmed CR/PR or SD/NE or Planning MRI | No | Stable/Better | Any | N/A | SD | Continue study imaging schedule |
| PR | Preliminary PR | Yes or No | Stable/Better | Any | Stable/Decreased | Confirmed PR | Continue study imaging schedule |
| SD | Preliminary PR | Yes or No | Stable/Better | Any | Stable/Decreased | SD (Preliminary PR →Confirmed PR) | Continue study imaging schedule |
| SD | Preliminary CR | Yes or No | Stable/Better | Any | Stable/Decreased | SD (Preliminary CR →Confirmed CR) | Continue study imaging schedule |
| CR | Preliminary CR | No | Stable/Better | No | N/A | Confirmed CR | Continue study imaging schedule |
| SD | Preliminary PD | No | Stable/Better | Any | Stable/Decreased | SD (Confirmed PsP) | Continue study imaging schedule |
| CR/PR/SD/PD/NE | CR/PR/SD/PD/NE or Planning MRI | Yes or No | Worse[b] | Any | Stable/Increased | Confirmed PD | Ensure possibility of PsP is excluded prior to withdraw of subject and proceeding to end of study[c] |
| PD | Preliminary PD | Yes or No | Any | Yes | Stable/Increasing | Confirmed PD | Ensure possibility of PsP is excluded prior to withdraw of subject and proceeding to end of study[c] |

[a] Note that new sites of measurable disease are added to the sum of bidimensional products or total lesion volume, or constitutes preliminary PD in the case of no measurable disease at baseline or best response.
[b] Definition of neurological deterioration is left to the discretion of the treating physician, but it is recommended that a decline in the KPS from 100 or 90 to 70 or less, a decline in KPS of at least 20 from 80 or less, or a decline in KPS from any baseline to 50 or less, for at least 7 days, be considered neurologic deterioration unless attributable to comorbid events or changes in corticosteroid dose (Wen et al., 2010)
[c] Investigators encouraged to robustly differentiate between true and pseudo-progression on MRI and other modalities (e.g. perfusion MRI, PET scan, TRAM, biopsy)

Complete Response (CR) Requirements

Disappearance of all enhancing measurable and non-measurable disease sustained for at least 4 weeks. The first scan exhibiting disappearance of all enhancing measurable and non-measurable disease is considered "preliminary CR". If the second scan exhibits measurable enhancing disease with respect to the "preliminary CR" scan, then the response is not sustained, noted as pseudo-response, PsR, and is now considered "preliminary PD" (note confirmed PD requires at least 2 sequential increases in tumor volume). If the second scan continues to exhibit disappearance of enhancing disease or emergence of non-measurable disease (less than 10 mm bidimensional product, it is considered a durable CR and the patient should continue on therapy until confirmed PD is observed.

Patients must be off corticosteroids (or on physiologic replacement doses only).

Stable or improved clinical assessments (i.e. neurological examinations)

Note: Patients with non-measurable disease only at baseline cannot have CR; the best response possible is stable disease (SD).

Partial Response (PR) Requirements

≥50% decrease in sum of products of perpendicular diameters of all measurable enhancing lesions compared with baseline, sustained for at least 4 weeks. The first scan exhibiting ≥50% decrease in sum of products of perpendicular diameters of all measurable enhancing lesions compared with baseline is considered "preliminary PR". If the second scan exhibits PD with respect to the "preliminary PR" scan, then the response is not sustained, noted as pseudo-response, PsR, and is now considered "preliminary PD" (note confirmed PD requires at least 2 sequential increases in tumor size). If the second scan exhibits SD, PR, or CR, it is considered a durable PR and the patient should continue on therapy until confirmed PD is observed.

Steroid dose should be the same or lower compared with baseline scan

Stable or improved clinical assessments

Note: Patients with non-measurable disease only at baseline cannot have PR; the best response possible is stable disease (SD).

Progressive Disease (PD): Defined by any of the following:

At least 2 sequential scans separated by at >4 weeks both exhibiting ≥25% increase in sum of products of perpendicular diameters of enhancing lesions. The first scan exhibiting ≥25% increase in sum of products of perpendicular diameters of enhancing lesions should be compared to the smallest tumor measurement obtained either at baseline (if no decrease) or best response (on stable or increasing steroid dose) and is noted as "preliminary PD." If the second scan at least 4 weeks later exhibits a subsequent ≥25% increase in sum of products of perpendicular diameters of enhancing lesions relative to the "preliminary PD" scan it is considered "confirmed PD" and the patient should discontinue therapy. If the second scan at least 4 weeks later exhibits SD or PR/CR, this scan showing "preliminary PD" is noted as "pseudo-progression", PsP, and the patient should continue on therapy until a second increase in tumor size relative to the PsP scan is observed. Note that any new measurable (>10 mm×10 mm) enhancing lesions should not be immediately considered PD, but instead should be added to the sum of bidimensional products representing the entire enhancing tumor burden.

In the case where the baseline or best response demonstrates no measurable enhancing disease (visible or not visible), then any new measurable (>10 mm×10 mm) enhancing lesions are considered PD after confirmed by a subsequent scan ≥4 weeks exhibiting ≥25% increase in sum of products of perpendicular diameters of enhancing lesions relative to the scan first illustrating new measurable disease. The first scan exhibiting new measurable disease is noted as "preliminary PD." If the second scan at least 4 weeks later exhibits a subsequent ≥25% increase in sum of products of perpendicular diameters of enhancing lesions relative to the "preliminary PD" scan it is considered "confirmed PD" and the patient should discontinue therapy. If the second scan at least 4 weeks later exhibits SD, CR, PR, or becomes non-measurable, this scan showing "preliminary PD" is noted as "pseudo-progression", PsP, and the patient should continue on therapy until a second increase in tumor size relative to the "preliminary PD", or PsP, scan is observed. Note that any new measurable (>10 mm×10 mm) enhancing lesions on the subsequent scan following the preliminary PD scan should not be immediately considered confirmed PD, but instead should be added to the sum of bidimensional products representing the entire enhancing tumor burden.

Clear clinical deterioration not attributable to other causes apart from tumor (e.g. seizures, medication adverse effects, therapy complications, stroke, infection) or attributable to changes in steroid dose.

Failure to return for evaluation as a result of death or deteriorating condition.

Stable Disease (SD) Requirements:

Does not qualify for CR, PR, or PD as defined above. Note this also applies to patients that demonstrate PsR when the confirmation scan does not show PD or PSP when the confirmation scan does not show PR/CR.

In the event that corticosteroid dose was increased (for new symptoms/signs) without confirmation of disease progression on neuroimaging, and subsequent follow-up imaging shows that the steroid increase was required because of disease progression, the last scan considered to show stable disease will be the scan obtained when the corticosteroid dose was equivalent to the baseline dose.

Preliminary Radiographic Progression: If the lesion size has increased >25% bidirectional product between MRI Scan 1 and N, these patients will be categorized as "preliminary radiographic progression". If the investigator believes the patient can safely continue on therapy, then they should continue to treat and acquire a follow-up confirmatory scan [MRI (N+1)] at the next scan interval (8 weeks±4 weeks from MRI Scan (N) or no less than 4 weeks minimum duration between preliminary PD and confirmed PD scans) to verify tumor growth and progression. For patients with gross-total resection (GTR) and no measurable enhancing disease, preliminary radiographic progression is defined as a transition from no measurable disease to non-measureable (but present) disease (<1 cm×1 cm) or measurable disease (>1 cm×1 cm). If the investigator feels it is safe to keep the patient on, a confirmatory scan at MRI (N+1) should be obtained to verify tumor progression.

Confirmed Progression: If the patient has an increase >25% bidirectional product between MRI Scan N and N+1, this is "Confirmed Progression", the patient should stop therapy and the date of radiographic progression is the date of suspected progression, MRI (N). If the patient has SD/PR/CR on MRI (N+1) with respect to MRI (N), PsP is confirmed and the patient should continue on therapy. Patients will then continue on therapy and receive additional follow-up MRI scans [MRI (M)]. If the lesion size has increased >25% bidirectional product on MRI (M) relative to the smaller of Nadir or MRI (N+1), then the patient has "Confirmed Progression", the patient should stop therapy and the date of radiographic progression is the new date, MRI (M). For patients with no measurable disease at the Post-RT baseline, "Confirmed Progression" will be defined as a transition from non-measurable (but present) disease (<1 cm×1 cm) on MRI (N) to measurable disease (>1 cm×1 cm) on MRI (N+1). For patients with confirmed PsP and no measurable disease at Nadir, "Confirmed Progression" will be defined as a transition from no measurable disease to measurable disease (>1 cm×1 cm). In all cases, patients with confirmed progression should stop therapy.

Preliminary & Confirmed Radiographic Response: If a measurable lesion has decreased >50% between MRI (1) and MRI (N), these patients will be categorized as "preliminary radiographic responders" and will be monitored for an additional time point and/or treatment cycle. After an additional cycle of therapy (8 weeks±4 weeks from MRI (N)), patients will receive a confirmatory MRI (N+1). If the lesion has increased >25% from MRI (N) (indicating radiographic progression from MRI (N)), this is considered an "unsustained radiographic response" or "pseudo-response". The date of radiographic progression for these patients will be MRI (N+1) and the patient should stop therapy. Alternatively, if the lesion has not increased from MRI (N), this is considered a "durable radiographic response," the patient will continue on therapy, and the date of preliminary radiographic progression is the time point of an increase >25% (from Nadir) during the remainder of the study. The investigator can then decide whether to continue safely on therapy until progression has been confirmed at the subsequent time point stop therapy if they feel the patient cannot safely continue therapy.

Stable Disease: If the lesion size has not increased or decreased beyond the set thresholds between Scan 1 and N, the patient is considered "stable." Such patients will continue on therapy, and the date of preliminary progression is the time point of an increase >25% bidirectional product (from Nadir) during the remainder of the study. Upon preliminary progression, the investigator can choose to either continue therapy and confirm progression or discontinue therapy. For cases with significant neurologic decline at the time of imaging progression as determined from MRI (N), a confirmatory scan at time point MRI (N+1) may not be possible or necessary. For these cases, it is appropriate to define MRI (N) as the progression time point.

Tissue Placement on Capillary Gap Plus Slides convection-enhanced delivery (CED) at a fixed concentration of 3 μg/mL, an infusion volume of 60 mL administered by up to 4 surgically placed catheters, as described in detail in Example 1. The duration of infusion is expected to range

TABLE 18

Summary of the Overall Objective Status for the Modified RANO Criteria for Malignant Glioma (for patients with measurable (>1 cm × 1 cm) disease): (Continued on the next page)

| Target Lesions (Current Scan) | Target Lesions (Previous Scan) | New Sites of Measurable Disease [a] | Neurological Status (KPS) | Steroid Usage | Steroid Dose | Overall Objective Status | Action |
|---|---|---|---|---|---|---|---|
| CR | Planning MRI | No | Stable/Better | No | N/A | Preliminary CR | Schedule confirmatory scan in 4 weeks |
| PR | Planning MRI | No | Stable/Better | Any | Stable/Decreased | Preliminary PR | Schedule confirmatory scan in 4 weeks |
| PD | Planning MRI | Yes or No | Stable/Better | Any | Stable/Increased | Preliminary PD | Schedule confirmatory scan in 4 weeks |
| PD | Preliminary or Confirmed PR/CR | No | Stable/Better | Any | Stable/Increased | Preliminary PD | Schedule confirmatory scan in 4 weeks |
| SD | Preliminary or Confirmed CR/PR or SD/NE or Planning MRI | No | Stable/Better | Any | N/A | SD | Continue study imaging schedule |
| PR | Preliminary PR | Yes or No | Stable/Better | Any | Stable/Decreased | Confirmed PR | Continue study imaging schedule |
| SD | Preliminary PR | Yes or No | Stable/Better | Any | Stable/Decreased | SD (Preliminary PR →Confirmed PR) | Continue study imaging schedule |
| SD | Preliminary PR | Yes or No | Stable/Better | Any | Stable/Decreased | SD (Preliminary CR →Confirmed CR) | Continue study imaging schedule |
| CR | Preliminary CR | No | Stable/Better | No | N/A | Confirmed CR | Continue study imaging schedule |
| SD | Preliminary PD | No | Stable/Better | Any | Stable/Decreased | SD (Confirmed PsP) | Continue study imaging |
| CR/PR/SD/PD/NE | CR/PR/SD/PD/NE or Planning MRI | Yes or No | Worse[b] | Any | Stable/Increased | Confirmed PD | Ensure possibility of PsP is excluded prior to withdraw of subject and proceeding to end of study [c] |
| PD | Preliminary PD | Yes or No | Any | Yes | Stable/Increasing | Confirmed PD | Ensure possibility of PsP is excluded prior to withdraw of subject and proceeding to end of study [c] |

[a] Note that new sites of measurable disease are added to the sum of bidimensional products or total lesion volume, or constitutes preliminary PD in the case of no measurable disease at baseline or best response.
[b] Definition of neurological deterioration is left to the discretion of the treating physician, but it is recommended that a decline in the KPS from 100 or 90 to 70 or less, a decline in KPS of at least 20 from 80 or less, or a decline in KPS from any baseline to 50 or less, for at least 7 days, be considered neurologic deterioration unless attributable to comorbid events or changes in corticosteroid dose (Wen et al., 2010)
[c] Investigators encouraged to robustly differentiate between true and pseudo-progression on MRI and other modalities (e.g. perfusion MRI, PET scan, TRAM, biopsy)

Example 2: Prx 321 Formulation

Introduction

This example provides further details regarding an open-label, single-arm, multi-center study of intratumoral administration of PRX 321 to patients with recurrent or progressive Glioblastoma (GB). Up to 52 subjects will receive a single intratumoral infusion of PRX 321 administered via convection-enhanced delivery (CED) at a fixed concentration of 3 μg/mL, an infusion volume of 60 mL administered by up to 4 surgically placed catheters, as described in detail in Example 1. The duration of infusion is expected to range between 24 to 36 hours depending on the flow rate and the number of convecting catheters; however, it may continue for up to 48 hours, if needed for completion.

PRX 321 Drug Product is diluted in Elliotts B® solution to produce an infusate having a final composition of PRX 321 at 3 μg/mL, 0.02% human serum albumin and gadolinium-diethylenetriamine pentaacetic acid (Gd-DTPA, Magnevist®) at 7 mM. The infusate is prepared at the hospital pharmacy; instructions for its preparation are provided below.

TABLE 19

Reagents used in the Preparation of Infusate

| Reagent | Type | Grade | Manufacturer/ Distributor | Lot/Part/Catalog # |
|---|---|---|---|---|
| PRX 321 | Drug Product | CGMP, sterile | Medicenna Therapeutics Inc. | Lot #1-FIN-2516 |
| Elliotts B ® Solution | Excipient | USP, sterile | Lukare Medical, LLC | NDC#55792-007-10 |
| HSA 5% (aqueous) Solution | Excipient | USP, sterile | Octapharma | NCT#68982-0623-02 |
| Gd-DTPA, Magnevist ® 469.1 | Excipient | USP, sterile | Bayer Healthcare Pharmaceuticals Inc. | NDC#50419-188-05 |

Abbreviations:
CGMP, Current Good Manufacturing Practice;
NDC, National Drug Code;
USP, United States Pharmacopeia PRX 321 Drug Product Composition of Drug Product: Drug product is supplied as a sterile frozen solution of PRX 321 at a concentration of 500 μg/mL contained in 0.5 mL Phosphate Buffered Saline (10 mM sodium phosphate, 500 mM sodium chloride, pH 7.4±0.1), filled in a sterile, single-use, 2 mL Type 1 USP dehydrogenated clear glass vial sealed with 13 mm Teflon-faced stopper and labeled as shown below:

PRX 321 Drug Product Vial: PRX-321 contains 0.5 mL of PRX 321 (500 μg/m) and should be stored at ≤−70° C. The vial is labeled with "Sterile Single Dose Vials for Intratumoral Administration via Stereotactically Placed Catheters".

Storage: Drug product is stored at −70° C.+/−10° C. in its secondary packaging until required for preparation of infusate. Hospital pharmacy temperature monitoring records must be provided for all periods in which drug product vial(s) are stored for review by the study monitor.

Handling: Infusate will be prepared, using aseptic technique using a pre-sanitized biological safety (vertical flow) cabinet. After the preparation of the infusate, the used drug product vial should be discarded according to the hospital pharmacy's standard operating procedure.

Excipients

Receipt of Excipients: Each shipment will contain 2 separate Excipient Kits and will arrive at the hospital pharmacy in a pre-qualified insulated shipping container. Each Excipient Kit provides materials that are to be used for a single infusate preparation. Excipient Kit inventory will be managed using the Excipient Kit Inventory Form (Appendix 3).

Each Excipient Kit contains 4 components:
Human Serum Albumin (HSA)
Elliotts B Solution
Magnevist (Gd-DTPA)
Empty IV Bag The container has a tamper seal at the opening end to secure closure. One Excipient Kit is to be used for one infusate preparation.
Excipient Kit components:
1×250 ml bottle HSA 5% (aqueous) Solution
1× unit Elliotts B Solution (10×10 mL ampules)
1×5 mL vial of Gd-DTPA
1× empty (150 mL size) IV Bag The excipient kit components are to be used in PRX 321 infusate preparation as described in the present example. The kit provides materials for single (1x) PRX 321 infusate preparation.

Storage: Excipient kit is stored at controlled room temperature until required for preparation of infusate.

Handling: Excipient kit should be handled with care and stored right side up (label of kit in at the top).

Human Serum Albumin

Human Serum Albumin (HSA) is added to the infusate, at a final concentration of 0.02%, to prevent adsorption of PRX 321 to the inner surfaces of the syringes, tubes and catheter used in the infusion assembly.

Supply: 1×250 ml bottle (Octapharma HSA 5% (aqueous) Solution, NCT #68982-0623-02)

Storage: at controlled room temperature as recommended by the manufacturer.

Handling: HSA should be handled using aseptic techniques in a pre-sanitized biological safety cabinet. Once opened and or used, the remaining HSA should be discarded according to the hospital pharmacy's standard operating procedure.

Buffered Intrathecal Electrolyte/Dextrose Injection (Elliotts B® Solution)

PRX 321 drug product is diluted in Elliotts B® Solution.

TABLE 20

Composition/Information on Ingredients:

| Specific Chemical Identity | CAS # | Chemical Formula | Quantity per mL |
|---|---|---|---|
| Calcium Chloride | 10035-04-8 | $CaCl_2$ | 0.2 mg |
| Dextrose | 50-99-7 | $C_6H_{12}O_6$ | 0.8 mg |
| Magnesium Sulfate | 10034-99-8 | $MgSO_4\ 7\ H_2O$ | 0.3 mg |
| Potassium Chloride | 7447-40-7 | KCl | 0.3 mg |
| Sodium Bicarbonate | 144-55-8 | $NaHCO_3$ | 1.9 mg |
| Sodium Chloride | 7647-14-5 | NaCl | 7.3 mg |
| Sodium Phosphate, Dibasic | 7782-85-6 | $Na_2HPO_4\ 7H_2O$ | 0.2 mg |
| Water for Injection | 7732-18-5 | $H_2O$ | 1 mL |

Further information on the Elliott's B Solution. Elliotts B® Solution is a sterile, nonpyrogenic, isotonic solution containing no bacteriostatic preservatives. Elliotts B Solution is a diluent for intrathecal administration of methotrexate sodium and cytarabine. Each 10 mL of Elliotts B Solution contains:

TABLE 21

Composition per 10 mL

| Specific Chemical Identity | Quantity per 10 mL |
|---|---|
| Sodium Chloride, USP | 73 mg |
| Sodium Bicarbonate, USP | 19 mg |
| Dextrose, USP | 8 mg |
| Magnesium Sulfate•7H2O, USP | 3 mg |
| Potassium Chloride, USP | 3 mg |
| Calcium Chloride•2H2O, USP | 2 mg |
| Sodium Phosphate, dibasic•7H2O, USP | 2 mg |
| Water for Injection, USP qs 10 mL | To 10 mL |

TABLE 22

Concentration of Electrolytes:

| Sodium | 149 mEq/liter | Bicarbonate | 22.6 mEq/liter |
|---|---|---|---|
| Potassium | 4.0 mEq/liter | Chloride | 132 mEq/liter |
| Calcium | 2.7 mEq/liter | Sulfate | 2.4 mEq/liter |
| Magnesium | 2.4 mEq/liter | Phosphate | 1.5 mEq/liter |

TABLE 23 formulae and molecular weights of the ingredients:

| INGREDIENT | MOLECULAR FORMULA | MOLECULAR WEIGHT |
|---|---|---|
| Sodium Chloride | NaCl | 58.44 |
| Sodium Bicarbonate | NaHCO3 | 84.01 |
| Dextrose | C6H12O6 | 180.16 |
| Magnesium Sulfate•7H2O | Mg2SO4•7H2O | 246.48 |
| Potassium Chloride | KCl | 74.55 |
| Calcium Chloride•2H2O | CaCl2•2H2O | 147.01 |
| Sodium Phosphate, dibasic•7H2O | Na2HPO4•7H2O | 268.07 |

The pH of Elliotts B Solution is 6.0-7.5, and the osmolarity is 288 mOsmol per liter (calculated).

Clinical Pharmacology

Elliotts B Solution provides a buffered salt solution for use as a diluent for the intrathecal administration of methotrexate sodium and cytarabine. It has been demonstrated that Elliotts B Solution is comparable to cerebrospinal fluid in pH, electrolyte composition, glucose content, and osmolarity:

TABLE 24

Comparison of Electrolyte Composition, pH and Nonelectrolytic Constituents of Elliotts B Solution and CSF:

| Solution | Na+ mEq/L | K+ mEq/L | Co++ mEq/L | Mg++ mEq/L | HCO3– mEq7L | Cl– mEq/L | pH | Phosphorus mg/dL | Glucose mg/dL |
|---|---|---|---|---|---|---|---|---|---|
| Cerebrospinal Fluid | 117-137 | 2.3-4.6 | 2.2 | 2.2 | 22.9 | 113-127 | 7.31 | 1.2-2.1 | 45-80 |
| Elliotts B Solution | 149 | 4.0 | 2.7 | 2.4 | 22.6 | 132 | 6.0-7.5 | 2.3 | 80 |

The approximate buffer capacity of Elliotts B Solution is $1.1 \times 10^{-2}$ equivalents when the challenge solution is 0.01 N HCl and $7.8 \times 10^{-3}$ equivalents when the challenge solution is 0.01 N NaOH. Compatibility studies with methotrexate sodium and cytarabine indicate these drugs are physically compatible with Elliotts B Solution.

Elliott's B solution is a diluent used in the preparation of infusate; it is comparable to cerebrospinal fluid in pH, electrolyte composition, glucose content, osmolarity and buffering capacity.

Supply: 1 unit (clear glass 10 mL ampules, packaged 10 ampules per box) (commercially available from Lukare Medical).

Storage: stored according to manufacturer's instructions.

Handling: Elliotts B® Solution should be handled using aseptic techniques in a pre-sanitized biological safety cabinet. Once the Elliotts B® Solution ampule has been open and or used, the remaining should be discarded according to the site/hospital pharmacy's standard operating procedure.

Gadolinium-Diethylenetriamine Pentaacetic Acid (Gd-DTPA) Magnevist®

Gd-DTPA (diluted to ~1:70) is added to the infusate as a contrast agent as co-infusion of this surrogate tracer during infusion allows real-time monitoring of PRX 321 infusate distribution.

Supply: 1×5 mL single use vial of Gd-DTPA (Bayer HealthCare Pharmaceuticals Inc. Magnevist®; 469.1 mg/mL, NDC #50419-188-05).

Storage: stored according to manufacturer's instructions.

Handling: Gd-DTPA (Magnevist®) should be handled using aseptic techniques in a pre-sanitized biological safety cabinet. Once opened or used, the remaining should be discarded in accordance with regulations dealing with the disposal of such materials and according to the hospital pharmacy's standard operating procedure.

Ancillary Component Provided in Excipient Kit

Sterile IV bag is used in infusate preparation serving as a container in which the Drug Product and excipients are mixed.

Supply: 1× empty (150 mL size) INTRAVIA Container with PVC Ports, Sterile fluid path (Baxter, Product #2B8011)

Storage: stored according to manufacturer's instructions.

Handling: IV bag should be handled, using aseptic techniques in a pre-sanitized biological safety cabinet. Once opened or used, the bag should be discarded according to the hospital pharmacy's standard operating procedure.

Preparation and Dispensing of Infusate

Sterility: Aseptic technique must be used to maintain the sterility of infusate. This includes wearing sterile gloves, surface disinfection of all vials using approved disinfectant per the hospital/institution SOP's, and preparing the infusate in a pre-sanitized biological safety cabinet.

Preparation of Sterile Infusate

Within 24 hours prior to the scheduled infusion of a subject, the Investigator or designee will provide a subject specific treatment plan to the pharmacist specifying the dispensing information for the infusion. The total infusion volume for all subjects will be 60 mL.

Within 2 hours of the scheduled catheter placement start time, the infusate is prepared at Room Temperature in a pre-sanitized biological safety cabinet, as described below:
  Every component used in infusate preparation will be sanitized using alcohol wipes.
  One PRX 321 Drug Product vial is removed from the −70° C. freezer and thawed at room temperature and stored on ice upon thawing. Thawing time is approximately 15 minutes.
  One Excipient Kit is removed from storage and each content placed in the biological safety cabinet.
  The following solutions are added to the IV bag through the rubber septum port in the specified order below. The rubber septum of the IV bag septum is specifically also sanitized using an alcohol wipe.
NOTE: Do not Mix Until Directed. When Measuring Each Reagent, Withdraw and Dispense Liquids Very Gently and Very Slowly to Avoid Agitation or any Bubble Formation.
  68.32 mL of Elliott's B® Solution"
    As Elliott's B® Solution is supplied in 10 mL ampules, multiple ampules must be aseptically combined in the IV bag.
    Note: Elliott's B® Solution ampules are slightly overfilled to greater than 10 mL. As such, contents from each ampule must be measured first before adding to the IV bag until the required volume is achieved.
    "To transfer the Elliott's B® Solution to the IV bag, snap the glass seal off of each ampule and aseptically remove the Elliotts B from the vial using a 60 ml syringe fitted with a 16 Gauge needle that is at least 1 inch (preferably longer) in length. Slowly draw back the syringe to siphon the ampule contents and repeat until 34 mL has been aspirated. Transfer to the IV bag through the rubber septum port. Repeat this step to transfer an additional remaining 34 mL.
    " Using a 1 mL syringe measure the remaining 0.32 mL and aseptically transfer to the IV bag through the rubber septum port.
    Aspirate and dispense Elliotts B very slowly at a rate of ~10 ml/minute to avoid any agitation or bubble formation.
  0.28 mL of 5% HSA using a 1 mL syringe fitted with a needle (20-23 Gauge)
    "If the needle is not long enough to clear the injection port keep the bag in an upright position and ensure the port is filled with Elliotts solution prior to injection.
  0.98 mL of Gd-DTPA (Magnevist®) using a 3 mL syringe fitted with a needle (20-23 Gauge).
    If the needle is not long enough to clear the injection port keep the bag in an upright position and ensure the port is filled with Elliotts solution prior to injection.
  Mix by very gently inverting 3 times. Do not vortex or shake. Do not invert more than 3 times. Ensure the injection port is filled with solution after each inversion and massage to ensure the port is thoroughly washed out.
  0.42 mL of PRX 321 Drug Product using a 1 ml syringe fitted with a needle (20-23 Gauge).
    If the needle is not long enough to clear the injection port keep the bag in an upright position and ensure the port is filled with Elliotts solution prior to injection.
  Mix by very gentle inversion 5 times. Do not vortex or shake. Do not invert more than 5 times. Ensure the injection port is filled with solution after each inversion and massage to ensure the port is thoroughly washed out.
NOTE: To Avoid Foaming, all Ingredients should be Added to the IV Bag Very Gently and the IV Bag should not be Shaken or its Contents Stirred. Mixing of the Above Ingredients is Accomplished by Inverting the IV Bag Very Gently 5 Times.

The resulting infusate has a final PRX 321 concentration of 3 µg/mL with 0.02% HSA and Gd-DTPA 7 mM, in a total volume of 70 mL. Aseptically transfer the infusate from IV bag into syringes according to dispensing instructions (see below).

Dispensing of Infusate
  Required Materials: 20 mL and/or 30 mL Medfusion 3500 compatible Sterile Luer-lock syringe(s) are required for dispensing the infusate. Number and size of syringe(s) dispensed is determined based on the number of catheters placed and outlined in the subject specific treatment plan.
  NOTE: Always Employ Aseptic Techniques During Infusate Transfer; Transfer the Infusate from the IV Bag into Syringes Immediately Following Infusate Preparation.
  Dispensing Instructions: Infusate will be divided into up to 4 sterile luer lock syringes in a biological safety cabinet as outlined in the subject specific treatment plan. A 16-gauge needle of sufficient length on the end of the appropriately sized syringe should be used to aspirate the infusate from the IV bag septum port slowly at a rate of ~10 mL/minute. Please refer to the subject treatment plan worksheet for the appropriate size syringe and required volume to aspirate/syringe.
  NOTE: When Aspirating Infusate from IV Bag to Dispensing Syringes Pull Back on the Plunger Gently to Avoid Agitation and Frothing of the Solution.
  Prepared syringes will be labeled with the catheter number (1, 2, 3, 4 as applicable) consistent with the subject specific treatment plan and delivered to the Operating Room according to the hospital pharmacy's standard operating procedures for maintaining sterility. Dispensing must be documented by the Pharmacist or designee using the Drug Accountability form (Appendix 2) for that subject.
  Time for Dispensing Infusate to Operating Room: Infusate must be dispensed to Operating Room where study subject is undergoing surgery for placement of catheter(s) prior to catheter(s) being placed since the infusate is required to prime the catheters. It is the responsibility of the designated site study staff member to inform the pharmacist of the scheduled catheter placement start time.
  NOTE: Infusate is to be Prepared/Dispensed in Syringes and Delivered to the Operating Room within 2 Hours of the Scheduled Catheter Placement Start Time. Syringes can be Stored at 2-8° C. Following Preparation Until Delivered to the Study Subject.
  All syringes either empty or containing residual unused infusate must be accounted for by the site staff monitoring the infusion using the source worksheets to capture volume of infusate left in each syringe and then discarded according to hospital pharmacy's standard operating procedure.

Repeat Infusate Preparation on Day 1
  Preparation of the infusate will occur twice for every subject as duration of infusion for administration of the total prescribed volume (60 mL) will exceed 24 hours. While the infusate is stable for at least 24 hours from the time it is prepared, at 20-24 hours after start of Infusion on Day 1, new infusate should be prepared and the initial dispensed syringes replaced with new syringes containing fresh infusate.

The second vial of PRX 321 as well as the second excipient kit will be used to prepare fresh sterile infusate to be administered starting at the 20-24 hour infusion time point through the remainder of the infusion time. Fresh infusate should be prepared following the same preparation and dispensing procedures outlined herein for preparation and for dispensing. The only difference is that fresh syringes will be dispensed to hospital floor where the study subject is located rather that the Operating Room.

Example 3: Image Guided High Flow CED in Recurrent Glioblastoma (RGBM)

Initial Experience from Phase 2 Study of a Targeted Immunotherapy, PRX 321 (CPIL-4PE)

Introduction: PRX 321 is a targeted immunotherapeutic agent comprising a circularly permuted interleukin-4 fused to a truncated version of *Pseudomonas* exotoxin A (PE). PRX 321 binds to the interleukin-4 receptor, over-expressed by glioblastoma cells and immunosuppressive cells of the tumor microenvironment, and is endocytosed with the cleaved PE domain inducing tumor cell death via ADP-ribosylation of the Elongation Factor-2.

Methods: The current study is a multi-center, single-arm, Phase 2b study of intratumoral infusion of PRX 321 in rGBM using a stepped catheter, infusion modelling (for catheter placement) and intra-operative real-time imaging of drug distribution. Infusions are started at 3 µL/min/catheter then progressively increased under real-time MRI imaging according to the observed pattern of drug distribution and proximity of key structures.

An interim evaluation of CED success, tolerability and safety was completed.

Drug concentration: 1.5 µg/mL

Volume of Infusion: 7-60 mL-personalized based on tumor volume

Flow Rate: Up to 30 µL/min/catheter as higher flow rates improve distribution

Catheters: 1 cm-2 cm tumor: up to 2 catheters or 2 cm-4 cm tumor: up to 4 catheters.

Real-Time Infusion Monitoring-first 3-6 hours of infusion: Gadolinium.

Catheter Trajectory Planning: Brainlab iPlan® Flow software.

Results: 10 rGBM subjects at $1^{st}$ or $2^{nd}$ recurrence with tumors 1.8-4.3 cm in diameter received 12-66 ml of PRX 321 delivered at a concentration of 1.5 µg/mL via 1-3 catheters at flow-rates of up to 15 µL/min/catheter.

TABLE 25

Summary of Safety

| Subjects (n) with AE Gd ≥ 3 | SAE (n) | Related AE [Grade 1&2] (n) | Related AE [Grade 3&4] (n) | Related AE during infusion [all grades] (n) |
|---|---|---|---|---|
| 2 | 1 (not related) | 2 | 0 | 2 (all grade 1) |

No SUSARs have been reported and no reports suggestive of acutely raised ICP, cerebral irritation or volume-related effects. AEs are generally consistent with the underlying disease.

Some remarkable distributions have been observed. Tumor coverage ranged from 43% to 100%, with 70% and 40% coverage of 1 cm and 2 cm penumbra respectively. Ratio of volume of distribution (Vd) to the volume infusion (Vi) ranged from 2.2 to 0.6. Reasons for lower Vd/Vi ratios will be detailed.

When catheter placement was inaccurate, realtime imaging of GdDTPA distribution enabled adjustments to catheter depth which dramatically improved tumor coverage.

Conclusions: Initial safety profile acceptable-consistent with nature of disease and therapy. Selection of candidates for CED is important. Peer to peer technical support & experience exchange very important. Volumes up to 60 ml at rates up to 20 µl/min are tolerated. Avoidance of (early) leakage into CSF is desirable but unpredictable. High percentage coverage can be achieved but room for further optimization. Operational complexity can be overcome with good planning. Protocol revised to fixed 60 ml volume for all subjects.

Step-up of infusion rates under real-time MRI guidance enables delivery of PRX 321 by CED in rGBM at infusion rates of up to 15 µL/min/catheter. MRI guidance is therefore critical for optimal drug distribution in brain tumors. Reassuring initial safety review enabled ongoing recruitment in the study.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method of treating a central nervous system (CNS) tumor in a subject, comprising intratumorally administering to the subject a formulation comprising:
   i. an IL-4 targeted cargo protein in an artificial cerebral spinal fluid (CSF) solution, and
   ii. 0.02% human serum albumin, wherein the formulation is optionally co-administered with a surrogate tracer to a subject in need thereof.

2. The method of claim 1, wherein the IL-4 targeted cargo protein comprises one or more cargo moieties, optionally wherein the cargo protein comprises a toxin.

3. The method of claim 2, wherein the toxin is selected from the group consisting of a bacterial toxin, animal toxin, and plant toxin.

4. The method of claim 1, wherein the IL-4 targeted cargo protein comprises a pro-apoptosis member of the BCL-2 family selected from the group consisting of BAX, BAD, BAT, BAK, BIK, BOK, BID BIM, BMF, and BOK.

5. The method of claim 1, wherein the IL-4 targeted cargo protein comprises PRX 321 (SEQ ID NO:1) or a derivative or variant thereof.

6. The method of claim 1, wherein the surrogate tracer is a gadolinium-bound tracer or a magnetic resonance imaging (MRI) contrast agent.

7. The method of claim 1, wherein the IL-4 targeted cargo protein comprises an IL-4R antibody as the targeting moiety.

8. The method of claim 1, wherein the IL-4 targeted cargo protein comprises a human cargo moiety selected from the group consisting of RNase A and perforin.

9. The method of claim 1, wherein the subject has a recurrent CNS tumor, a refractory CNS tumor, a newly diagnosed CNS tumor, an IL-4R positive CNS tumor, an 06-methylguanine-methyltransferase (MGMT) positive CNS tumor, or a furin positive CNS tumor.

10. The method of claim 1, further comprising determining whether the subject is refractory to radiation or chemotherapy; wherein if the subject is refractory it indicates that the subject will benefit from administration of the IL-4 targeted cargo protein.

11. The method of claim 1, further comprising administering chemotherapy or radiation therapy to the subject before, during, or after administering the IL-4 targeted cargo protein, and/or surgically removing at least part of a tumor before, during, or after administering the IL-4 targeted cargo protein.

12. The method of claim 1, wherein the IL-4 targeted cargo protein is administered by convection-enhanced delivery (CED).

13. The method of claim 1, wherein the IL-4 targeted cargo protein is administered as a single dose.

14. The method of claim 1, wherein the IL-4 targeted cargo protein is administered as a single dose of about 90 μg (1.5 μg/mL) to about 300 μg (3 μg/mL) over 1 day, 2 days, 3 days, 4 days, 5 days, 6 days, 7 days, or 8 days as 1, 2, 3, 4, or 5 infusions.

15. The method of claim 1, wherein the IL-4 targeted cargo protein is administered via one or more intracranial catheters with a flow rate of about 5 μL/min/catheter to about 20 μL/min/catheter and at a concentration of about 1.5 μg/mL.

16. The method according to claim 1, wherein the intratumoral administration comprises intracranial administration.

17. The method according to claim 1, wherein the IL-4 targeted cargo protein is administered via an intracranial catheter.

18. The method according to claim 1, wherein the CNS tumor is selected from the group consisting of glioma, glioblastoma, astrocytoma, medulloblastoma, craniopharyogioma, ependymoma, pinealoma, hemangioblastoma, acoustic neuroma, oligodendroglia, menangioma, meningioma, neuroblastoma, and retinoblastoma.

19. The method according to claim 1, wherein the CNS tumor is a recurrent or refractory glioblastoma.

20. The method according to claim 1, wherein the IL-4 targeted cargo protein is PRX 321.

* * * * *